US006093816A

United States Patent [19]
Lin et al.

[11] Patent Number: 6,093,816
[45] Date of Patent: Jul. 25, 2000

[54] CATIONIC LIPIDS

[75] Inventors: Kuei-Ying Lin, Fremont; Mark D. Mattuecci, Burlingame, both of Calif.

[73] Assignee: Isis Pharmaceuticals, Inc., Carlsbad, Calif.

[21] Appl. No.: 08/672,206

[22] Filed: Jun. 27, 1996

[51] Int. Cl.$^7$ ............... C07D 413/02; C07D 265/30; C07D 295/18; A61K 31/535; A61K 37/7115

[52] U.S. Cl. ............... 544/122; 436/136; 514/238.2; 514/357; 514/399; 514/400; 530/350; 536/623.1; 544/143; 544/168; 546/336; 548/312.1; 548/314.4; 548/334.1; 548/338.1

[58] Field of Search ............... 548/338.1, 312.1, 548/334.1, 314.4; 514/396–400, 238–22, 357; 544/122, 143, 168; 546/336; 436/163, 2; 530/350; 536/23.1

[56] References Cited

U.S. PATENT DOCUMENTS

| | | | |
|---|---|---|---|
| 2,426,891 | 9/1947 | Lynch | 260/403 |
| 3,190,917 | 6/1965 | Johnson et al. | 548/338.1 X |
| 3,387,031 | 6/1968 | Johnson et al. | 548/338.1 X |
| 4,229,360 | 10/1980 | Schneider et al. | 260/403 |
| 4,388,466 | 6/1983 | Beyet et al. | 548/338.1 X |
| 4,548,955 | 10/1985 | Okahata et al. | 521/53 |
| 4,857,319 | 8/1989 | Crowe et al. | 424/94.1 |
| 4,863,905 | 9/1989 | Hudspeth et al. | 514/18 |
| 4,880,635 | 11/1989 | Janoff et al. | 424/450 |
| 5,171,678 | 12/1992 | Behr et al. | 435/172.3 |
| 5,252,559 | 10/1993 | Kronholm et al. | 514/18 |
| 5,283,185 | 2/1994 | Epand et al. | 435/172.3 |
| 5,459,127 | 10/1995 | Felgner et al. | 514/7 |
| 5,543,423 | 8/1996 | Zelle et al. | 514/332 |
| 5,571,792 | 11/1996 | Bolton et al. | 514/618 |
| 5,583,020 | 12/1996 | Sullivan | 435/172.3 |
| 5,614,503 | 3/1997 | Chaudhary et al. | 514/44 |
| 5,759,827 | 6/1998 | Legendre et al. | 435/772.1 |

FOREIGN PATENT DOCUMENTS

| | | |
|---|---|---|
| 0 391 179 A2 | 10/1990 | European Pat. Off. . |
| 0 394 111 A1 | 10/1990 | European Pat. Off. . |
| WO 91/16024 | 10/1991 | WIPO . |
| WO 93/05162 | 3/1993 | WIPO . |
| WO 94/05624 | 3/1994 | WIPO . |
| WO 95/14380 | 6/1995 | WIPO . |
| WO 95/35094 | 12/1995 | WIPO . |
| WO 96/01840 | 1/1996 | WIPO . |
| WO 96/01841 | 1/1996 | WIPO . |
| WO 96/10390 | 4/1996 | WIPO . |
| WO 96/18372 | 6/1996 | WIPO . |
| WO 96/40962 | 12/1996 | WIPO . |

OTHER PUBLICATIONS

Koo et al., "A study on the hydrolysis of p–nitrophenyl carboxylates by micellar surfactants catalysts containing histidyl residue", 111(17):149399e, Chem AB, 10/23/89.

Korakas et al., "Structure–retention relationships of diastereopmeric mixtures of lipidic amino acid conjugates on reversed–phase stationary phases", 659:307–315, Journal of Chromatography, 1994.

Murakami et al., "General–Base Catalysis of the Hydrolysis of p–Nitropheny Carboxlates by Micellar Surfactants Involving a Histidyl Residue", 103:2750–2756, J am Chem Soc, 1981.

Murakami et al., "Catalytic Efficiency of Functionalized Vesicles in the Transamination of Pyridoxal–5'–phosphate with a Hydrophobic Amino Acid", 55:3004–3012, Bull Chem Soc Jpn, 1982.

Shinozuka et al., "Enantiomeric Bleomycin Model Compounds Bearing Long Alkyl–Chain", 32(47):6869–6872, Tet Lett, 1991.

Ciccarone et al., "Cationic Liposome–Mediated Transfection: Effect of Serum on Expression and Efficiency," Focus 15(3):80–83 ( ).

Felgner et al, "Enhanced Gene Delivery and Mechanism Studies with a Novel Series of Cationic Lipid Formulations," J Biol Chem 269(4):2550–2561 (1994).

Firestone et al., "Lysosomotropic Agents II. Synthesis and Cytotoxic Action of Lysosomotropic Detergents," Lysosomotropic Detergents pp. 1455–1464 ( ).

Firestone et al., "Lysosomotropic Agents. 1. Synthesis and Cytotoxic Action of Lysosomotropic Detergents," J Med Chem 22(9):1130–1133 (1979).

Firestone et al., "Lysosomotropic Agents. 7. Broad–Spectrum Antifungal Activity of Lysosomotropic Detergents," J Med Chem 30:1519–1521 (1987).

Firestone et al., "Selective Delivery of Cytotoxic Compounds to Cells by the LDL Pathway," J Med Chem 27:1037–1043 (1984).

Forster et al., "The effect of lysosomotropic detergents on the permeability properties of the lysosome membrane," Biochem Biophys Acta 924:452–457 (1987).

Hawley–Nelson et al., "LipofectAMINE Reagent: A New, Higher Efficiency Polycationic Liposome Transfection Reagent," Focus 15(3):73–79 ( ).

Hussain et al., "Killing of Saccharomyces cerevisiae by the Lysosomotropic Detergent N–Dodecylimidazole," Antimicro AG & Chemo 31(4):512–517 (1987).

Jaaskelainen et al., "Oligonucleotide–Cationic Liposome Interations. A Physicochemical Study," Biochem Biophys Acta 1195:115–123 (1994).

Leserman et al., "Immunoliposome–Mediated Delivery of Nucleic Acids: A Review Of Our Laboratory's Experience," Journal Liposome Research 4(1):107–119 (1994).

Miller et al., "Cell Killing by Lysosomotropic Detergents," J Cell Biol 97:1841–1851 (1983).

(List continued on next page.)

*Primary Examiner*—Floyd D. Higel
*Attorney, Agent, or Firm*—Woodcock Washburn Kurtz Mackiewicz & Norris LLP

[57] ABSTRACT

The present invention is directed to new cationic lipids and intermediates in their synthesis that are useful for transfecting nucleic acids or peptides into prokaryotic or eukaryotic cells. The lipids comprise one or two substituted histidine residues, or similar compounds, linked to a lipophilic moiety. The lipids form a complex when mixed with polyanions such as nucleic acids or peptides. The complexes permit efficient transfer of polyanions into cells, usually without significant toxicity to the cells.

34 Claims, No Drawings

OTHER PUBLICATIONS

Murakami et al, "Aggregate Morphology and Intermembrane Interaction of Synthetic Peptide Lipids Bearing Various Head Group," J Am Chem Soc 107(7):2161–2167 (1985).

Murakami et al, "Preparation of Stable Single–Compartment Vesicles with Cationic and Zwitterionic Amphiphiles Involving Amino Acid Residues," J Org Chem 47(11):2137–2144 (1982).

Murakami et al., "Synthetic Peptide Lipids Having Axial Chirality. Preparation and Aggregate Morphology.," Chemistry Letters, Tokyo JP 7:1481–1484 (1987).

Perrin et al., "pKa Prediction for Organic Acids and Bases," Chapman and Hall Ltd. pp. 1–65 (1981).

Puyal et al.,a "A new cationic liposome encapsulating genetic material," Eur J Biochem 228:697–703 (1995).

Remy et al., "Gene Transfer with a Series of Lipophilic DNA–Binding Molecules," Bioconj Chem 5(6):647–654 (1994).

Ropert et al., "Oligonucleotides Encapsulated in pH Sensitive Liposomes are Efficient Toward Friend Retrovirus," Biochem Biophys Res Comm 183(2):879–885 (1992).

Singhal et al, "Direct Gene Transfer by Liposomes," Journal Liposome Research 4(1):289–299 (1994).

Smart et al., "Surface Titration: A Continuum Electrostatics Model," J Am Chem Soc 118:2283–2284 (1996).

Wilson et al., "The Role of Lysosomal Enzymes in Killing of Mammalian Cells by the Lysomotropic Detergent N–Dodecylimidazole," J Cell Biol 104:1223–1229 (1987).

Xu et al., "Mechanism of DNA Release from Cationic Liposome/DNA Complexes Used in Cell Transfection," Biochem 35:5616–5623 (1996).

Zalipsky et al., "Long circulating, cationic liposomes containing amino–PEG–phosphatidylethanolamine," FEBS 353:71–74 (1994).

Zulauf et al, "[29] Critical Micellar Concentrations of Detergents," Methods in Enzymology 172:528–538 (1989).

Boussif et al., "A versatile vector for gene and oligonucleotide transfer into cells in culture and in vivo: Polyethylenimine," Proc Natl Acad Sci 92:7297–7301(Aug. 1995).

Chu et al. "Efficiency of Cytoplasmic Delivery by pH–Sensitive Liposomes to Cells in Culture," Pharm Res 7(8):824–834 (1990).

Dijkstra et al., "Interaction of Liposomes with Kupffer Cells in Vitro," Experimental Cell Research 150:161–176 (1984).

Kuppermann et al., "Liposome–Encapsulated (S)–1–(3–Hydroxy–2–Phosphonylmethoxypropyl)cytosine for Long–Acting Therapy of Viral Retinitis," The Journal of Infectious Diseases 173:18–23 (1996).

Murakami et al., "Aggregation Behavior of Amphiphiles Functionalized with Dipeptide Segments an Enantioselective Ester Hydrolysis in Their Bilayer Membranes," Bull Chem Soc Jpn 58(1):172–180 (1985).

Tycko et al., "Rapid Acidification of Endocytic Vesicles Containing alpha2–Macroglobulin," Cell 28:643–651 (Mar. 1982).

Wang et al., "Highly Efficient DNA Delivery Mediated by pH–Sensitive Immunoliposomes,"Biochem 28:9508–9514 (1989).

Behr, Jean–Paul, "DNA Strongly Binds to Micelles and Vesicles Containing Lipopolyamines or Lipointercalants, " Tet Lett 27(48):5861–5864 (1986).

Behr, Jean–Paul, "Synthetic Gene–Transfer Vectors, " ACC Chem Res 26:274–278 (1993).

Felgner, Philip L., "Particulate systems and polymers for in vitro and in vivo delivery of polynucleotides," Advanced Drug Delivery Reviews 5:163–187 (1990).

Kato et al., "Synthetic Cationic Amphifile for Limposome––Mediated DNA Transfection with Less Cytotoxicity," Biol Pharm Bull 19(6):860–863 (1996).

Legendre et al., "Delivery of Plasmid DNA into Mammalian Cell Lines Using pH–Sensitive Liposomes: Comparison with Cationic Liposomes," Pharm Res 9(10):1235–1242 (1992).

Reimer et al., "Formation of Novel Hydrophobic Complexes between Cationic Lipids and Plasmid DNA," Biochem 34:12877–12883 (1995).

Solodin et al., "A Novel Series of Amphiphilic Imidazolinium Compounds for in Vitro and in Vivo Gene Delivery", Biochemistry 34:13537–13544 (1995).

CATIONIC LIPIDS

BACKGROUND OF THE INVENTION

The present invention relates to new cationic lipids and synthetic intermediates therefor as well as their use for delivering therapeutic compounds, particularly anionic and polyanionic polymers such as nucleic acids and peptide compounds into eukaryotic and prokaryotic cells.

Workers have described lipids that are useful for delivering or transfecting into cells nucleic acids, peptides, proteins and other compounds such as lipophilic and anionic therapeutic agents (WO 96/10390; WO 96/01841; WO 96/01840; WO 95/35094; WO 95/12386; WO 94/05624; WO 94/00569; WO 93/24640; WO 91/16024; WO 90/14074; WO 90/11092; U.S. Pat. Nos. 5,459,127, 5,283,185, 5,171,687, 5,286,634, 4,880,635, 4,857,319 and 4,229,360; Boussif et al. *Proc. Natl. Acad. Sci.* (U.S.A.) 92:7297–7301, 1995; Budker et al. *Nature Biotech.* 14:760–764; Felgner et al. *J. Biol. Chem.* 269:2550–2561, 1994; Koff et al. *Science* 224:1007–1009 1980; Jaaskelainen et al. *Biochim, Biophys. Acta* 1195:115–123, 1994; Leserman et al. *J. Liposome Res.* 4:107–119, 1994; Lewis et al. *Proc. Natl. Acad. Sci.* (U.S.A.) 93:3176–3181, 1996; Nabel et al. *Proc. Natl. Acad. Sci.* (U.S.A.) 90:11307, 1993; Nabel et al. *Hum. Gene Ther.* 3:649, 1992; Nabel et al. *Science* 249:1285–1288, 1990; Philip et al. *J. Biol. Chem.* 268:16087–16090, 1993; Puyal et al. *Eur. J. Biochem.* 228:697–703, 1995; Remy et al. *Bioconjugate Chem.* 5:647–654, 1994; Ropert et al. *Biochem. Biophys. Res. Commun.* 183:879–885, 1992; Stribling et al. *Proc. Natl. Acad. Sci.* (U.S.A.) 89:11277–11281, 1992; Tong et al. *Acta Pharm. Sinica* 27:15–21, 1991; van Borssum Waalkes et al. *Biochim, Biophys. Acta* 1148:161–172, 1993; Walker et al. *Proc. Natl. Acad. Sci.* (U.S.A.) 89:7915–7919, 1992; Zalipsky et al. *FEBS Letters* 353:71–74, 1994; Zhu et al. *Science* 261:209–211, 1993; Xu et al. *Biochem.* 35:5616–5623, 1996; D. D. Lasic *Liposomes: From Physics to Applications,* Elsevier, Amsterdam, 1993.

OBJECTS OF THE INVENTION

The invention lipids or methods include one or more compounds or methods that accomplish one or more of the following objects.

It is an object of the invention to provide cationic lipids and intermediates for making such lipids.

Another object of the invention is to provide cationic lipids that are suitable for delivering or transfecting compounds such as nucleic acids, peptides, and anionic therapeutic agents into cell cytoplasm or cell nuclei in vitro or in vivo in the presence or absence of serum or blood.

Another object of the invention is to provide cationic lipids that are suitable for efficiently delivering polyanionic polymers such as nucleic acids into cells using cells in tissue culture at a cell confluency of about 50% to 100%.

Another object of the invention is to provide cationic lipids that are suitable for efficiently delivering a large amount of polyanionic polymers such as nucleic acids, proteins, peptides or anionic therapeutic agents into cells.

Another object of the invention is to provide cationic lipids having improved pharmacological or other properties such as, improved storage stability, reduced toxicity or increased efficacy in the presence of serum or in the presence of components found in tissue culture medium.

Another object of the invention is to obviate the need to use a colipid such as DOPE in the intracellular delivery of nucleic acids, oligonucleotides or other anionic compounds into cells in vitro or in vivo.

Another object of the invention is to provide cationic lipids that are suitable for efficiently delivering polyanionic polymers such as nucleic acids or peptides sytemically to the lung, spleen or other organs of a mammal such as rodents, non-human primates or humans.

Another object of the invention is to provide methods to deliver anionic compounds or hydrophobic compounds into cells in vitro or in vivo.

Another object of the invention is to provide compositions comprising cationic lipids and anionic compounds or therapeutic agents such as nucleic acids, peptides, proteins, oligonucleotides, or antiviral agents. Such compositions optionally contain colipid(s).

Another object of the invention is to provide compositions comprising cationic lipids and hydrophobic compounds or therapeutic agents such as antitumor or antifungal agents. Such compositions optionally contain colipid(s).

SUMMARY OF THE INVENTION

Invention embodiments include cationic lipids and intermediates therefor having the structure $\underline{A}$

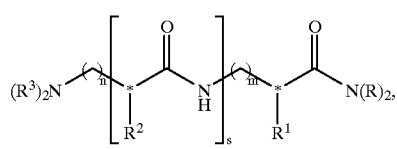

wherein
each R is independently hydrogen or a lipophilic moiety, the lipophilic moieties typically consisting of 1 or 2 groups, usually 2, containing at least about 10 linked carbon atoms, typically about 10–50 linked carbon atoms, usually about 10–22 linked carbon atoms and R is optionally selected from alkyl ($C_{10\text{-}22}$), a mono-, di- or tri-unsaturated alkenyl ($C_{10\text{-}22}$) group, or one R is a cholesteryl moiety and the other R is hydrogen, provided that both R are not hydrogen;

$R^1$ and $R^2$ are independently hydrogen, $-(CH_2)_z-N(R^4)_2$, $-(CH_2)_zNR^4-C(=NH)-N(R^5)_2$, or $W^1$, provided that at least one of $R^1$ and $R^2$ is $W^1$;

each $R^3$ is independently hydrogen, alkyl ($C_{1\text{-}10}$), $-CH_2-(CF_2)_p-CF_3$, aryl (e.g., phenyl or naphthyl), a protecting group, or both $R^3$ together are a protecting group, or one $R^3$ is hydrogen and the other $R^3$ is $-C(O)CH_2NH_2$ or $-C(O)CH(CH_3)NH_2$, provided that both $R^3$ are not aryl;

each $R^4$ is independently hydrogen, alkyl ($C_{1\text{-}6}$) (e.g., methyl, ethyl, propyl, isopropyl), a protecting group, $-CH_2-(CF_2)_p-CF_3$, or both $R^4$ together are a protecting group;

each $R^5$ is independently hydrogen, alkyl ($C_{1\text{-}6}$) (e.g., methyl, ethyl, propyl, isopropyl), a protecting group, or both $R^5$ together are a protecting group;

each $W^1$ is independently a cationic group, at least one of which has a pKa of about 6.0–7.5, $W^1$ is optionally selected from

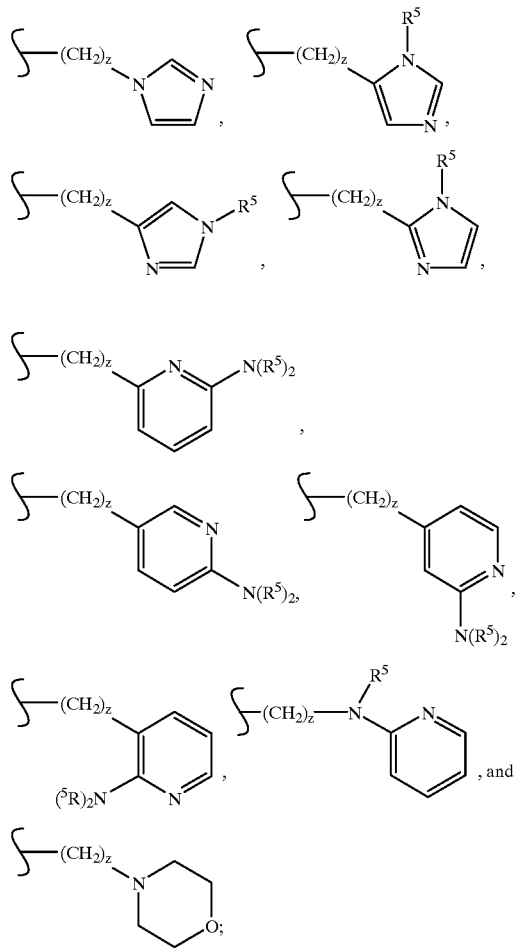

m is an integer having the value 0, 1, 2, 3 or 4, usually 0 or 1;

n is an integer having the value 0, 1, 2, 3 or 4, usually 0 or 1;

p is an integer having the value 0, 1, 2, 3, 4, 5, 6, 7, 8, 9, or 10;

s is an integer having the value 0, 1 or 2, usually 0 or 1;

z is an integer having the value 1, 2, 3, or 4, usually 0 or 1;

positions designated * are carbon atoms with linked substituents in the R, S or RS configuration; and the salts, tautomers, solvates, resolved, partially resolved and unresolved enantiomers, purified, partially purified and unpurified positional isomers or diastereomers thereof. Structure $\underline{A1}$ cationic lipids are compounds where each $W^1$ independently has structures shown for $\underline{A}$, with the remaining portions of the structure being the same as $\underline{A}$.

Invention embodiments include cationic lipids and intermediates therefor having the structure $\underline{E}$

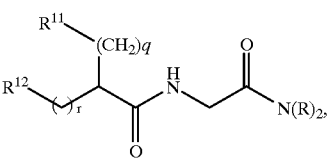

wherein q and r are each independently 0, 1, 2 or 3, usually q is 0 and r is 1 or q is 1 and R is 0;

$R^{11}$ is a moiety with a pKa of about 6.0–10, usually about 7.0–8.5; and $R^{12}$ is a $W^1$ moiety with a pKa of about 6.0–7.5 such as $\underline{B}$, $\underline{C}$ or $\underline{D}$

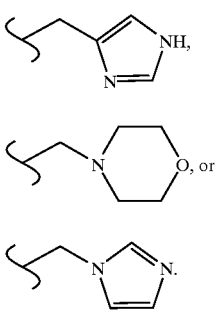

In structure $\underline{E}$ compounds, when q is 0, $R^{11}$ is —$N(R^4)_2$ or —$N(R^{14})(R^4)$ where $R^{14}$ is hydrogen or alkyl ($C_{1-6}$) and when q is 1, 2, or 3, $R^{11}$ is an amine substituted with an electron withdrawing substituent, e.g., $R^{11}$ is —NH—$CH_2$—CN, —NH—$CH_2$—$NO_2$, —NH—$CH_2$—$SO_2R^{15}$, —NH—$CH_2$—C(O)$(CH_2)_m CH_3$, —NH—$CH_2(CF_2)_m CF_3$, or —NH—$CH_2O(CH_2)_m CH_3$, where $R^{15}$ is hydrogen or alkyl ($C_{1-6}$). $R^{11}$ has a greater positive charge at a pH about 7 than $R^{12}$. At a pH of about 7, $R^{12}$ has a charge that is significantly less than +1.0 (about 0.1–0.6) and a charge of about +0.8–1.0 at lower pH of about 5–6. The presence of an electron withdrawing substituent at $R^{11}$ reduces the pKa of the charged moiety when q is 1, 2, or 3 and the charged moiety is located farther from the carbonyl group.

In some embodiments, the structure $\underline{A}$ or $\underline{E}$ lipids have 1, 2, or 3 moieties, usually 1 or 2, with a pKa of about 6.0–7.5 wherein the pKa is determined by the process of: (a) preparing a water solution containing a suspension of the HCl salt of the cationic lipid at its CMC (critical micelle concentration) or a concentration of up to about 2-fold above the lipid's CMC to obtain a cationic lipid suspension; (b) measuring the pH of the cationic lipid suspension; (c) adding 0.1 equivalent of a NaOH solution in water and mixing the NaOH solution into the cationic lipid suspension; (d) measuring the pH of the suspension of step (c) to obtain a pH value; (e) repeating steps (c) and (d) until one has added 1.0 equivalents of the NaOH solution and obtained the pH value at completion of each repetition of step (d); (f) plotting each pH value obtained from each repetition of step (d) versus the number of equivalents of added NaOH; and (g) determining the pKa of the cationic lipid using an inflection point of the pH versus equivalents of added NaOH curve.

In other embodiments, the invention provides methods to deliver therapeutic agents systemically to an animal, e.g., non-human primate, rodent or to a human. Complexes containing the invention lipids and a therapeutic agent are introduced into the host, usually by injection into a vein or by subcutaneous injection. The complexes, especially when the complexes are formulated without a colipid, can efficiently deliver the therapeutic agent into cells or cell cytoplasm in various tissues or organs such as the lung, spleen or liver, depending on the injection site.

DETAILED DESCRIPTION OF THE INVENTION

As used herein, and unless modified by the immediate context:

The terms alkyl and alkenyl mean linear, branched, and cyclic hydrocarbons. Usually, alkyl groups will be linear or unbranched. Alkyl includes by way of example and not limitation methyl, ethyl, propyl, cyclopropyl, cyclobutyl, isopropyl, n-, sec-, iso- and tert-butyl, pentyl, isopentyl, 1-methylbutyl, 1-ethylpropyl, neopentyl, and t-pentyl. Ranges of carbon atoms for a given group, such as alkyl ($C_{1-4}$), mean alkyl groups having 1, 2, 3 or 4 carbon atoms are present at the indicated position. Similarly, a group specified as alkyl ($C_{1-8}$), means alkyl groups having 1, 2, 3, 4, 5, 6, 7 or 8 carbon atoms are present at the indicated position. Thus, for example, the terms alkyl and alkyl ($C_{1-8}$) includes by way of example and not limitation n-hexyl, cyclohexyl and positional and stereoisomers of n-hexyl.

Alkenyl means branched, normal or cyclic hydrocarbons containing at least 1 (generally 1, 2 or 3, usually 1) cis or trans oriented conjugated or unconjugated double bond, including by way of example and not limitation allyl, ethenyl, propenyl, isopropenyl, 1-, 2- and 3-butenyl, 1- and 2-isobutenyl and the like. Usually alkenyl groups will be linear or unbranched and will typically contain about 10–26 carbon atoms, usually about 10–22.

Groups such as heteroaryl having 1, 2, or 3 ring O, N or S atoms, do not include obviously unstable combinations such as peroxides or disulfides.

The term pKa, as applied to the invention lipids, means a pKa of a moiety, e.g., an alkyl amine, present in an invention lipid. The pKa is measured in water at or above the lipid's CMC and in the absence of an anionic, polyanionic or other compound.

Invention Embodiments

The invention is directed to cationic lipids capable of forming micelles or bilayer structures under aqueous or physiological conditions, e.g., in the bloodstream, lymph fluid or extracellular fluid of a mammal or in tissue culture medium for mammalian cells. The cationic lipids comprise a charged domain of structure $\underline{A}$ linked to a lipophilic domain [—N($R_2$)]. The lipids of the invention usually have 1, 2, or 3, usually 1 or 2, moieties in the charged domain that have a pKa of about 6.0–7.5, usually about 6.3–7.2, in aqueous media with a lipid concentration at or above the lipid's CMC. Structure $\underline{A}$ lipids having a $W^1$ cationic group with a pKa of about 6.0–7.5 will have a charge of about +0.5–1.0 at a pH range of about 5.0–7.5. The invention lipids optionally contain 1 or 2, usually 1, charged moieties having a pKa of about 7.5–10, usually about 7.5–8.5. The charged moieties on structure $\underline{A}$ lipids are usually organic bases such as amines or substituted amines. Workers have described means to measure pKa values of organic bases and means to estimate the effects of different organic groups located near organic bases on a given molecule (see, e.g., Perrin et al., *pKa Prediction for Organic Acids and Bases,* Chapman and Hall, London, 1981, Smart et al., *J. Am. Chem. Soc.,* 118:2283–2284, 1996). The pKa of amines and substituted amines present on lipids in micelles, bilayers or other lipid complexes is generally decreased by about 1 pKa unit compared to the pKa of the amines and substituted amines in solutions that do not contain complexes, i.e., below the CMC.

An aspect of the invention lipids is the presence of a moiety that has a pKa of about 6.0–7.5, which have a charge of about +0.5–1.0 at a pH range of about 5.0–7.5. These moieties typically are of structure $\underline{B}$, $\underline{C}$ or $\underline{D}$, but can also have other structures such as those defined for the variable $W^1$. The inventors believe that the pKa of these groups when present in lipids in liposomes or other complexes is about 6.0–7.5. At mildly acidic pH values found in endosomes, the net charge on $\underline{B}$, $\underline{C}$ or $\underline{D}$ increases to about 0.9 or more from a lower net positive charge. Without intending to be bound by any theory, the inventors believe that an increased charge of the invention lipids at low physiological pH values, i.e. in endosomes at pH values of about 5.0–6.0, contributes to the capacity of the invention lipids to deliver anionic compounds to cell cytoplasm in vivo. An increased fusogenic capacity of the invention lipids may result from an enhanced interaction between the invention cationic lipid, which typically carries a charge of about +1, +2 or more with anionic lipids at the inner surface of endosomes. A sufficient interaction between the invention cationic lipids and anionic lipids in the endosome membrane may trigger or facilitate fusion between the two lipid-containing structures which results in transfer of therapeutic agents, anionic compounds or polyanionic compounds into the cell cytoplasm.

The invention cationic lipids have a lipophilic domain that facilitates forming lipid complexes or aggregates in aqueous solutions. To posess sufficient aqueous solubility, the lipophilic domain typically consists of one or more lipophilic moieties, more typically 1, 2 or 3 moieties, usually 2, containing at least about 10 linked carbon atoms, typically about 10–50 linked carbon atoms, usually about 10–22 linked carbon atoms. When the lipophilic domain comprises a single lipophilic moiety, the moiety will typically comprise at least about 20 carbon atoms, usually about 20–40 carbon atoms. The lipophilicity of the lipophilic domain or the R groups will be such that, when the cationic lipid is present in an aqueous solution, it will be sufficiently soluble to allow formation of lipid complexes in the presence or absence of a second compound. Exemplary lipophilic R groups include (1) alkanes including $C_{10-22}$ alkanes, (2) alkenes usually having 1, 2 or 3 double bonds, including $C_{10-22}$ alkenes with 1, 2 or 3 double bonds, (3) steroids such as pregnenolone, testosterone, estrone and aldosterone, (4) cholesterol and related compounds such as desmosterol, 7-dehydrocholesterol and cholestanol, (5) diacyl and triacylglycerols including ceramides, phosphatidylethanolamines, phosphatidylcholines, cardiolipins, sphingomyelins, and glucocerebrosides and (6) lipophilic structures previously used in cationic lipids, see, e.g., Felgner et al. *J. Biol. Chem.*269:2550–2561, 1994, Lewis et al. *Proc. Natl. Acad. Sci.* (U.S.A.) 93:3176–3181, 1996, Nabel et al. *Proc. Natl. Acad. Sci.* (U.S.A.) 90:11307, 1993, and other citations herein.

Individual invention cationic lipids optionally are tested for their capacity to form a lipid complex or aggregate, without a polyanion or other compound being present, in an aqueous solution by standard methods used to determine the lipid's CMC (critical micelle concentration). At the CMC, a lipid begins to form aggregates of lipid molecules, often micelles. At lipid concentrations above the CMC, the type of aggregates or structures the lipids form often differs from those found at the CMC. Lipid aggregates or structures one finds at or above the lipid's CMC include micelles, bilayers, colloidal aggregates, small unilamellar vesicles, large unilamellar vesicles and multilamellar vesicles of varying sizes. Lipids that are insufficiently soluble to reach a concentration that is at or above the lipid's CMC will be unsuitable for preparing complexes with polyanionic compounds, and these relatively insoluble lipids are not included within the scope of the invention lipids. One designs a lipid with sufficient water solubility by roughly matching the degree of hydrophobicity of the hydrophobic domain with the net charge of the charged domain at physiological pH (about 5.0–7.4). Thus, when the hydrophobic domain contains a relatively high number of carbon atoms, e.g., about 40–70, the charged domain will generally have a charge of about +2–4. When the hydrophobic domain contains a lower number of carbon atoms, e.g., about 20–40, the charged domain will generally have a charge of about +0.4–2.

The invention cationic lipids contain lipophilic and charged domains. The charged domain will contain one or more, usually 1 or 2, moieties that have a pKa of about 6.0–7.5, typically 6.3–7.2. The invention lipids optionally contain one or more, usually 1, 2 or 3, additional charged moieties, e.g., an alkyl amine ($CH_2NH_2$) or substituted alkyl amine ($CH_2NHX$ where X is any of a broad range of substituents that are not strongly electron withdrawing), that have a pKa of at least about 9.0.

Exemplary R have the structures $-(CH_2)_{19}CH_3$, $-(CH_2)_{18}CH_3$, $-(CH_2)_{17}CH_3$, $-(CH_2)_{16}CH_3$, $-(CH_2)_{15}CH_3$, $-(CH_2)_{14}CH_3$, $-(CH_2)_{13}CH_3$, $-(CH_2)_{12}CH_3$, $-(CH_2)_{11}CH_3$, $-(CH_2)_{10}CH_3$, $-(CH_2)_9CH_3$, $-(CH_2)_5CH=CH(CH_2)_7CH_3$, $-(CH_2)_8CH=CH(CH_2)_5CH_3$, $-(CH_2)_7CH=CH(CH_2)_7CH_3$, and $-(CH_2)_8CH=CH(CH_2)_7CH_3$. The alkenyl species are in a cis or trans configuration at the double bond, usually cis. In general, each $R^1$ on a given molecule will have the same structure, although they may be different. $R^1$ can comprise, for example, alkyl ($C_{12-16}$) groups. $R^1$ is typically a normal alkane such as n-$C_{18}H_{37}$, n-$C_{16}H_{33}$, or n-$C_{14}H_{29}$.

When R is a cholesterol moiety, R in cationic lipids of structure A has the structure:

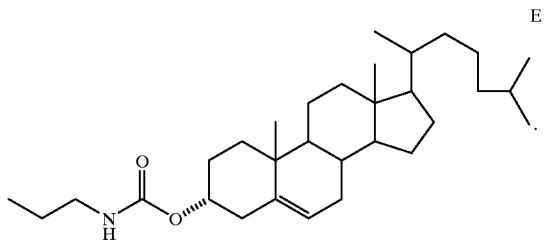

Structure A compounds generally have hydrogen at $R^3$, $R^4$, and $R^5$, although they are typically an amine protecting group in intermediates used to synthesize fully deprotected structure A cationic lipids. When $R^3$, $R^4$ or $R^5$ is a protecting group then any conventional protecting group is usually useful. See for example, Green et al. (infra) and further discussion in the schemes. When $R^3$ or $R^4$ is alkyl, they are generally methyl, ethyl or propyl.

Structure A compounds typically have a single B, C or D moiety that is present in the molecule, usually B. Structure A compounds include species where one of m and n is 0 and the other is 1, but they are typically species where m and n are both 0.

Compositions containing compounds of structure A are usually free of otherwise identical compounds which do not contain any amino protecting substituents. Invention embodiments contain partially deprotected derivatives of the protected structure A compounds. Both partially and fully protected compounds are useful as synthetic intermediates in the preparation of fully deprotected compounds. In other embodiments, the structure A compounds contain less than about 1%, 0.5% or 0.1% by weight of such unsubstituted analogs in relation to the weight of the substituted congener.

The variable m generally is 0, the variable n generally is 0, and when $R^3$, $R^4$ or $R^5$ is $-CH_2-(CF_2)_p-CF_3$, the variable p generally is 0, 1 or 2.

The compounds of the invention include enriched or resolved optical isomers at any or all asymmetric atoms. For example, the invention provides the chiral centers in structure A compounds as the chiral isomers or racemic mixtures. Both racemic and diasteromeric mixtures, as well as the individual optical isomers isolated or synthesized, substantially free of their enantiomeric or diasteromeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material. Methods and theories used to obtain enriched and resolved isomers have been described (see for example, J. Jacques et al, "Enantiomers, Racemates and Resolutions." Kreiger, Malabar, Fla., 1991).

Specific Exemplary Embodiments

Specific embodiments of the structure A lipids include those described in Table 1. Table 1 shows structure A lipids having specific R, $R^1$, $R^2$ and $R^3$ substituents. The designations A3, A4, A6 and A8 mean an alkyl group having 3, 4, 6 and 8 carbon atoms respectively. These designations include all positional isomers of these alkyl groups, e.g., linear, branched and cyclic isomers.

TABLE 1

| R | $R^1$ |
|---|---|
| 1. $-(CH_2)_9CH_3$ | 1. B |
| 2. $-(CH_2)_{10}CH_3$ | 2. C |
| 3. $-(CH_2)_{11}CH_3$ | 3. D |
| 4. $-(CH_2)_{12}CH_3$ | 4. $-H$ |
| 5. $-(CH_2)_{13}CH_3$ | 5. $-(CH_2)_4NH_2$ |
| 6. $-(CH_2)_{14}CH_3$ | 6. $-(CH_2)_4N(CH_2CF_3)_2$ |
| 7. $-(CH_2)_{15}CH_3$ | 7. $-CH_2NH_2$ |
| 8. $-(CH_2)_{16}CH_3$ | 8. $-CH_2N(CH_2CH_3)_2$ |
| 9. $-(CH_2)_{17}CH_3$ | 9. $-CH_2N(A3)_2$ |

| $R^2$ | $R^3$ |
|---|---|
| 1. B | 1. $-H$ |
| 2. C | 2. $-CH_3$ |
| 3. D | 3. $-CH_2CH_3$ |
| 4. $-H$ | 4. $-A3$ |
| 5. $-(CH_2)_4NH_2$ | 5. $-A4$ |
| 6. $-(CH_2)_4N(CH_2CF_3)_2$ | 6. $-CH_2-CF_3$ |
| 7. $-CH_2NH_2$ | 7. $-CH_2-CF_2-CF_3$ |

Table 1 assigns a number to each R, $R^1$, $R^2$ and $R^3$ substituent shown in the Table. The convention $R.R^1.R^2.R^3$ names or defines individual structure A compounds where m and n are both 0 and the number assigned to a listed substituent corresponds to the structure in Table 1. Thus, a structure $\underline{A}$ compound named 5.1.4.2 has the structure $\underline{A}$ where both m and n are 0, both R are —$(CH_2)_{13}CH_3$, $R^1$ is $\underline{B}$, $R^2$ is hydrogen and both $R^3$ are —$CH_3$. A structure $\underline{A}$ compound named 7.4.1.4 has the structure $\underline{A}$ where both m and n are 0, both R are —$(CH_2)_{15}CH_3$, $R^1$ is hydrogen, $R^2$ is $\underline{B}$ and both $R^3$ are —A3 (alkyl having 3 carbon atoms). Table 2 lists exemplary invention compounds of structure $\underline{A}$ according to this convention.

TABLE 2

| | | | | | | | | | | | | |
|---|---|---|---|---|---|---|---|---|---|---|---|---|
| 1.1.1.1 | 1.1.1.2 | 1.1.1.3 | 1.1.1.4 | 1.1.1.5 | 1.1.1.6 | 1.1.1.7 | 1.2.1.1 | 1.2.1.2 | 1.2.1.3 | 1.2.1.4 | 1.2.1.5 | 1.2.1.6 |
| 1.2.1.7 | 1.3.1.1 | 1.3.1.2 | 1.3.1.3 | 1.3.1.4 | 1.3.1.5 | 1.3.1.6 | 1.3.1.7 | 1.4.1.1 | 1.4.1.2 | 1.4.1.3 | 1.4.1.4 | 1.4.1.5 |
| 1.4.1.6 | 1.4.1.7 | 1.5.1.1 | 1.5.1.2 | 1.5.1.3 | 1.5.1.4 | 1.5.1.5 | 1.5.1.6 | 1.5.1.7 | 1.6.1.1 | 1.6.1.2 | 1.6.1.3 | 1.6.1.4 |
| 1.6.4.5 | 1.6.1.6 | 1.6.1.7 | 1.7.1.1 | 1.7.1.2 | 1.7.1.3 | 1.7.1.4 | 1.7.1.5 | 1.7.1.6 | 1.7.1.7 | 1.8.1.1 | 1.8.1.2 | 1.8.1.3 |
| 1.8.1.4 | 1.8.1.5 | 1.8.1.6 | 1.8.1.7 | 1.9.1.1 | 1.9.1.2 | 1.9.1.3 | 1.9.1.4 | 1.9.1.5 | 1.9.1.6 | 1.9.1.7 | 2.1.1.1 | 2.1.1.2 |
| 2.1.1.3 | 2.1.1.4 | 2.1.1.5 | 2.1.1.6 | 2.1.1.7 | 2.2.1.1 | 2.2.1.2 | 2.2.1.3 | 2.2.1.4 | 2.2.1.5 | 2.2.1.6 | 2.2.1.7 | 2.3.1.1 |
| 2.3.1.2 | 2.3.1.3 | 2.3.1.4 | 2.3.1.5 | 2.3.1.6 | 2.3.1.7 | 2.4.1.1 | 2.4.1.2 | 2.4.1.3 | 2.4.1.4 | 2.4.1.5 | 2.4.1.6 | 2.4.1.7 |
| 2.5.1.1 | 2.5.1.2 | 2.5.1.3 | 2.5.1.4 | 2.5.1.5 | 2.5.1.6 | 2.5.1.7 | 2.6.1.1 | 2.6.1.2 | 2.6.1.3 | 2.6.1.4 | 2.6.1.5 | 2.6.1.6 |
| 2.6.1.7 | 2.7.1.1 | 2.7.1.2 | 2.7.1.3 | 2.7.1.4 | 2.7.1.5 | 2.7.1.6 | 2.7.1.7 | 2.8.1.1 | 2.8.1.2 | 2.8.1.3 | 2.8.1.4 | 2.8.1.5 |
| 2.8.1.6 | 2.8.1.7 | 2.9.1.1 | 2.9.1.2 | 2.9.1.3 | 2.9.1.4 | 2.9.1.5 | 2.9.1.6 | 2.9.1.7 | 3.1.1.1 | 3.1.1.2 | 3.1.1.3 | 3.1.1.4 |
| 3.1.1.5 | 3.1.1.6 | 3.1.1.7 | 3.2.1.1 | 3.2.1.2 | 3.2.1.3 | 3.2.1.4 | 3.2.1.5 | 3.2.1.6 | 3.2.1.7 | 3.3.1.1 | 3.3.1.2 | 3.3.1.3 |
| 3.3.1.4 | 3.3.1.5 | 3.3.1.6 | 3.3.1.7 | 3.4.1.1 | 3.4.1.2 | 3.4.1.3 | 3.4.1.4 | 3.4.1.5 | 3.4.1.6 | 3.4.1.7 | 3.5.1.1 | 3.5.1.2 |
| 3.5.1.3 | 3.5.1.4 | 3.5.1.5 | 3.5.1.6 | 3.5.1.7 | 3.6.1.1 | 3.6.1.2 | 3.6.1.3 | 3.6.1.4 | 3.6.1.5 | 3.6.1.6 | 3.6.1.7 | 3.7.1.1 |
| 3.7.1.2 | 3.7.1.3 | 3.7.1.4 | 3.7.1.5 | 3.7.1.6 | 3.7.1.7 | 3.8.1.1 | 3.8.1.2 | 3.8.1.3 | 3.8.1.4 | 3.8.1.5 | 3.8.1.6 | 3.8.1.7 |
| 3.9.1.1 | 3.9.1.2 | 3.9.1.3 | 3.9.1.4 | 3.9.1.5 | 3.9.1.6 | 3.9.1.7 | 4.1.1.4 | 4.1.1.2 | 4.1.1.3 | 4.1.1.4 | 4.1.1.5 | 4.1.1.6 |
| 4.1.1.7 | 4.2.1.1 | 4.2.1.2 | 4.2.1.3 | 4.2.1.4 | 4.2.1.5 | 4.2.1.6 | 4.2.1.7 | 4.3.1.1 | 4.3.1.2 | 4.3.1.3 | 4.3.1.4 | 4.3.1.5 |
| 4.3.1.6 | 4.3.1.7 | 4.4.1.1 | 4.4.1.2 | 4.4.1.3 | 4.4.1.4 | 4.4.1.5 | 4.4.1.6 | 4.4.1.7 | 4.5.1.1 | 4.5.1.2 | 4.5.1.3 | 4.5.1.4 |
| 4.5.1.5 | 4.5.1.6 | 4.5.1.7 | 4.6.1.1 | 4.6.1.2 | 4.6.1.3 | 4.6.1.4 | 4.6.1.5 | 4.6.1.6 | 4.6.1.7 | 4.7.1.1 | 4.7.1.2 | 4.7.1.3 |
| 4.7.1.4 | 4.7.1.5 | 4.7.1.6 | 4.7.1.7 | 4.8.1.1 | 4.8.1.2 | 4.8.1.3 | 4.8.1.4 | 4.8.1.5 | 4.8.1.6 | 4.8.1.7 | 4.9.1.1 | 4.9.1.2 |
| 4.9.1.3 | 4.9.1.4 | 4.9.1.5 | 4.9.1.6 | 4.9.1.7 | 5.1.1.1 | 5.1.1.2 | 5.1.1.3 | 5.1.1.4 | 5.1.1.5 | 5.1.1.6 | 5.1.1.7 | 5.1.2.1 |
| 5.2.1.2 | 5.2.1.3 | 5.2.1.4 | 5.2.1.5 | 5.2.1.6 | 5.2.1.7 | 5.3.1.1 | 5.3.1.2 | 5.3.1.3 | 5.3.1.4 | 5.3.1.5 | 5.3.1.6 | 5.3.1.7 |
| 5.4.1.1 | 5.4.1.2 | 5.4.1.3 | 5.4.1.4 | S.4.1.5 | 5.4.1.6 | 5.4.1.7 | 5.5.1.1 | 5.5.1.2 | 5.5.1.3 | 5.5.1.4 | 5.5.1.5 | 5.5.1.6 |
| 5.5.1.7 | 5.6.1.1 | 5.6.1.2 | 5.6.1.3 | 5.6.1.4 | 5.6.1.5 | 5.6.1.6 | 5.6.1.7 | 5.7.1.1 | 5.7.1.2 | 5.7.1.3 | 5.7.1.4 | 5.7.1.5 |
| 5.7.1.6 | 5.7.1.7 | 5.8.1.1 | 5.8.1.2 | 5.8.1.3 | 5.8.1.4 | 5.8.1.5 | 5.8.1.6 | 5.8.1.7 | 5.9.1.1 | 5.9.1.2 | 5.9.1.3 | 5.9.1.4 |
| 5.9.1.5 | 5.9.1.6 | 5.9.1.7 | 6.1.1.1 | 6.1.1.2 | 6.1.1.3 | 6.1.1.4 | 6.1.1.5 | 6.1.1.6 | 6.1.1.7 | 6.2.1.1 | 6.2.1.2 | 6.2.1.3 |
| 6.2.1.4 | 6.2.1.5 | 6.2.1.6 | 6.2.1.7 | 6.3.1.1 | 6.3.1.2 | 6.3.1.3 | 6.3.1.4 | 6.3.1.5 | 6.3.1.6 | 6.3.1.7 | 6.4.1.1 | 6.4.1.2 |
| 6.4.1.3 | 6.4.1.4 | 6.4.1.5 | 6.4.1.6 | 6.4.1.7 | 6.5.1.1 | 6.5.1.2 | 6.5.1.3 | 6.5.1.4 | 6.5.1.5 | 6.5.1.6 | 6.5.1.7 | 6.6.1.1 |
| 6.6.1.2 | 6.6.1.3 | 6.6.1.4 | 6.6.1.5 | 6.6.1.6 | 6.6.1.7 | 6.7.1.1 | 6.7.1.2 | 6.7.1.3 | 6.7.1.4 | 6.7.1.5 | 6.7.1.6 | 6.7.1.7 |
| 6.8.1.1 | 6.8.1.2 | 6.8.1.3 | 6.8.1.4 | 6.8.1.5 | 6.8.1.6 | 6.8.1.7 | 6.9.1.1 | 6.9.1.2 | 6.9.1.3 | 6.9.1.4 | 6.9.1.5 | 6.9.1.6 |
| 6.9.1.7 | 7.1.1.1 | 7.1.1.2 | 7.1.1.3 | 7.1.1.4 | 7.1.1.5 | 7.1.1.6 | 7.1.1.7 | 7.2.1.1 | 7.2.1.2 | 7.2.1.3 | 7.2.1.4 | 7.2.1.5 |
| 7.2.1.6 | 7.2.1.7 | 7.3.1.1 | 7.3.1.2 | 7.3.1.3 | 7.3.1.4 | 7.3.1.5 | 7.3.1.6 | 7.3.1.7 | 7.4.1.1 | 7.4.1.2 | 7.4.1.3 | 7.4.1.4 |
| 7.4.1.5 | 7.4.1.6 | 7.4.1.7 | 7.5.1.1 | 7.5.1.2 | 7.5.1.3 | 7.5.1.4 | 7.5.1.5 | 7.5.1.6 | 7.5.1.7 | 7.6.1.1 | 7.6.1.2 | 7.6.1.3 |
| 7.6.1.4 | 7.6.1.5 | 7.6.1.6 | 7.6.1.7 | 7.7.1.1 | 7.7.1.2 | 7.7.1.3 | 7.7.1.4 | 7.7.1.5 | 7.7.1.6 | 7.7.1.7 | 7.8.1.1 | 7.8.1.2 |
| 7.8.1.3 | 7.8.1.4 | 7.8.1.5 | 7.8.1.6 | 7.8.1.7 | 7.9.1.1 | 7.9.1.2 | 7.9.1.3 | 7.9.1.4 | 7.9.1.5 | 7.9.1.6 | 7.9.1.7 | 8.1.1.1 |
| 8.1.1.2 | 8.1.1.3 | 8.1.1.4 | 8.1.1.5 | 8.1.1.6 | 8.1.1.7 | 8.2.1.1 | 8.2.1.2 | 8.2.1.3 | 8.2.1.4 | 8.2.1.5 | 8.2.1.6 | 8.2.1.7 |
| 8.3.1.1 | 8.3.1.2 | 8.3.1.3 | 8.3.1.4 | 8.3.1.5 | 8.3.1.6 | 8.3.1.7 | 8.4.1.1 | 8.4.1.2 | 8.4.1.3 | 8.4.1.4 | 8.4.1.5 | 8.4.1.6 |
| 8.4.1.7 | 8.5.1.1 | 8.5.1.2 | 8.5.1.3 | 8.5.1.4 | 8.5.1.5 | 8.5.1.6 | 8.5.1.7 | 8.6.1.1 | 8.6.1.2 | 8.6.1.3 | 8.6.1.4 | 8.6.1.5 |
| 8.6.1.6 | 8.6.1.7 | 8.7.1.1 | 8.7.1.2 | 8.7.1.3 | 8.7.1.4 | 8.7.1.5 | 8.7.1.6 | 8.7.1.7 | 8.8.1.1 | 8.8.1.2 | 8.8.1.3 | 8.8.1.4 |
| 8.8.1.5 | 8.8.1.6 | 8.8.1.7 | 8.9.1.1 | 8.9.1.2 | 8.9.1.3 | 8.9.1.4 | 8.9.1.5 | 8.9.1.6 | 8.9.1.7 | 9.1.1.1 | 9.1.1.2 | 9.1.1.3 |
| 9.1.1.4 | 9.1.1.5 | 9.1.1.6 | 9.1.1.7 | 9.2.1.1 | 9.2.1.2 | 9.2.1.3 | 9.2.1.4 | 9.2.1.5 | 9.2.1.6 | 9.2.1.7 | 9.3.1.1 | 9.3.1.2 |
| 9.3.1.3 | 9.3.1.4 | 9.3.1.5 | 9.3.1.6 | 9.3.1.7 | 9.4.1.1 | 9.4.1.2 | 9.4.1.3 | 9.4.1.4 | 9.4.1.5 | 9.4.1.6 | 9.4.1.7 | 9.5.1.1 |
| 9.5.1.2 | 9.5.1.3 | 9.5.1.4 | 9.5.1.5 | 9.5.1.6 | 9.5.1.7 | 9.6.1.1 | 9.6.1.2 | 9.6.1.3 | 9.6.1.4 | 9.6.1.5 | 9.6.1.6 | 9.6.1.7 |
| 9.7.1.1 | 9.7.1.2 | 9.7.1.3 | 9.7.1.4 | 9.7.1.5 | 9.7.1.6 | 9.7.1.7 | 9.8.1.1 | 9.8.1.2 | 9.8.1.3 | 9.8.1.4 | 9.8.1.5 | 9.8.1.6 |
| 9.8.1.7 | 9.9.1.1 | 9.9.1.2 | 9.9.1.3 | 9.9.1.4 | 9.9.1.5 | 9.9.1.6 | 9.9.1.7 | 1.1.2.1 | 1.1.2.2 | 1.1.2.3 | 1.1.2.4 | 1.1.2.5 |
| 1.1.2.6 | 1.1.2.7 | 1.2.2.1 | 1.2.2.2 | 1.2.2.3 | 1.2.2.4 | 1.2.2.5 | 1.2.2.6 | 1.2.2.7 | 1.3.2.1 | 1.3.2.2 | 1.3.2.3 | 1.3.2.4 |
| 1.3.2.5 | 1.3.2.6 | 1.3.2.7 | 1.4.2.1 | 1.4.2.2 | 1.4.2.3 | 1.4.2.4 | 1.4.2.5 | 1.4.2.6 | 1.4.2.7 | 1.5.2.1 | 1.5.2.2 | 1.5.2.3 |
| 1.5.2.4 | 1.5.2.5 | 1.5.2.6 | 1.5.2.7 | 1.6.2.1 | 1.6.2.2 | 1.6.2.3 | 1.6.2.4 | 1.6.2.5 | 1.6.2.6 | 1.6.2.7 | 1.7.2.1 | 1.7.2.2 |
| 1.7.2.3 | 1.7.2.4 | 1.7.2.5 | 1.7.2.6 | 1.7.2.7 | 1.8.2.1 | 1.8.2.2 | 1.8.2.3 | 1.8.2.4 | 1.8.2.5 | 1.8.2.6 | 1.8.2.7 | 1.9.2.1 |
| 1.9.2.2 | 1.9.2.3 | 1.9.2.4 | 1.9.2.5 | 1.9.2.6 | 1.9.2.7 | 2.1.2.1 | 2.1.2.2 | 2.1.2.3 | 2.1.2.4 | 2.1.2.5 | 2.1.2.6 | 2.1.2.7 |
| 2.2.2.1 | 2.2.2.2 | 2.2.2.3 | 2.2.2.4 | 2.2.2.5 | 2.2.2.6 | 2.2.2.7 | 2.3.2.1 | 2.3.2.2 | 2.3.2.3 | 2.3.2.4 | 2.3.2.5 | 2.3.2.6 |
| 2.3.2.7 | 2.4.2.1 | 2.4.2.2 | 2.4.2.3 | 2.4.2.4 | 2.4.2.5 | 2.4.2.6 | 2.4.2.7 | 2.5.2.1 | 2.5.2.2 | 2.5.2.3 | 2.5.2.4 | 2.5.2.5 |
| 2.5.2.6 | 2.5.2.7 | 2.6.2.1 | 2.6.2.2 | 2.6.2.3 | 2.6.2.4 | 2.6.2.5 | 2.6.2.6 | 2.6.2.7 | 2.7.2.1 | 2.7.2.2 | 2.7.2.3 | 2.7.2.4 |
| 2.7.2.5 | 2.7.2.6 | 2.7.2.7 | 2.8.2.1 | 2.8.2.2 | 2.8.2.3 | 2.8.2.4 | 2.8.2.5 | 2.8.2.6 | 2.8.2.7 | 2.9.2.1 | 2.9.2.2 | 2.9.2.3 |
| 2.9.2.4 | 2.9.2.5 | 2.9.2.6 | 2.9.2.7 | 3.1.2.1 | 3.1.2.2 | 3.1.2.3 | 3.1.2.4 | 3.1.2.5 | 3.1.2.6 | 3.1.2.7 | 3.2.2.1 | 3.2.2.2 |
| 3.2.2.3 | 3.2.2.4 | 3.2.2.5 | 3.2.2.6 | 3.2.2.7 | 3.3.2.1 | 3.3.2.2 | 3.3.2.3 | 3.3.2.4 | 3.3.2.5 | 3.3.2.6 | 3.3.2.7 | 3.4.2.1 |
| 3.4.2.2 | 3.4.2.3 | 3.4.2.4 | 3.4.2.5 | 3.4.2.6 | 3.4.2.7 | 3.5.2.1 | 3.5.2.2 | 3.5.2.3 | 3.5.2.4 | 3.5.2.5 | 3.5.2.6 | 3.5.2.7 |
| 3.6.2.1 | 3.6.2.2 | 3.6.2.3 | 3.6.2.4 | 3.6.2.5 | 3.6.2.6 | 3.6.2.7 | 3.7.2.1 | 3.7.2.2 | 3.7.2.3 | 3.7.2.4 | 3.7.2.5 | 3.7.2.6 |
| 3.7.2.7 | 3.8.2.1 | 3.8.2.2 | 3.8.2.3 | 3.8.2.4 | 3.8.2.5 | 3.8.2.6 | 3.8.2.7 | 3.9.2.1 | 3.9.2.2 | 3.9.2.3 | 3.9.2.4 | 3.9.2.5 |
| 3.9.2.6 | 3.9.2.7 | 4.1.2.1 | 4.1.2.2 | 4.1.2.3 | 4.1.2.4 | 4.1.2.5 | 4.1.2.6 | 4.4.2.7 | 4.2.2.1 | 4.2.2.2 | 4.2.2.3 | 4.2.2.4 |
| 4.2.2.5 | 4.2.2.6 | 4.2.2.7 | 4.3.2.1 | 4.3.2.2 | 4.3.2.3 | 4.3.2.4 | 4.3.2.5 | 4.3.2.6 | 4.3.2.7 | 4.4.2.1 | 4.4.2.2 | 4.4.2.3 |
| 4.4.2.4 | 4.4.2.5 | 4.4.2.6 | 4.4.2.7 | 4.5.2.1 | 4.5.2.2 | 4.5.2.3 | 4.5.2.4 | 4.5.2.5 | 4.5.2.6 | 4.5.2.7 | 4.6.2.1 | 4.6.2.2 |
| 4.6.2.3 | 4.6.2.4 | 4.6.2.5 | 4.6.2.6 | 4.6.2.7 | 4.7.2.1 | 4.7.2.2 | 4.7.2.3 | 4.7.2.4 | 4.7.2.5 | 4.7.2.6 | 4.7.2.7 | 4.8.2.1 |
| 4.8.2.2 | 4.8.2.3 | 4.8.2.4 | 4.8.2.5 | 4.8.2.6 | 4.8.2.7 | 4.9.2.1 | 4.9.2.2 | 4.9.2.3 | 4.9.2.4 | 4.9.2.5 | 4.9.2.6 | 4.9.2.7 |
| 5.1.2.1 | 5.1.2.2 | 5.1.2.3 | 5.1.2.4 | 5.1.2.5 | 5.1.2.6 | 5.1.2.7 | 5.2.2.1 | 5.2.2.2 | 5.2.2.3 | 5.2.2.4 | 5.2.2.5 | 5.2.2.6 |
| 5.2.2.7 | 5.3.2.1 | 5.3.2.2 | 5.3.2.3 | 5.3.2.4 | 5.3.2.5 | 5.3.2.6 | 5.3.2.7 | 5.4.2.1 | 5.4.2.2 | 5.4.2.3 | 5.4.2.4 | 5.4.2.5 |
| 5.4.2.6 | 5.4.2.7 | 5.5.2.1 | 5.5.2.2 | 5.5.2.3 | 5.5.2.4 | 5.5.2.5 | 5.5.2.6 | 5.5.2.7 | 5.6.2.1 | 5.6.2.2 | 5.6.2.3 | 5.6.2.4 |
| 5.6.2.5 | 5.6.2.6 | 5.6.2.7 | 5.7.2.1 | 5.7.2.2 | 5.7.2.3 | 5.7.2.4 | 5.7.2.5 | 5.7.2.6 | 5.7.2.7 | 5.8.2.1 | 5.8.2.2 | 5.8.2.3 |
| 5.8.2.4 | 5.8.2.5 | 5.8.2.6 | 5.8.2.7 | 5.9.2.1 | 5.9.2.2 | 5.9.2.3 | 5.9.2.4 | 5.9.2.5 | 5.9.2.6 | 5.9.2.7 | 6.1.2.1 | 6.1.2.2 |
| 6.1.2.3 | 6.1.2.4 | 6.1.2.5 | 6.1.2.6 | 6.1.2.7 | 6.2.2.1 | 6.2.2.2 | 6.2.2.3 | 6.2.2.4 | 6.2.2.5 | 6.2.2.6 | 6.2.2.7 | 6.3.2.1 |
| 6.3.2.2 | 6.3.2.3 | 6.3.2.4 | 6.3.2.5 | 6.3.2.6 | 6.3.2.7 | 6.4.2.1 | 6.4.2.2 | 6.4.2.3 | 6.4.2.4 | 6.4.2.5 | 6.4.2.6 | 6.4.2.7 |
| 6.5.2.1 | 6.5.2.2 | 6.5.2.3 | 6.5.2.4 | 6.5.2.5 | 6.5.2.6 | 6.5.2.7 | 6.6.2.1 | 6.6.2.2 | 6.6.2.3 | 6.6.2.4 | 6.6.2.5 | 6.6.2.6 |
| 6.6.2.7 | 6.7.2.1 | 6.7.2.2 | 6.7.2.3 | 6.7.2.4 | 6.7.2.5 | 6.7.2.6 | 6.7.2.7 | 6.8.2.1 | 6.8.2.2 | 6.8.2.3 | 6.8.2.4 | 6.8.2.5 |

TABLE 2-continued

| | | | | | | | | | | | |
|---|---|---|---|---|---|---|---|---|---|---|---|
| 6.8.2.6 | 6.8.2.7 | 6.9.2.1 | 6.9.2.2 | 6.9.2.3 | 6.9.2.4 | 6.9.2.5 | 6.9.2.6 | 6.9.2.7 | 7.1.2.1 | 7.1.2.2 | 7.1.2.3 | 7.1.2.4 |
| 7.1.2.5 | 7.1.2.6 | 7.1.2.7 | 7.2.2.1 | 7.2.2.2 | 7.2.2.3 | 7.2.2.4 | 7.2.2.5 | 7.2.2.6 | 7.2.2.7 | 7.3.2.1 | 7.3.2.2 | 7.3.2.3 |
| 7.3.2.4 | 7.3.2.5 | 7.3.2.6 | 7.3.2.7 | 7.4.2.1 | 7.4.2.2 | 7.4.2.3 | 7.4.2.4 | 7.4.2.5 | 7.4.2.6 | 7.4.2.7 | 7.5.2.1 | 7.5.2.2 |
| 7.5.2.3 | 7.5.2.4 | 7.5.2.5 | 7.5.2.6 | 7.5.2.7 | 7.6.2.1 | 7.6.2.2 | 7.6.2.3 | 7.6.2.4 | 7.6.2.5 | 7.6.2.6 | 7.6.2.7 | 7.7.2.1 |
| 7.7.2.2 | 7.7.2.3 | 7.7.2.4 | 7.7.2.5 | 7.7.2.6 | 7.7.2.7 | 7.8.2.1 | 7.8.2.2 | 7.8.2.3 | 7.8.2.4 | 7.8.2.5 | 7.8.2.6 | 7.8.2.7 |
| 7.9.2.1 | 7.9.2.2 | 7.9.2.3 | 7.9.2.4 | 7.9.2.5 | 7.9.2.6 | 7.9.2.7 | 8.1.2.1 | 8.1.2.2 | 8.1.2.3 | 8.1.2.4 | 8.1.2.5 | 8.1.2.6 |
| 8.1.2.7 | 8.2.2.1 | 8.2.2.2 | 8.2.2.3 | 8.2.2.4 | 8.2.2.5 | 8.2.2.6 | 8.2.2.7 | 8.3.2.1 | 8.3.2.2 | 8.3.2.3 | 8.3.2.4 | 8.3.2.5 |
| 8.3.2.6 | 8.3.2.7 | 8.4.2.1 | 8.4.2.2 | 8.4.2.3 | 8.4.2.4 | 8.4.2.5 | 8.4.2.6 | 8.4.2.7 | 8.5.2.1 | 8.5.2.2 | 8.5.2.3 | 8.5.2.4 |
| 8.5.2.5 | 8.5.2.6 | 8.5.2.7 | 8.6.2.1 | 8.6.2.2 | 8.6.2.3 | 8.6.2.4 | 8.6.2.5 | 8.6.2.6 | 8.6.2.7 | 8.7.2.1 | 8.7.2.2 | 8.7.2.3 |
| 8.7.2.4 | 8.7.2.5 | 8.7.2.6 | 8.7.2.7 | 8.8.2.1 | 8.8.2.2 | 8.8.2.3 | 8.8.2.4 | 8.8.2.5 | 8.8.2.6 | 8.8.2.7 | 8.9.2.1 | 8.9.2.2 |
| 8.9.2.3 | 8.9.2.4 | 8.9.2.5 | 8.9.2.6 | 8.9.2.7 | 9.1.2.1 | 9.1.2.2 | 9.1.2.3 | 9.1.2.4 | 9.1.2.5 | 9.1.2.6 | 9.1.2.7 | 9.2.2.1 |
| 9.2.2.2 | 9.2.2.3 | 9.2.2.4 | 9.2.2.5 | 9.2.2.6 | 9.2.2.7 | 9.3.2.1 | 9.3.2.2 | 9.3.2.3 | 9.3.2.4 | 9.3.2.5 | 9.3.2.6 | 9.3.2.7 |
| 9.4.2.1 | 9.4.2.2 | 9.4.2.3 | 9.4.2.4 | 9.4.2.5 | 9.4.2.6 | 9.4.2.7 | 9.5.2.1 | 9.5.2.2 | 9.5.2.3 | 9.5.2.4 | 9.5.2.5 | 9.5.2.6 |
| 9.5.2.7 | 9.6.2.1 | 9.6.2.2 | 9.6.2.3 | 9.6.2.4 | 9.6.2.5 | 9.6.2.6 | 9.6.2.7 | 9.7.2.1 | 9.7.2.2 | 9.7.2.3 | 9.7.2.4 | 9.7.2.5 |
| 9.7.2.6 | 9.7.2.7 | 9.8.2.1 | 9.8.2.2 | 9.8.2.3 | 9.8.2.4 | 9.8.2.5 | 9.8.2.6 | 9.9.2.1 | 9.9.2.2 | 9.9.2.3 | 9.9.2.4 |
| 9.9.2.5 | 9.9.2.6 | 9.9.2.7 | 1.1.3.1 | 1.1.3.2 | 1.1.3.3 | 1.1.3.4 | 1.1.3.5 | 1.1.3.6 | 1.1.3.7 | 1.2.3.1 | 1.2.3.2 | 1.2.3.3 |
| 1.2.3.4 | 1.2.3.5 | 1.2.3.6 | 1.2.3.7 | 1.3.3.1 | 1.3.3.2 | 1.3.3.3 | 1.3.3.4 | 1.3.3.5 | 1.3.3.6 | 1.3.3.7 | 1.4.3.1 | 1.4.3.2 |
| 1.4.3.3 | 1.4.3.4 | 1.4.3.5 | 1.4.3.6 | 1.4.3.7 | 1.5.3.1 | 1.5.3.2 | 1.5.3.3 | 1.5.3.4 | 1.5.3.5 | 1.5.3.6 | 1.5.3.7 | 1.6.3.1 |
| 1.6.3.2 | 1.6.3.3 | 1.6.3.4 | 1.6.3.5 | 1.6.3.6 | 1.6.3.7 | 1.7.3.1 | 1.7.3.2 | 1.7.3.3 | 1.7.3.4 | 1.7.3.5 | 1.7.3.6 | 1.7.3.7 |
| 1.8.3.1 | 1.8.3.2 | 1.8.3.3 | 1.8.3.4 | 1.8.3.5 | 1.8.3.6 | 1.8.3.7 | 1.9.3.1 | 1.9.3.2 | 1.9.3.3 | 1.9.3.4 | 1.9.3.5 | 1.9.3.6 |
| 1.9.3.7 | 2.1.3.1 | 2.1.3.2 | 2.1.3.3 | 2.1.3.4 | 2.1.3.5 | 2.1.3.6 | 2.1.3.7 | 2.2.3.1 | 2.2.3.2 | 2.2.3.3 | 2.2.3.4 | 2.2.3.5 |
| 2.2.3.6 | 2.2.3.7 | 2.3.3.1 | 2.3.3.2 | 2.3.3.3 | 2.3.3.4 | 2.3.3.5 | 2.3.3.6 | 2.3.3.7 | 2.4.3.1 | 2.4.3.2 | 2.4.3.3 | 2.4.3.4 |
| 2.4.3.5 | 2.4.3.6 | 2.4.3.7 | 2.5.3.1 | 2.5.3.2 | 2.5.3.3 | 2.5.3.4 | 2.5.3.5 | 2.5.3.6 | 2.5.3.7 | 2.6.3.1 | 2.6.3.2 | 2.6.3.3 |
| 2.6.3.4 | 2.6.3.5 | 2.6.3.6 | 2.6.3.7 | 2.7.3.1 | 2.7.3.2 | 2.7.3.3 | 2.7.3.4 | 2.7.3.5 | 2.7.3.6 | 2.7.3.7 | 2.8.3.1 | 2.8.3.2 |
| 2.8.3.3 | 2.8.3.4 | 2.8.3.5 | 2.8.3.6 | 2.8.3.7 | 2.9.3.1 | 2.9.3.2 | 2.9.3.3 | 2.9.3.4 | 2.9.3.5 | 2.9.3.6 | 2.9.3.7 | 3.1.3.1 |
| 3.1.3.2 | 3.1.3.3 | 3.1.3.4 | 3.1.3.5 | 3.1.3.6 | 3.1.3.7 | 3.2.3.1 | 3.2.3.2 | 3.2.3.3 | 3.2.3.4 | 3.2.3.5 | 3.2.3.6 | 3.2.3.7 |
| 3.3.3.1 | 3.3.3.2 | 3.3.3.3 | 3.3.3.4 | 3.3.3.5 | 3.3.3.6 | 3.3.3.7 | 3.4.3.1 | 3.4.3.2 | 3.4.3.3 | 3.4.3.4 | 3.4.3.5 | 3.4.3.6 |
| 3.4.3.7 | 3.5.3.1 | 3.5.3.2 | 3.5.3.3 | 3.5.3.4 | 3.5.3.5 | 3.5.3.6 | 3.5.3.7 | 3.6.3.1 | 3.6.3.2 | 3.6.3.3 | 3.6.3.4 | 3.6.3.5 |
| 3.6.3.6 | 3.6.3.7 | 3.7.3.1 | 3.7.3.2 | 3.7.3.3 | 3.7.3.4 | 3.7.3.5 | 3.7.3.6 | 3.7.3.7 | 3.8.3.1 | 3.8.3.2 | 3.8.3.3 | 3.8.3.4 |
| 3.8.3.5 | 3.8.3.6 | 3.8.3.7 | 3.9.3.1 | 3.9.3.2 | 3.9.3.3 | 3.9.3.4 | 3.9.3.5 | 3.9.3.6 | 3.9.3.7 | 4.1.3.1 | 4.1.3.2 | 4.1.3.3 |
| 4.1.3.4 | 4.1.3.5 | 4.1.3.6 | 4.1.3.7 | 4.2.3.1 | 4.2.3.2 | 4.2.3.3 | 4.2.3.4 | 4.2.3.5 | 4.2.3.6 | 4.2.3.7 | 4.3.3.1 | 4.3.3.2 |
| 4.3.3.3 | 4.3.3.4 | 4.3.3.5 | 4.3.3.6 | 4.3.3.7 | 4.4.3.1 | 4.4.3.2 | 4.4.3.3 | 4.4.3.4 | 4.4.3.5 | 4.4.3.6 | 4.4.3.7 | 4.5.3.1 |
| 4.5.3.2 | 4.5.3.3 | 4.5.3.4 | 4.5.3.5 | 4.5.3.6 | 4.5.3.7 | 4.6.3.1 | 4.6.3.2 | 4.6.3.3 | 4.6.3.4 | 4.6.3.5 | 4.6.3.6 | 4.6.3.7 |
| 4.7.3.1 | 4.7.3.2 | 4.7.3.3 | 4.7.3.4 | 4.7.3.5 | 4.7.3.6 | 4.7.3.7 | 4.8.3.1 | 4.8.3.2 | 4.8.3.3 | 4.8.3.4 | 4.8.3.5 | 4.8.3.6 |
| 4.8.3.7 | 4.9.3.1 | 4.9.3.2 | 4.9.3.3 | 4.9.3.4 | 4.9.3.5 | 4.9.3.6 | 4.9.3.7 | 5.1.3.1 | 5.1.3.2 | 5.1.3.3 | 5.1.3.4 | 5.1.3.5 |
| 5.1.3.6 | 5.1.3.7 | 5.2.3.1 | 5.2.3.2 | 5.2.3.3 | 5.2.3.4 | 5.2.3.5 | 5.2.3.6 | 5.2.3.7 | 5.3.3.1 | 5.3.3.2 | 5.3.3.3 | 5.3.3.4 |
| 5.3.3.5 | 5.3.3.6 | 5.3.3.7 | 5.4.3.1 | 5.4.3.2 | 5.4.3.3 | 5.4.3.4 | 5.4.3.5 | 5.4.3.6 | 5.4.3.7 | 5.5.3.1 | 5.5.3.2 | 5.5.3.3 |
| 5.5.3.4 | 5.5.3.5 | 5.5.3.6 | 5.5.3.7 | 5.6.3.1 | 5.6.3.2 | 5.6.3.3 | 5.6.3.4 | 5.6.3.5 | 5.6.3.6 | 5.6.3.7 | 5.7.3.1 | 5.7.3.2 |
| 5.7.3.3 | 5.7.3.4 | 5.7.3.5 | 5.7.3.6 | 5.7.3.7 | 5.8.3.4 | 5.8.3.2 | 5.8.3.3 | 5.8.3.4 | 5.8.3.5 | 5.8.3.6 | 5.8.3.7 | 5.9.3.1 |
| 5.9.3.2 | 5.9.3.3 | 5.9.3.4 | 5.9.3.5 | 5.9.3.6 | 5.9.3.7 | 6.1.3.1 | 6.1.3.2 | 6.1.3.3 | 6.1.3.4 | 6.1.3.5 | 6.1.3.6 | 6.1.3.7 |
| 6.2.3.1 | 6.2.3.2 | 6.2.3.3 | 6.2.3.4 | 6.2.3.5 | 6.2.3.6 | 6.2.3.7 | 6.3.3.1 | 6.3.3.2 | 6.3.3.3 | 6.3.3.4 | 6.3.3.5 | 6.3.3.6 |
| 6.3.3.7 | 6.4.3.1 | 6.4.3.2 | 6.4.3.3 | 6.4.3.4 | 6.4.3.5 | 6.4.3.6 | 6.4.3.7 | 6.5.3.1 | 6.5.3.2 | 6.5.3.3 | 6.5.3.4 | 6.5.3.5 |
| 6.5.3.6 | 6.5.3.7 | 6.6.3.1 | 6.6.3.2 | 6.6.3.3 | 6.6.3.4 | 6.6.3.5 | 6.6.3.6 | 6.6.3.7 | 6.7.3.1 | 6.7.3.2 | 6.7.3.3 | 6.7.3.4 |
| 6.7.3.5 | 6.7.3.6 | 6.7.3.7 | 6.8.3.1 | 6.8.3.2 | 6.8.3.3 | 6.8.3.4 | 6.8.3.5 | 6.8.3.6 | 6.8.3.7 | 6.9.3.1 | 6.9.3.2 | 6.9.3.3 |
| 6.9.3.4 | 6.9.3.5 | 6.9.3.6 | 6.9.3.7 | 7.1.3.1 | 7.1.3.2 | 7.1.3.3 | 7.1.3.4 | 7.1.3.5 | 7.1.3.6 | 7.1.3.7 | 7.2.3.1 | 7.2.3.2 |
| 7.2.3.3 | 7.2.3.4 | 7.2.3.5 | 7.2.3.6 | 7.2.3.7 | 7.3.3.1 | 7.3.3.2 | 7.3.3.3 | 7.3.3.4 | 7.3.3.5 | 7.3.3.6 | 7.3.3.7 | 7.4.3.1 |
| 7.4.3.2 | 7.4.3.3 | 7.4.3.4 | 7.4.3.5 | 7.4.3.6 | 7.4.3.7 | 7.5.3.1 | 7.5.3.2 | 7.5.3.3 | 7.5.3.4 | 7.5.3.5 | 7.5.3.6 | 7.5.3.7 |
| 7.6.3.1 | 7.6.3.2 | 7.6.3.3 | 7.6.3.4 | 7.6.3.5 | 7.6.3.6 | 7.6.3.7 | 7.7.3.1 | 7.7.3.2 | 7.7.3.3 | 7.7.3.4 | 7.7.3.5 | 7.7.3.6 |
| 7.7.3.7 | 7.8.3.1 | 7.8.3.2 | 7.8.3.3 | 7.8.3.4 | 7.8.3.5 | 7.8.3.6 | 7.8.3.7 | 7.9.3.1 | 7.9.3.2 | 7.9.3.3 | 7.9.3.4 | 7.9.3.5 |
| 7.9.3.6 | 7.9.3.7 | 8.1.3.1 | 8.1.3.2 | 8.1.3.3 | 8.1.3.4 | 8.1.3.5 | 8.1.3.6 | 8.1.3.7 | 8.2.3.1 | 8.2.3.2 | 8.2.3.3 | 8.2.3.4 |
| 8.2.3.5 | 8.2.3.6 | 8.2.3.7 | 8.3.3.1 | 8.3.3.2 | 8.3.3.3 | 8.3.3.4 | 8.3.3.5 | 8.3.3.6 | 8.3.3.7 | 8.4.3.1 | 8.4.3.2 | 8.4.3.3 |
| 8.4.3.4 | 8.4.3.5 | 8.4.3.6 | 8.4.3.7 | 8.5.3.1 | 8.5.3.2 | 8.5.3.3 | 8.5.3.4 | 8.5.3.5 | 8.5.3.6 | 8.5.3.7 | 8.6.3.1 | 8.6.3.2 |
| 8.6.3.3 | 8.6.3.4 | 8.6.3.5 | 8.6.3.6 | 8.6.3.7 | 8.7.3.1 | 8.7.3.2 | 8.7.3.3 | 8.7.3.4 | 8.7.3.5 | 8.7.3.6 | 8.7.3.7 | 8.8.3.1 |
| 8.8.3.2 | 8.8.3.3 | 8.8.3.4 | 8.8.3.5 | 8.8.3.6 | 8.8.3.7 | 8.9.3.1 | 8.9.3.2 | 8.9.3.3 | 8.9.3.4 | 8.9.3.5 | 8.9.3.6 | 8.9.3.7 |
| 9.1.3.1 | 9.1.3.2 | 9.1.3.3 | 9.1.3.4 | 9.1.3.5 | 9.1.3.6 | 9.1.3.7 | 9.2.3.1 | 9.2.3.2 | 9.2.3.3 | 9.2.3.4 | 9.2.3.5 | 9.2.3.6 |
| 9.2.3.7 | 9.3.3.1 | 9.3.3.2 | 9.3.3.3 | 9.3.3.4 | 9.3.3.5 | 9.3.3.6 | 9.3.3.7 | 9.4.3.1 | 9.4.3.2 | 9.4.3.3 | 9.4.3.4 | 9.4.3.5 |
| 9.4.3.6 | 9.4.3.7 | 9.5.3.1 | 9.5.3.2 | 9.5.3.3 | 9.5.3.4 | 9.5.3.5 | 9.5.3.6 | 9.5.3.7 | 9.6.3.1 | 9.6.3.2 | 9.6.3.3 | 9.6.3.4 |
| 9.6.3.5 | 9.6.3.6 | 9.6.3.7 | 9.7.3.1 | 9.7.3.2 | 9.7.3.3 | 9.7.3.4 | 9.7.3.5 | 9.7.3.6 | 9.7.3.7 | 9.8.3.1 | 9.8.3.2 | 9.8.3.3 |
| 9.8.3.4 | 9.8.3.5 | 9.8.3.6 | 9.8.3.7 | 9.9.3.1 | 9.9.3.2 | 9.9.3.3 | 9.9.3.4 | 9.9.3.5 | 9.9.3.6 | 9.9.3.7 | 1.1.4.1 | 1.1.4.2 |
| 1.1.4.3 | 1.1.4.4 | 1.1.4.5 | 1.1.4.6 | 1.1.4.7 | 1.1.5.1 | 1.1.5.2 | 1.1.5.3 | 1.1.5.4 | 1.1.5.5 | 1.1.5.6 | 1.1.5.7 | 1.1.6.1 |
| 1.1.6.2 | 1.1.6.3 | 1.1.6.4 | 1.1.6.5 | 1.1.6.6 | 1.1.6.7 | 1.1.7.1 | 1.1.7.2 | 1.1.7.3 | 1.1.7.4 | 1.1.7.5 | 1.1.7.6 | 1.1.7.7 |
| 1.2.4.1 | 1.2.4.2 | 1.2.4.3 | 1.2.4.4 | 1.2.4.5 | 1.2.4.6 | 1.2.4.7 | 1.2.5.1 | 1.2.5.2 | 1.2.5.3 | 1.2.5.4 | 1.2.5.5 | 1.2.5.6 |
| 1.2.5.7 | 1.2.6.1 | 1.2.6.2 | 1.2.6.3 | 1.2.6.4 | 1.2.6.5 | 1.2.6.6 | 1.2.6.7 | 1.2.7.1 | 1.2.7.2 | 1.2.7.3 | 1.2.7.4 | 1.2.7.5 |
| 1.2.7.6 | 1.2.7.7 | 1.3.4.1 | 1.3.4.2 | 1.3.4.3 | 1.3.4.4 | 1.3.4.5 | 1.3.4.6 | 1.3.4.7 | 1.3.5.1 | 1.3.5.2 | 1.3.5.3 | 1.3.5.4 |
| 1.3.5.5 | 1.3.5.6 | 1.3.5.7 | 1.3.6.1 | 1.3.6.2 | 1.3.6.3 | 1.3.6.4 | 1.3.6.5 | 1.3.6.6 | 1.3.6.7 | 1.3.7.1 | 1.3.7.2 | 1.3.7.3 |
| 1.3.7.4 | 1.3.7.5 | 1.3.7.6 | 1.3.7.7 | 2.1.4.1 | 2.1.4.2 | 2.1.4.3 | 2.1.4.4 | 2.1.4.5 | 2.1.4.6 | 2.1.4.7 | 2.1.5.1 | 2.1.5.2 |
| 2.1.5.3 | 2.1.5.4 | 2.1.5.5 | 2.1.5.6 | 2.1.5.7 | 2.1.6.1 | 2.1.6.2 | 2.1.6.3 | 2.1.6.4 | 2.1.6.5 | 2.1.6.6 | 2.1.6.7 | 2.1.7.1 |
| 2.1.7.2 | 2.1.7.3 | 2.1.7.4 | 2.1.7.5 | 2.1.7.6 | 2.1.7.7 | 2.2.4.1 | 2.2.4.2 | 2.2.4.3 | 2.2.4.4 | 2.2.4.5 | 2.2.4.6 | 2.2.4.7 |
| 2.2.5.1 | 2.2.5.2 | 2.2.5.3 | 2.2.S.4 | 2.2.5.5 | 2.2.5.6 | 2.2.5.7 | 2.2.6.1 | 2.2.6.2 | 2.2.6.3 | 2.2.6.4 | 2.2.6.5 | 2.2.6.6 |
| 2.2.6.7 | 2.2.7.1 | 2.2.7.2 | 2.2.7.3 | 2.2.7.4 | 2.2.7.5 | 2.2.7.6 | 2.2.7.7 | 2.3.4.1 | 2.3.4.2 | 2.3.4.3 | 2.3.4.4 | 2.3.4.5 |
| 2.3.4.6 | 2.3.4.7 | 2.3.5.1 | 2.3.5.2 | 2.3.5.3 | 2.3.5.4 | 2.3.5.5 | 2.3.5.6 | 2.3.5.7 | 2.3.6.1 | 2.3.6.2 | 2.3.6.3 | 2.3.6.4 |
| 2.3.6.5 | 2.3.6.6 | 2.3.6.7 | 2.3.7.1 | 2.3.7.2 | 2.3.7.3 | 2.3.7.4 | 2.3.7.5 | 2.3.7.6 | 2.3.7.7 | 3.1.4.1 | 3.1.4.2 | 3.1.4.3 |
| 3.1.4.4 | 3.1.4.5 | 3.1.4.6 | 3.1.4.7 | 3.1.5.1 | 3.1.5.2 | 3.1.5.3 | 3.1.5.4 | 3.1.5.5 | 3.1.5.6 | 3.1.5.7 | 3.1.6.1 | 3.1.6.2 |
| 3.1.6.3 | 3.1.6.4 | 3.1.6.5 | 3.1.6.6 | 3.1.6.7 | 3.1.7.1 | 3.1.7.2 | 3.1.7.3 | 3.1.7.4 | 3.1.7.5 | 3.1.7.6 | 3.1.7.7 | 3.2.4.1 |
| 3.2.4.2 | 3.2.4.3 | 3.2.4.4 | 3.2.4.5 | 3.2.4.6 | 3.2.4.7 | 3.2.5.1 | 3.2.5.2 | 3.2.5.3 | 3.2.5.4 | 3.2.5.5 | 3.2.5.6 | 3.2.5.7 |
| 3.2.6.1 | 3.2.6.2 | 3.2.6.3 | 3.2.6.4 | 3.2.6.5 | 3.2.6.6 | 3.2.6.7 | 3.2.7.1 | 3.2.7.2 | 3.2.7.3 | 3.2.7.4 | 3.2.7.5 | 3.2.7.6 |
| 3.2.7.7 | 3.3.4.1 | 3.3.4.2 | 3.3.4.3 | 3.3.4.4 | 3.3.4.5 | 3.3.4.6 | 3.3.4.7 | 3.3.5.1 | 3.3.5.2 | 3.3.5.3 | 3.3.5.4 | 3.3.5.5 |
| 3.3.5.6 | 3.3.5.7 | 3.3.6.1 | 3.3.6.2 | 3.3.6.3 | 3.3.6.4 | 3.3.6.5 | 3.3.6.6 | 3.3.6.7 | 3.3.7.1 | 3.3.7.2 | 3.3.7.3 | 3.3.7.4 |
| 3.3.7.5 | 3.3.7.6 | 3.3.7.7 | 4.1.4.1 | 4.1.4.2 | 4.1.4.3 | 4.1.4.4 | 4.1.4.5 | 4.1.4.6 | 4.1.4.7 | 4.1.5.1 | 4.1.5.2 | 4.1.5.3 |

TABLE 2-continued

| | | | | | | | | | | | |
|---|---|---|---|---|---|---|---|---|---|---|---|
| 4.1.5.4 | 4.1.5.5 | 4.1.5.6 | 4.1.5.7 | 4.1.6.1 | 4.1.6.2 | 4.1.6.3 | 4.1.6.4 | 4.1.6.5 | 4.1.6.6 | 4.1.6.7 | 4.1.7.1 | 4.1.7.2 |
| 4.1.7.3 | 4.1.7.4 | 4.1.7.5 | 4.1.7.6 | 4.1.7.7 | 4.2.4.1 | 4.2.4.2 | 4.2.4.3 | 4.2.4.4 | 4.2.4.5 | 4.2.4.6 | 4.2.4.7 | 4.2.5.1 |
| 4.2.5.2 | 4.2.5.3 | 4.2.5.4 | 4.2.5.5 | 4.2.5.6 | 4.2.5.7 | 4.2.6.1 | 4.2.6.2 | 4.2.6.3 | 4.2.6.4 | 4.2.6.5 | 4.2.6.6 | 4.2.6.7 |
| 4.2.7.1 | 4.2.7.2 | 4.2.7.3 | 4.2.7.4 | 4.2.7.5 | 4.2.7.6 | 4.2.7.7 | 4.3.4.1 | 4.3.4.2 | 4.3.4.3 | 4.3.4.4 | 4.3.4.5 | 4.3.4.6 |
| 4.3.4.7 | 4.3.5.1 | 4.3.5.2 | 4.3.5.3 | 4.3.5.4 | 4.3.5.5 | 4.3.5.6 | 4.3.5.7 | 4.3.6.1 | 4.3.6.2 | 4.3.6.3 | 4.3.6.4 | 4.3.6.5 |
| 4.3.6.6 | 4.3.6.7 | 4.3.7.1 | 4.3.7.2 | 4.3.7.3 | 4.3.7.4 | 4.3.7.5 | 4.3.7.6 | 4.3.7.7 | 5.1.4.1 | 5.1.4.2 | 5.1.4.3 | 5.1.4.4 |
| 5.1.4.5 | 5.1.4.6 | 5.1.4.7 | 5.1.5.1 | 5.1.5.2 | 5.1.5.3 | 5.1.5.4 | 5.1.5.5 | 5.1.5.6 | 5.1.5.7 | 5.1.6.1 | 5.1.6.2 | 5.1.6.3 |
| 5.1.6.4 | 5.1.6.5 | 5.1.6.6 | 5.1.6.7 | 5.1.7.1 | 5.1.7.2 | 5.1.7.3 | 5.1.7.4 | 5.1.7.5 | 5.1.7.6 | 5.1.7.7 | 5.2.4.1 | 5.2.4.2 |
| 5.2.4.3 | 5.2.4.4 | 5.2.4.5 | 5.2.4.6 | 5.2.4.7 | 5.2.5.1 | 5.2.5.2 | 5.2.5.3 | 5.2.5.4 | 5.2.5.5 | 5.2.5.6 | 5.2.5.7 | 5.2.6.1 |
| 5.2.6.2 | 5.2.6.3 | 5.2.6.4 | 5.2.6.5 | 5.2.6.6 | 5.2.6.7 | 5.2.7.1 | 5.2.7.2 | 5.2.7.3 | 5.2.7.4 | 5.2.7.5 | 5.2.7.6 | 5.2.7.7 |
| 5.3.4.1 | 5.3.4.2 | 5.3.4.3 | 5.3.4.4 | 5.3.4.5 | 5.3.4.6 | 5.3.4.7 | 5.3.5.1 | 5.3.5.2 | 5.3.5.3 | 5.3.5.4 | 5.3.5.5 | 5.3.5.6 |
| 5.3.5.7 | 5.3.6.1 | 5.3.6.2 | 5.3.6.3 | 5.3.6.4 | 5.3.6.5 | 5.3.6.6 | 5.3.6.7 | 5.3.7.1 | 5.3.7.2 | 5.3.7.3 | 5.3.7.4 | 5.3.7.5 |
| 5.3.7.6 | 5.3.7.7 | 6.1.4.1 | 6.1.4.2 | 6.1.4.3 | 6.1.4.4 | 6.1.4.5 | 6.1.4.6 | 6.1.4.7 | 6.1.5.1 | 6.1.5.2 | 6.1.5.3 | 6.1.5.4 |
| 6.1.5.5 | 6.1.5.6 | 6.1.5.7 | 6.1.6.1 | 6.1.6.2 | 6.1.6.3 | 6.1.6.4 | 6.1.6.5 | 6.1.6.6 | 6.1.6.7 | 6.1.7.1 | 6.1.7.2 | 6.1.7.3 |
| 6.1.7.4 | 6.1.7.5 | 6.1.7.6 | 6.1.7.7 | 6.2.4.1 | 6.2.4.2 | 6.2.4.3 | 6.2.4.4 | 6.2.4.5 | 6.2.4.6 | 6.2.4.7 | 6.2.5.1 | 6.2.5.2 |
| 6.2.5.3 | 6.2.5.4 | 6.2.5.5 | 6.2.5.6 | 6.2.5.7 | 6.2.6.1 | 6.2.6.2 | 6.2.6.3 | 6.2.6.4 | 6.2.6.5 | 6.2.6.6 | 6.2.6.7 | 6.2.7.1 |
| 6.2.7.2 | 6.2.7.3 | 6.2.7.4 | 6.2.7.5 | 6.2.7.6 | 6.2.7.7 | 6.3.4.1 | 6.3.4.2 | 6.3.4.3 | 6.3.4.4 | 6.3.4.5 | 6.3.4.6 | 6.3.4.7 |
| 6.3.5.1 | 6.3.5.2 | 6.3.5.3 | 6.3.S.4 | 6.3.5.5 | 6.3.5.6 | 6.3.5.7 | 6.3.6.1 | 6.3.6.2 | 6.3.6.3 | 6.3.6.4 | 6.3.6.5 | 6.3.6.6 |
| 6.3.6.7 | 6.3.7.1 | 6.3.7.2 | 6.3.7.3 | 6.3.7.4 | 6.3.7.5 | 6.3.7.6 | 6.3.7.7 | 7.1.4.1 | 7.1.4.2 | 7.1.4.3 | 7.1.4.4 | 7.1.4.5 |
| 7.1.4.6 | 7.1.4.7 | 7.1.5.1 | 7.1.5.2 | 7.1.5.3 | 7.1.5.4 | 7.1.5.5 | 7.1.5.6 | 7.1.5.7 | 7.1.6.1 | 7.1.6.2 | 7.1.6.3 | 7.1.6.4 |
| 7.1.6.5 | 7.1.6.6 | 7.1.6.7 | 7.1.7.1 | 7.1.7.2 | 7.1.7.3 | 7.1.7.4 | 7.1.7.5 | 7.1.7.6 | 7.1.7.7 | 7.2.4.1 | 7.2.4.2 | 7.2.4.3 |
| 7.2.4.4 | 7.2.4.5 | 7.2.4.6 | 7.2.4.7 | 7.2.5.1 | 7.2.5.2 | 7.2.5.3 | 7.2.5.4 | 7.2.5.5 | 7.2.5.6 | 7.2.5.7 | 7.2.6.1 | 7.2.6.2 |
| 7.2.6.3 | 7.2.6.4 | 7.2.6.5 | 7.2.6.6 | 7.2.6.7 | 7.2.7.1 | 7.2.7.2 | 7.2.7.3 | 7.2.7.4 | 7.2.7.5 | 7.2.7.6 | 7.2.7.7 | 7.3.4.1 |
| 7.3.4.2 | 7.3.4.3 | 7.3.4.4 | 7.3.4.5 | 7.3.4.6 | 7.3.4.7 | 7.3.5.1 | 7.3.5.2 | 7.3.5.3 | 7.3.5.4 | 7.3.5.5 | 7.3.5.6 | 7.3.5.7 |
| 7.3.6.1 | 7.3.6.2 | 7.3.6.3 | 7.3.6.4 | 7.3.6.5 | 7.3.6.6 | 7.3.6.7 | 7.3.7.1 | 7.3.7.2 | 7.3.7.3 | 7.3.7.4 | 7.3.7.5 | 7.3.7.6 |
| 7.3.7.7 | 8.1.4.1 | 8.1.4.2 | 8.1.4.3 | 8.1.4.4 | 8.1.4.5 | 8.1.4.6 | 8.1.4.7 | 8.1.5.1 | 8.1.5.2 | 8.1.5.3 | 8.1.5.4 | 8.1.5.5 |
| 8.1.5.6 | 8.1.5.7 | 8.1.6.1 | 8.1.6.2 | 8.1.6.3 | 8.1.6.4 | 8.1.6.5 | 8.1.6.6 | 8.1.6.7 | 8.1.7.1 | 8.1.7.2 | 8.1.7.3 | 8.1.7.4 |
| 8.1.7.5 | 8.1.7.6 | 8.1.7.7 | 8.2.4.1 | 8.2.4.2 | 8.2.4.3 | 8.2.4.4 | 8.2.4.5 | 8.2.4.6 | 8.2.4.7 | 8.2.5.1 | 8.2.5.2 | 8.2.5.3 |
| 8.2.5.4 | 8.2.5.5 | 8.2.5.6 | 8.2.5.7 | 8.2.6.1 | 8.2.6.2 | 8.2.6.3 | 8.2.6.4 | 8.2.6.5 | 8.2.6.6 | 8.2.6.7 | 8.2.7.1 | 8.2.7.2 |
| 8.2.7.3 | 8.2.7.4 | 8.2.7.5 | 8.2.7.6 | 8.2.7.7 | 8.3.4.1 | 8.3.4.2 | 8.3.4.3 | 8.3.4.4 | 8.3.4.5 | 8.3.4.6 | 8.3.4.7 | 8.3.5.1 |
| 8.3.5.2 | 8.3.5.3 | 8.3.5.4 | 8.3.5.5 | 8.3.5.6 | 8.3.5.7 | 8.3.6.1 | 8.3.6.2 | 8.3.6.3 | 8.3.6.4 | 8.3.6.5 | 8.3.6.6 | 8.3.6.7 |
| 8.3.7.1 | 8.3.7.2 | 8.3.7.3 | 8.3.7.4 | 8.3.7.5 | 8.3.7.6 | 8.3.7.7 | 9.1.4.1 | 9.1.4.2 | 9.1.4.3 | 9.1.4.4 | 9.1.4.5 | 9.1.4.6 |
| 9.1.4.7 | 9.1.5.1 | 9.1.5.2 | 9.1.5.3 | 9.1.5.4 | 9.1.5.5 | 9.1.5.6 | 9.1.5.7 | 9.1.6.1 | 9.1.6.2 | 9.1.6.3 | 9.1.6.4 | 9.1.6.5 |
| 9.1.6.6 | 9.1.6.7 | 9.1.7.1 | 9.1.7.2 | 9.1.7.3 | 9.1.7.4 | 9.1.7.5 | 9.1.7.6 | 9.1.7.7 | 9.2.4.1 | 9.2.4.2 | 9.2.4.3 | 9.2.4.4 |
| 9.2.4.5 | 9.2.4.6 | 9.2.4.7 | 9.2.5.1 | 9.2.5.2 | 9.2.5.3 | 9.2.5.4 | 9.2.5.5 | 9.2.5.6 | 9.2.5.7 | 9.2.6.1 | 9.2.6.2 | 9.2.6.3 |
| 9.2.6.4 | 9.2.6.5 | 9.2.6.6 | 9.2.6.7 | 9.2.7.1 | 9.2.7.2 | 9.2.7.3 | 9.2.7.4 | 9.2.7.5 | 9.2.7.6 | 9.2.7.7 | 9.3.4.1 | 9.3.4.2 |
| 9.3.4.3 | 9.3.4.4 | 9.3.4.5 | 9.3.4.6 | 9.3.4.7 | 9.3.5.1 | 9.3.5.2 | 9.3.5.3 | 9.3.5.4 | 9.3.5.5 | 9.3.5.6 | 9.3.5.7 | 9.3.6.1 |
| 9.3.6.2 | 9.3.6.3 | 9.3.6.4 | 9.3.6.5 | 9.3.6.6 | 9.3.6.7 | 9.3.7.1 | 9.3.7.2 | 9.3.7.3 | 9.3.7.4 | 9.3.7.5 | 9.3.7.6 | 9.3.7.7 |

Methods for Lipid Synthesis

One synthesizes the lipids and their intermediates as shown in the schemes below.

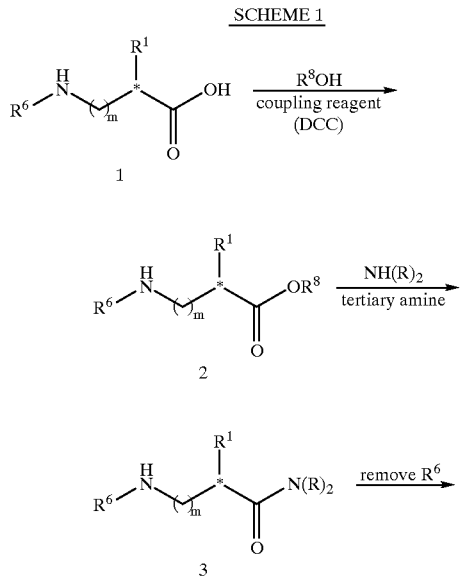

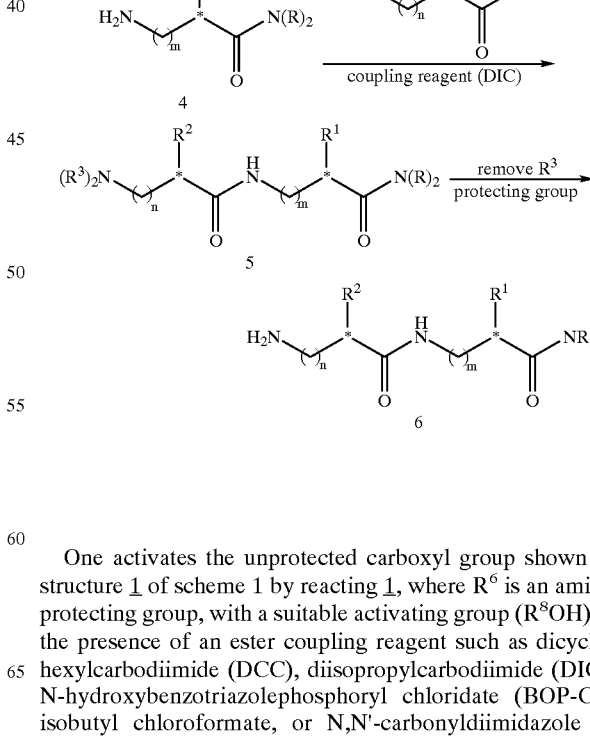

One activates the unprotected carboxyl group shown in structure 1 of scheme 1 by reacting 1, where $R^6$ is an amino protecting group, with a suitable activating group ($R^8OH$) in the presence of an ester coupling reagent such as dicyclohexylcarbodiimide (DCC), diisopropylcarbodiimide (DIC), N-hydroxybenzotriazolephosphoryl chloridate (BOP-Cl), isobutyl chloroformate, or N,N'-carbonyldiimidazole to form the activated ester group in 2 using previously described methods (see, for example, J. March, editor, *Advanced Organic Chemistry,* Wiley & Sons, third edition, 1985, p 348–351). Any amine groups at $R^1$ are usually protected with an $R^4$ or $R^5$ amine protecting group. $R^8$ activating groups linked to the amino acid (—$OR^8$) function as a leaving group for synthesizing 3. Suitable $R^8OH$ activating groups include N-hydroxysuccinimide (NHS), p-nitrophenol, pentachlorophenol, and pentafluorophenol. One reacts the activated ester in a solvent such as methylene chloride with about one equivalent each of a secondary amine, e.g., $NH(R)_2$, and a tertiary amine such as N,N-diisopropylethylamine or triethylamine (TEA) at room temperature (about 18–26°) to yield structure 3. $R^6$ is removed to yield 4 which is coupled with 7 in a solvent such as methylene chloride to yield 5, a protected structure A lipid. Suitable amide coupling reagents for preparing 5 include the coupling reagents described above, i.e., DIC, etc. The $R^3$ amino protecting group present on the protected lipid 5 is removed to yield the unprotected lipid where $R^3$ is hydrogen. When $R^3$ is a protecting group, it is usually the same as any $R^4$ or $R^5$ protecting groups that may be present at $R^1$ and/or $R^2$. During the deprotection reactions, the amount of deprotected lipid or intermediates increases from a low level, e.g., less than about 1% w/w, to a high level, e.g., more than about 99% w/w. While the deprotection reactions are in progress, they generate varying amounts of different species of partially deprotected lipid intermediates.

Compounds of structure 2 shown in scheme 1 wherein $R^1$ contains an amine group(s) will have an $R^4$ and/or $R^5$ amine protecting group in synthesizing 5 to avoid forming adducts at the $R^1$ amino groups. The $R^4$ and/or $R^5$ amine protecting group and the $R^6$ amine protecting group are optionally different so that $R^6$ can be removed without removing $R^4$ and/or $R^5$ i.e., $R^6$ and $R^4$ and/or $R^5$ are different and can be differentially removed from a given molecule. In general, $R^4$ and $R^5$ are the same. One usually uses the $R^4$, $R^5$ and $R^6$ amine protecting groups to obtain structure A lipids where $R^4$, $R^5$ and $R^6$ are all hydrogen when one prepares the fully deprotected molecule.

The $R^4$, $R^5$ and $R^6$ amine protecting groups will be selected from groups that have been described (see for example, T. W. Greene et al., editors, *Protective Groups in Organic Chemistry,* second edition, 1991, Wiley, p 309–405, p 406–412 and p 441–452). These protecting groups include monovalent amine protecting groups, i.e., one of $R^4$, $R^5$ or $R^6$ is a protecting group and the other is hydrogen. Alternatively, these groups are divalent amine protecting groups, i.e., both $R^4$, $R^5$ or $R^6$ together are a protecting group. A very large number of amino protecting groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994); J. F. W. McOmie, *Protective Groups in Organic Chemistry,* Plenum Press, 1973, which are incorporated by reference in their entirety herein.

Typical amino protecting groups are described by Greene at pages 315–385. They include Carbamates (methyl and ethyl, 9-fluorenylmethyl, 9(2-sulfo)fluoroenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungssten)] carbeniyl, N-copper or N-zinc chelate); N—N Derivatives (N-nitro, N-nitroso, N-oxide); N—P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si Derivatives; N—S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzelesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Amine protecting groups such as benzyl carbamate (Cbz), p-methoxybenzyl carbamate (Moz), p-bromobenzyl carbamate, 9-fluorenylmethyl carbamate (FMOC), or 2,4-dichlorobenzyl will be used where an acid stable protective group is desired while protective groups such as t-butyl carbamate (t-BOC) or 1-adamantyl carbamate (Adoc) will be used where a base stable or nucleophile stable group is desired. Protective groups will be used to protect amine groups when coupling reactions are carried out such as in conversion of 1 to 2 or 4 to 5. The amine protecting groups at $R^4$, $R^5$ and/or $R^6$ are optionally all the same. Protective groups such as 2-(2'- or 4'-pyridyl)ethyl carbamate will be used where a group stable to catalytic palladium-carbon hydrogenation or to trifluoroacetic acid is desired. $R^4$ and/or $R^5$ can thus be selected from a diverse group of known protective groups as needed. Exemplary $R^4$–$R^5$ and $R^6$ groups that can be present in 5 include the following pairs of protective groups. Other suitable $R^4$ and/or $R^5$–$R^6$ combinations are determined experimentally by routine methods using the relative reactivity information of the different amine protecting groups described by Greene et al, supra at p 406–412 and p 441–452.

| $R^4$ and/or $R^5$ | $R^6$ | $R^6$ cleavage condition |
|---|---|---|
| t-BOC | Cbz | hydrogenation |
| Cbz | t-BOC | acid hydrolysis |
| FMOC | Cbz | hydrogenation |
| Adoc | Cbz | hydrogenation |
| t-BOC | FMOC | base hydrolysis |
| FMOC | t-BOC | acid hydrolysis |

When $R^3$ is present as a protecting group, it will typically be the same as $R^4$ or $R^5$ so that 5 can be deprotected using a single set of deprotection conditions.

Intermediates of structure $HN(R)_2$ are synthesized by reacting an acyl chloride of structure $ClC(O)R^9$ wherein $R^9$ is alkyl ($C_{9-21}$) or mono unsaturated alkenyl ($C_{9-21}$), with $H_2NR$ to obtain the intermediate $HN(R)[C(O)R^9]$ which is reduced (using, for example, Borane or lithium aluminum hydride) to yield $HN(R)_2$. The acyl chlorides are obtained by reaction of the free fatty acid with, for example, oxalyl chloride, $SOCl_2$ or $PCl_3$. The $H_2NR$ intermediate is obtained by reacting $ClC(O)R^9$ with ammonia gas (at about 0° C.). In addition, many $R^9C(O)Cl$ chlorides and $H_2NR$ amines are available commercially (Aldrich Chemical, Kodak, K&K Chemicals).

One prepares lipid A compounds where $R^3$, $R^4$ and/or $R^5$ are —$CH_2(CF_2)_pCF_3$ by converting a perfluoro alcohol, $HOCH_2(CF_2)_pCF_3$, with methanesulfonyl chloride ($CH_3SO_2Cl$, MsCl) or p-toluenesulfonyl chloride (TsCl) to obtain the activated alcohol derivative, e.g., $CH_3SO_2OCH_2(CF_2)_pCF_3$. The activated alcohol derivative is then reacted with an amino acid having a suitably protected carboxylic acid group to link two —$CH_2(CF_2)_pCF_3$ groups to the free amine of the amino acid. Perfluoro alcohols are available commercially and can also be prepared by known methods, i.e., by reduction of a carboxylic acid, $HO_2C(CF_2)_pCF_3$, to the corresponding alcohol, $HOCH_2(CF_2)_pCF_3$, in the presence of a reducing agent.

One prepares lipid A compounds where one $R^3$, $R^4$ and/or $R^5$ is —$CH_2(CF_2)_pCF_3$ and the other is hydrogen by oxidizing a perfluoro alcohol, $HOCH_2(CF_2)_pCF_3$, to the aldehyde, $CF_3(CF_2)_pCHO$, by known methods, i.e., oxidation using permanganate ion or Moffet oxidation conditions. The aldehyde is coupled to an amino acid having a protected carboxylic acid group by reductive amination to yield the protected structure A lipid having a hydrogen and a —$CH_2(CF_2)_pCF_3$ group at $R^3$, $R^4$ and/or $R^5$.

One uses methods to obtain A having one or two —$CH_2(CF_2)_pCF_3$ groups at $R^3$ and a free amine at $R^4$ and/or $R^5$ by using as a starting material A with any amines at $R^4$ and/or $R^5$ protected and the amine at $R^3$ unprotected. The presence of the fluorine atoms at $R^3$, $R^4$ or $R^5$ decreases the pKa of the amine to which the —$CH_2(CF_2)_pCF_3$ group is attached. Such amines have a lower net positive charge at physiological pH, i.e., about 7.0–7.4, than the free amine. Typically these amines will have a net positive charge of about 0 to about 0.4.

One prepares structure A compounds where $R^3$, $R^4$ and/or $R^5$ is alkyl or aryl by reacting the activated alcohol, e.g., $CH_3SO_2O$-alkyl or $CH_3SO_2O$-aryl, and coupling it with the free amine using carboxyl protected amino acid as described above for preparation of amines having disubstituted perfluoroalkyl groups. One prepares lipid A compounds where one of $R^3$, $R^4$ and/or $R^5$ is —$CH_2(CF_2)_pCF_3$ and the others are hydrogen by reductive amination using the corresponding aldehyde and protected amino acid as described above.

One synthesizes structure A lipids containing a cholesteryl moiety as shown in scheme 2.

Scheme 2

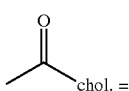
chol. =

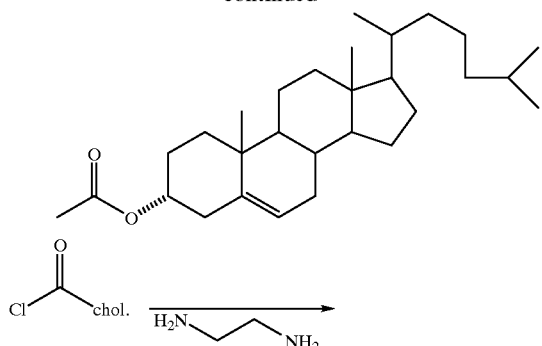

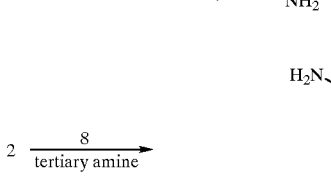

Cholesteryl chloroformate (Aldrich, Cat. No. C7,700-7) is coupled to ethylenediamine in organic solvent (CH$_2$Cl$_2$) at about 0–24° C. to obtain $\underline{8}$. One converts $\underline{8}$ to the protected lipid intermediate $\underline{90}$ by reaction with $\underline{2}$. The protected lipid intermediates $\underline{9}$ and $\underline{11}$ are deprotected as described in scheme 1 above.

Schemes 3 and 4 shows the synthesis of structure $\underline{A}$ cationic lipids containing $\underline{C}$ or $\underline{D}$ at $R^1$ or $R^2$ where m or n are 0.

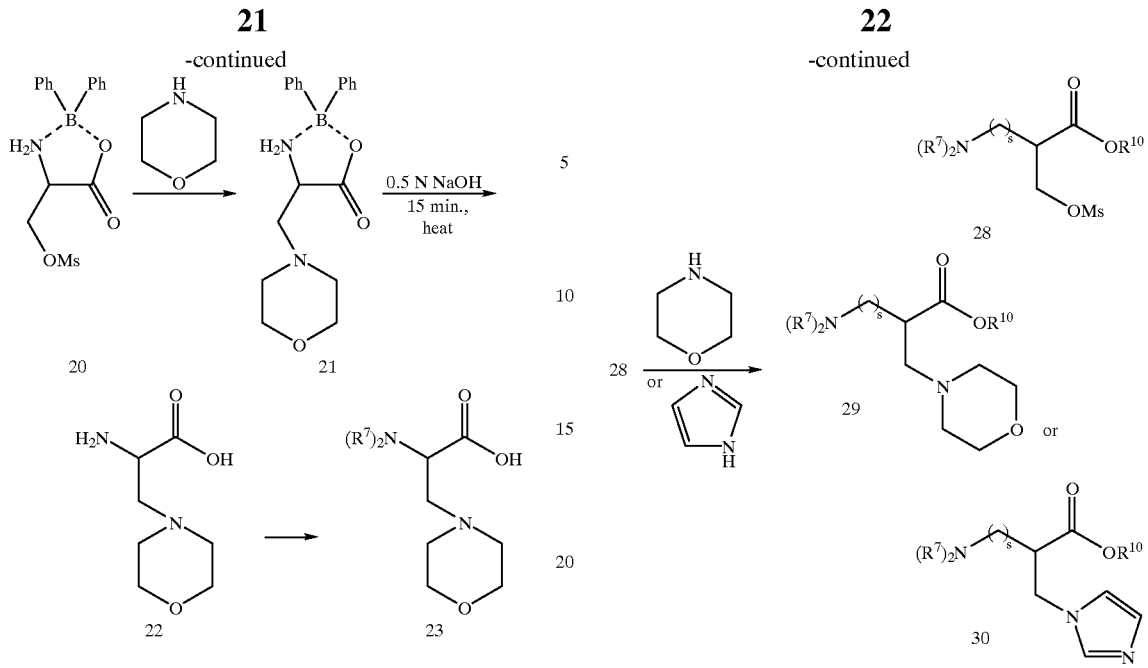

One synthesizes 14 by reaction of the protected amino acid serine with phthalic anhydride essentially as described (Sasaki et al., *J. Org. Chem.* 43 2320, 1978). Compound 13 is available commercially or is prepared by reaction of carboxyl-protected serine with isobutene in the presence of acid. The group ᵗBu is t-butyl. $R^{10}$ is an acid stable carboxyl protecting group, e.g., lower alkyl such as methyl, ethyl, propyl, isopropyl, n-butyl or sec-butyl or $R^{10}$ is benzyl (see for example, T. W. Greene et al., editors, *Protective Groups in Organic Chemistry*, second edition, 1991, Wiley, p 224–276). One removes the t-butyl protecting group using trifluoroacetic acid and prepares the mesylate, 15, by reaction with methane sulfonyl chloride ($CH_3SO_2Cl$, MsCl). The group Ms is —$SO_2CH_3$. One prepares 16 and 17 by reaction with the appropriate free base in methylene chloride in the presence of a tertiary amine, e.g., TEA. One then removes $R^{10}$ from 16 or 17, to afford the amino-protected amino acid.

One optionally incorporates C or D into structure A lipids by converting 18 to 19 essentially as described (Staatz et al., *Liebigs Ann. Chem.* 127, 1989). One prepares 20 and 21 as described for 15 and 16, followed by preparation of 22 essentially as described (Nefkens et al., *Tetrahedron* 39:2295, 1983) and then one prepares 23 using a nitrogen protecting group. $R^7$ is $R^3$ or $R^6$, depending on whether one intends to the intermediate for 2 or for 7 in Scheme 1. One prepares the analogs of 21, 22 and 23, i.e., 24, 25 and 26 respectively (not shown), by reacting 20 with imidazole.

One prepares structure A lipids containing C or D at $R^1$ or $R^2$ where m or n are 1–4 as shown in Scheme 5.

SCHEME 5

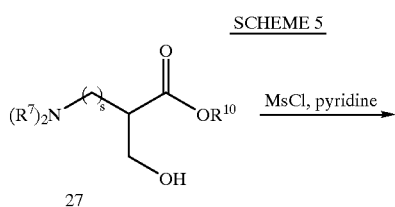

In Scheme 5, s is 1, 2, 3 or 4. One obtains 27 by known methods. One then converts 27 to 28 as described above for preparation of 15. When one uses 29 or 30 in place of 2 in Scheme 1, one will replace $R^{10}$ with $R^8$. $R^{10}$ and $R^8$ are not the same and the groups must be exchanged before use in Scheme 1. When one uses 29 or 30 in place of 7 in Scheme 1, one removes $R^6$ to leave the free carboxyl derivative, followed by coupling with 4 to obtain 5.

One prepares structure A lipids containing B at $R^1$ or $R^2$ where m or n are 1, 2, 3, or 4 as shown in Scheme 6.

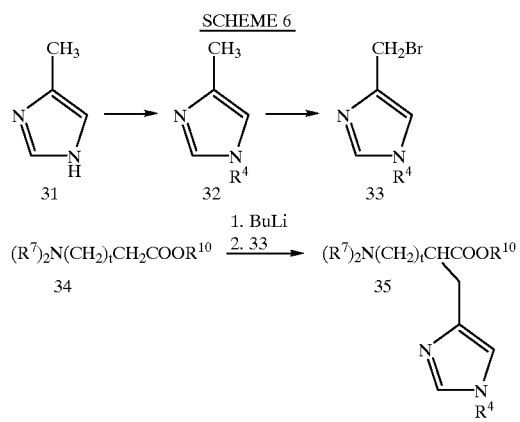

One converts 31 to 32 using standard amine protecting groups. One converts 31 to 32 by reacting 31 with N-bromosuccinimide and azobis(cyclohexanecarbonitrile) (Aldrich) in light or by reaction with N-bromosuccinimide and a peroxide, e.g., benxoyl peroxide. $R^4$ in Scheme 5 is a monovalent amine protecting group and t is an integer of the value 1, 2, 3, or 4. Coupling of 33 with 34 is accomplished in two steps using n-butyl lithium first and then addition of 33. When $R^7$ is an amine protecting group, it will not be the same as $R^4$ to allow removal of $R^7$ from 35 without removing $R^4$.

2-Aminopyridine containing compositions of the invention are prepared by methods common in the art. Typically a 2-fluoropyridine (e.g. 2-fluoropyridine CAS Reg. No. 372-48-5, Aldrich Chemical No. F1,525-0) is reacted by conventional methods with an amine.

To the extent any compound of this invention cannot be produced by one of the foregoing schemes other methods will be apparent to the artisan referring to conventional methods and the relevant teachings contained herein (see for instance Liotta et al. "Compendium of Organic Synthesis Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; March, J., "Advanced Organic Chemistry, Third Edition", (John Wiley & Sons, New York, 1985); Saul Patai, "The Chemistry of the Amino Group. Volume 4" (Interscience, John Wiley & Sons, New York, 1968); Saul Patai, "Supplement F. The Chemistry of Amino, Nitroso and Nitro Compounds and their Derivatives, Parts 1 and 2" (Interscience, John Wiley & Sons, New York, 1982); as well as "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

The salts include pharmaceutically or physiologically acceptable non-toxic salts of these compounds. Such salts may include those derived by combination of appropriate cations such as alkali and alkaline earth metal ions or ammonium and quaternary amino ions with the acid anion moiety of the phosphate or phosphorothioate acid group present in polynucleotides. In addition salts may be formed from acid addition of certain organic and inorganic acids with basic centers of the purine, specifically guanine, or pyrimidine base present in polynucleotides. Suitable salts of the invention cationic lipids include acid addition salts such as HCl, HBr, HF, HI, $H_2SO_4$, and trifluoroacetate. The salts may be formed from acid addition of certain organic and inorganic acids, e.g., HCl, HBr, $H_2SO_4$, amino acids or organic sulfonic acids, with basic centers, typically amines, or with acidic groups. The compositions herein also comprise compounds of the invention in their un-ionized, as well as zwitterionic forms.

Cationic lipid-polyanionic polymer complexes are formed by preparing lipid particles or suspensions consisting of either (1) an invention cationic lipid of structure $\underline{A}$ or (2) an invention structure $\underline{A}$ lipid-colipid mixture, followed by adding a polyanionic polymer to the lipid particles in suspension at about room temperature. Alternatively, one optionally adds the anionic compound to the lipids prior to drying so that one then prepares the complexes starting from a layer of dried lipid containing anionic compound. A third method of preparing the lipid-anionic compound complexes is to resuspend the dried lipids in liquid containing the anionic compound—usually resuspension will be by vortexing the lipids and/or about 5–10 cycles of freezing (usually on dry ice) and thawing (usually at about room temperature to about 37° C.). The mixture is then allowed to form a complex over a period of about 5 min to about 20 hours, with about 10 to 120 min most conveniently used. The complexes may be formed over a longer period, but additional enhancement of transfection efficiency will usually not be gained by a longer period of complexing. A phospholipid such as DOPE is optionally used as a colipid with the invention lipids but is not necessary. Additional colipids that are optionally suitable for preparing lipid complexes with the invention structure $\underline{A}$ lipids are dimyristoylphosphatidylethanolamine, dipalmitoylphosphatidyl-ethanolamine, palmitoyloleoylphosphatidylethanolamine, cholesterol, distearoylphosphatidylthanolamine, phosphatidylethanolamine covalently linked to polyethylene glycol and mixtures of these colipids. The colipids may contribute to the fusogenic properties of the invention lipids.

The optimal cationic lipid:colipid ratio for a given invention cationic lipid is determined by mixing experiments to prepare lipid mixtures for complexing with a polyanion using cationic lipid:colipid ratios between about 1:10 and 10:1. Methods to determine optimal cationic lipid:colipid ratios have been described (see, for example, Felgner et al., *J. Biol. Chem.*, 269:2550–2561, 1964). Each lipid mixture is optionally tested using more than one nucleic acid-lipid mixture having different nucleic acid:lipid molar ratios to optimize the nucleic acid:lipid ratio. Suitable molar ratios of invention lipid:colipid are about 0.1:1 to 1:0.1, 0.2:1 to 1:0.2, 0.4:1 to 1:0.4, or 0.6:1 to 1:0.6. One optionally uses a lipid:colipid ratio of about 1:1. Lipid particle preparations containing varying molar proportions of colipid deliver different amounts of nucleic acid to transfected cells as the proportion of colipid varies.

The amount of polyanion, present as an oligonucleotide, delivered to a representative cell by at least some of the lipids appears be similar to or greater than the amount delivered by commercially available transfection lipids {Lipofectin™ (Gibco/BRL), Transfectam™ (Promega) or Lipofectamine™ (Gibco/BRL)} for some cell lines where comparisons were made. The difference in transfection efficiency between lipids described herein and commercially available lipids is observed when the transfections are done in the presence of medium containing serum. The amount of polyanion delivered into cells was estimated to be about 2- to 100-fold greater for lipids of structure $\underline{A}$ based on the observed fluorescence intensity of transfected cells after transfection using a fluorescently labeled oligonucleotide. The cationic lipids described herein also transfect some cell types that are not detectably transfected by commercial lipids, particularly where the transfection is conducted in the presence of serum.

The cationic lipids described herein also differed from commercially available lipids by efficiently delivering a polyanion (oligonucleotide) into cells in tissue culture over a range of cell confluency from about 50 to 100%. Most commercially available lipids require cells that are at a relatively narrow confluency range for optimal transfection efficiency. For example, Lipofectin™ requires cells that are 70–80% confluent for transfecting the highest proportion of cells in a population. The invention lipids could be used to transfect cells that are about 10–50% confluent, but toxicity of the lipids was more pronounced, relative to that seen using cells that are about 50–100% confluent. In general, the invention lipids transfected cells that were about 60–100% confluent with minimal toxicity and optimal efficiency. Confluency ranges of 60–95% or 60–90% are thus convenient for transfection protocols with most cell lines in tissue culture.

The invention cationic lipids complexed with an oligonucleotide were used to transfect cells in tissue culture. The lipids are optionally complexed with expression vector nucleic acid(s) or nucleic acids encoding only polypeptides whose expression is desired, e.g., plasmid DNA, and used to transfect cells in vitro or in animals in vivo, e.g., non-human primates, mice or rats, or in humans. The RNA and the DNA encoded gene products would be expressed in or incorporated into the transfected cells.

Liposomes or complexes consisting of the invention cationic lipids and an optional colipid are typically prepared by first drying the lipids in solvent (usually chloroform) under reduced pressure (spin vac in 1.5 mL polypropylene tubes for small volumes (about 100 µL) or rotovap in round bottom flasks for larger volumes, e.g. 10 mL in 100 mL flask). One then hydrates the lipids and converts the lipids to liposomes or lipid complexes by adding water or low ionic strength buffer (less than about 200 mM total ion concentration) followed by agitating (by vortexing and/or sonication) and/or freeze/thaw treatments.

Without being bound to any theory, the inventors believe the invention lipid-polyanion complexes form micelles or liposomes and/or amorphous complexes when formulated with polyanions or anionic compounds. Such complexes may comprise micelles, unilamellar vesicles and/or multi-lamellar vesicles. The size of the complexes is likely to be similar to that observed for other liposomes or lipid complexes, i.e., about 40 to 2000 nm in diameter, usually about 60–600 nm in diameter, depending on the manner in which one prepares the complexes. The invention lipid complexes are optionally prepared by sonication and/or vortexing and then filtered using, for example, 200, 100 or 50 nm filters to obtain particles less than about 200 nm in diameter, less than about 100 nm or less than about 50 nm respectively. One optionally prepares the lipid-polyanion complexes without using any means to size them, e.g., by about 5–10 cycles of freezing on dry ice and thawing in a water bath or in air at room temperature, optionally followed by vortexing the lipid in solution for about 3–10 minutes prior to adding a therapeutic agent, anion or polyanion. Transfection efficiency using filtered preparations to deliver a nucleic acid (or other molecules) can vary with regard to both the proportion of cells transfected and the amount of nucleic acid delivered per cell. Sonicating cationic lipid-colipid mixtures will usually provide smaller micelles and vortexing will usually provide larger micelles (Felgner *J. Biol. Chem.* (1994) 269:2550–2561). The inventors believe that the lipid-polyanion complexes or micelles transfer the therapeutic agent, anion or polyanion into the cytoplasm of a eukaryotic or prokaryotic cell by pinocytosis, endocytosis and/or by direct fusion with the plasma membrane.

The lipid-polyanion complexes of this invention are optionally used to transfect one or more cell lines or administered in vivo to animals to determine the efficiency of transfection obtained with each preparation. The invention lipid-colipid complexes in tissue culture medium, usually containing serum, e.g., fetal bovine serum (FBS), are usually used at a concentration between about 0.5 and 20 µg/mL for tissue culture transfections, with typical transfections using about 1.0 to 15 µg lipid per mL of medium. If one uses a nucleic acid that encodes a polypeptide, it also may encode a selectable (such as neomycin phosphotransferase or thymidine kinase) or detectable (such as β-galactosidase) marker or gene that will serve to allow measuring or estimating the efficiency of transfection. Polyanions will usually have at least four negative charges per molecule, usually at least 8, to facilitate complex formation with the positively charged cationic lipid. In general, oligonucleotides will have at least about 6–15 or more charges to facilitate complex formation, i.e., will be 7-mers or longer (often 7-mers to 21-mers). When using the invention complexes to deliver polyanionic compounds to cells in vivo, by e.g., intravenous injection, one will typically use liposomes or micelles having average diameters of less than about 2 µm and usually average diameters of about 100–300 nm to reduce or avoid embolism caused by the liposomes. One will usually use filters of the appropriate pore size to obtain the desired liposome size range.

As used herein, polynucleotide means single stranded or double stranded DNA or RNA, including for example, oligonucleotides (which as defined herein, includes DNA, RNA and analogs of DNA or RNA) and plasmids. In general, relatively large nucleic acids such as plasmids or mRNAs will carry one or more genes that are to be expressed in a transfected cell, while comparatively small nucleic acids, i.e., oligonucleotides, will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein or glycoprotein. Exemplary RNAs include ribozymes and antisense RNA sequences that are complementary to a target RNA sequence in a cell.

Polynucleotides include single stranded unmodified DNA or RNA comprising (a) the purine or pyrimidine bases guanine, adenine, cytosine, thymine and/or uracil; (b) ribose or deoxyribose; and (c) a phosphodiester group that linkage adjacent nucleoside moieties. Polynucleotides include oligonucleotides which typically comprise 2 to about 100 or 3 to about 100 linked nucleosides. Typical oligonucleotides comprise size ranges such as 2–10, 2–15, 2–20, 2–25, 2–30, 7–15, 7–20, 7–30 or 7–50 linked nucleotides. Oligonucleotides can be linear, circular, branched or double-stranded. Oligonucleotides are usually linear with uniform polarity but, when regions of inverted polarity are present, such regions comprise no more than one polarity inversion per 10 nucleotides. One inversion per 20 nucleotides is typical. Antisense oligonucleotides generally will comprise a sequence of about 7–50 bases, usually about 8–30 bases. The oligonucleotide base sequence is usually complementary or substantially complementary to a cognate DNA or RNA base sequence present in the cell. The size of nucleic acid that is delivered into a cell using the invention lipids is limited only by the size of molecules that reasonably can be prepared and DNA or RNA that is about 0.1 to 1 Kilobase (Kb), 1 to 20 Kb, 20 Kb to 40 Kb or 40 Kb to 1,000 Kb in length can be delivered into cells.

Polynucleotides also include DNA or RNA comprising one or more covalent modifications. Covalent modifications include (a) replacement of the phosphodiester group with a nonphosphorus moiety such as —O—CH$_2$—O—, —S—CH$_2$—O— or —O—CH$_2$—S—, and (c) replacement of the phosphodiester group with a phosphate analog such as —O—P(S)(O)—O— (phosphorothioate linkage), —O—P(S)(S)—O—, —O—P(CH$_3$)(O)—O— or —O—P(NHR$^{13}$)(O)—O— where R$^{13}$ is alkyl (C$_{1-6}$), or an alkyl ether (C$_{1-6}$). Oligonucleotides include modified oligonucleotides having a substitution at about 20–100%, more often about 40–100% and usually about 80%–100% of the phosphodiester groups in unmodified DNA or RNA. Such modified oligonucleotides optionally also have 20–100%, more often about 40–100% or about 80%–100% of the pyrimidine bases substituted with 5-(1-propynyl)uracil or 5-(1-propynyl) cytosine. Oligonucleotides include covalent modification or isomers of ribose or deoxyribose such as morpholino, arabinose, 2'-fluororibose, 2'-fluoroarabinose, 2'-O-methylribose or 2'-O-allylribose. Oligonucleotides and methods to synthesize them have been described (for example see: PCT/US90/03138, PCT/US90/06128, PCT/US90/06090, PCT/US90/06110, PCT/US92/03385, PCT/US91/08811, PCT/US91/03680, PCT/US9 1/06855, PCT/US91/01141, PCT/US92/10115, PCT/US92/10793, PCT/US93/05110, PCT/US93/05202, PCT/US92/04294, US94/04013, WO86/05518, WO89/12060, WO91/08213, WO90/15065, WO91/15500, WO92/02258, WO92/20702, WO92/

20822, WO92/20823, U.S. Pat. No. 5,214,136 and Uhlmann et al. *Chem. Rev.* 90:543, 1990).

Linkage means a moiety suitable for coupling adjacent nucleomonomers and includes both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide. Linkages between the 5' and 2' positions will usually not contain phosphorus.

A purine or pyrimidine base means a heterocyclic moiety suitable for incorporation into an oligonucleotide. It can be in the α or β anomer configuration. Purine or pyrimidine bases are moieties that bind to complementary nucleic acid sequences by Watson-Crick or Hoogsteen base pair rules. Bases need not always increase the binding affinity of an oligonucleotide for binding to its complementary sequence at least as compared to bases found in native DNA or RNA. However, such modified bases preferably are not incorporated into an oligomer to such an extent that the oligonucleotide is unable to bind to complementary sequences to produce a detectably stable duplex or triplex. Purine or pyrimidine bases usually pair with a complementary purine or pyrimidine base via 1, 2 or 3 hydrogen bonds. Such purine or pyrimidine bases are generally the purine, pyrimidine or related heterocycles shown in formulas G–I.

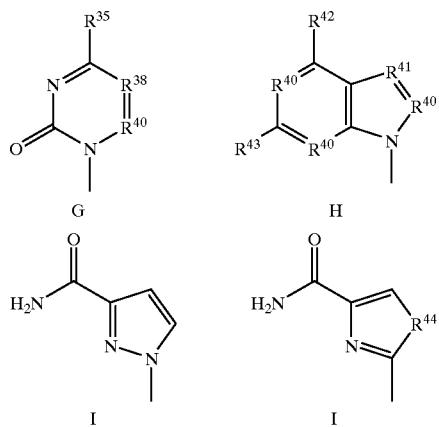

wherein $R^{35}$ is H, OH, F, Cl, Br, I, $OR^{36}$, SH, $SR^{36}$, $NH_2$, or $NHR^{37}$;

$R^{36}$ is $C_1$–$C_6$ alkyl (including $CH_3$, $CH_2CH_3$ and $C_3H_7$), $CH_2CCH$ (2-propynyl) and $CH_2CHCH_2$;

$R^{37}$ is $C_1$–$C_6$ alkyl including $CH_3$, $CH_2CH_3$, $CH_2CCH$, $CH_2CHCH_2$, $C_3H_7$;

$R^{38}$ is N, CF, CCl, CBr, CI, $CR^{39}$ or $CSR^{39}$, $COR^{39}$;

$R^{39}$ is H, $C_1$–$C_9$ alkyl, $C_2$–$C_9$ alkenyl, $C_2$–$C_9$ alkynyl or $C_7$–$C_9$ aryl-alkyl unsubstituted or substituted by OH, O, N, F, Cl, Br or I including $CH_3$, $CH_2CH_3$, $CHCH_2$, CHCHBr, $CH_2CH_2Cl$, $CH_2CH_2F$, $CH_2CCH$, $CH_2CHCH_2$, $C_3H_7$, $CH_2OH$, $CH_2OCH_3$, $CH_2OC_2H_5$, $CH_2OCCH$, $CH_2OCH_2CHCH_2$, $CH_2C_3H_7$, $CH_2CH_2OH$, $CH_2CH_2OCH_3$, $CH_2CH_2OC_2H_5$, $CH_2CH_2OCCH$, $CH_2CH_2OCH_2CHCH_2$, $CH_2CH_2OC_3H_7$;

$R^{40}$ is N, CBr, Cl, CCl, CH, $C(CH_3)$, $C(CH_2CH_3)$ or $C(CH_2CH_2CH_3)$;

$R^{41}$ is N, CH, CBr, $CCH_3$, CCN, $CCF_3$, CC≡CH or $CC(O)NH_2$;

$R^{42}$ is H, OH, $NH_2$, SH, $SCH_3$, $SCH_2CH_3$, $SCH_2CCH$, $SCH_2CHCH_2$, $SC_3H_7$, $NH(CH_3)$, $N(CH_3)_2$, $NH(CH_2CH_3)$, $N(CH_2CH_3)_2$, $NH(CH_2CCH)$, $NH(CH_2CHCH_2)$, $NH(C_3H_7)$ or F, Cl, Br or I;

$R^{43}$ is H, OH, F, Cl, Br, I, $SCH_3$, $SCH_2CH_3$, $SCH_2CCH$, $SCH_2CHCH_2$, $SC_3H_7$, $OR^{16}$, $NH_2$, or $NHR^{37}$; and $R^{44}$ is O, S or Se.

Exemplary bases include adenine, cytosine, guanine, hypoxanthine, nosine, thymine, uracil, xanthine, 2-aminopurine, 2,6-diaminopurine, 5-(4-methylthiazol-2-yl)uracil, 5-(5-methylthiazol-2-yl)uracil, 5-(4-methylthiazol-2-yl)cytosine, 5-(5-methylthiazol-2-yl)cytosine and the like.

Also included are alkylated or alkynylated bases having substitutions at, for example, the 5 position of pyrimidines that results in a pyrimidine base other than uracil, thymine or cytosine, i.e., 5-methylcytosine, 5-(1-propynyl)cytosine, 5-(1-butynyl)cytosine, 5-(1-butynyl)uracil, 5-(1-propynyl)uracil and 7-(1-propynyl)-7-deazaguanine. Base analogs and their use in oligomers have been described (see for example, U.S. application Ser. No. 08/123,505; US92/10115; US91/08811; US92/09195; WO 93/10820; WO 92/09705; WO 92/02258; Nikiforov, T. T., et al, *Tet Lett* (1992) 33:2379–2382; Clivio, P., et al, *Tet Lett* (1992) 33:65–68; Nikiforov, T. T., et al, *Tet Lett* (1991) 32:2505–2508; Xu, Y. -Z., et al, *Tet Lett* (1991) 32:2817–2820; Clivio, P., et al, *Tet Lett* (1992) 33:69–72; Connolly, B. A., et al, *Nucl Acids Res* (1989) 17:4957–4974). Oligonucleotides having varying amounts of bases analogs such as 5-methylcytosine, 5-(1-propynyl)cytosine, 5-(1-butynyl)cytosine or 5-(1-butynyl) uracil, 5-(1-propynyl)uracil or 7-(1-propynyl)-7-deazaguanine, e.g., about 20–80%, usually about 80–100% of the natural bases are substituted with the corresponding analogs.

Nucleic acids complexed with the invention lipids will optionally comprise nucleic acids encoding a polypeptiie useful for therapeutic or diagnostic uses. Examples of such polypeptides include histocompatibility antigens, cell adhesion molecules, cytokines, antibodies, antibody fragments, cell receptor subunits, cell receptors, intracellular enzymes (e.g., luciferase, β-galactosidase, thymidine kinase) and extracellular enzymes or a fragment of any of these. The nucleic acids also may optionally comprise expression control sequences and generally will comprise a transcriptional unit comprising a transcriptional promoter, an enhancer, a transcriptional terminator, an operator or other expression control sequences.

Polynucleotides (i.e., nucleic acids, oligonucleotides or oligonucleotide analogs) used to form complexes for transfecting a cell may be present as more than one expression vector and/or more than one oligonucleotide. Thus, 1, 2, 3 or more different expression vectors and/or oligonucleotides are delivered into a cell as desired. Expression vectors will typically express 1, 2 or 3 genes when transfected into a cell, although many genes may be present such as when a herpes virus vector or a yeast artificial chromosome is delivered into a cell. The ratio of each polynucleotide in a lipid complex relative to each other can be selected as desired. Expression vectors that are introduced into a cell can encode selectable markers (*E coli* neomycin phosphotransferase, thymidine kinase from a herpesvirus (Freeman et al. *Cancer Res.* 53:5274–5283, 1993, Freeman et al. *Seminars Oncol.* 23:31–45, 1996), *E coli* xanthine-guanine phosphoribosyltransferase, and the like) or biologically active proteins such as angiogenesis agonists or antagonists, metabolic enzymes or functional proteins (such as immunoglobulin genes, cell receptor genes, cytokinies (such as IL-2, IL-4, G-CSF, GM-CSF, γ-INF and the like), genes that encode enzymes that mediate purine or pyrimidine metabolism and the like).

Methods to prepare lipid-nucleic acid complexes and methods to introduce the complexes into cells in vitro and in vivo have been described (see for example, U.S. Pat. No. 5,283,185; U.S. Pat. No. 5,171,678; WO 96/01841; WO 96/01840; WO 94/00569; WO 93/24640; WO 91/16024; Felgner *J. Biol. Chem.* 269:2550–2561, 1994; Nabel *Proc. Natl. Acad. Sci.* (U.S.A.) 90:11307–11312, 1993; Nabel *Human Gene. Ther.* 3:649, 1992; Gershon *Biochem.* 32:7143, 1993; Strauss *EMBO J.* 11:417, 1992). The invention lipids of structure $\underline{A}$ form a complex with anionic compounds or polyanions such as nucleic acids or peptides having negative charges at least through attraction between the positively charged lipid and the negatively charged polyanion. Hydrophobic interactions between the cationic lipids and the hydrophobic substituents in the polyanion such as aromatic and alkyl groups may also facilitate complex formation between anionic and other type of molecules, e.g., hydrophobic therapeutic molecules.

The invention lipids are suitable for high efficiency transfection of cells in vivo with polyanions such as oligonucleotides, plasmids or peptides. We have found that lipid-oligonucleotide complexes which we prepared using no fusogenic colipid such as DOPE efficiently delivered lipid into the cell cytoplasm of cells in a host mammal, i.e., mouse. Previously described studies found that reticuloendothelial cells, e.g., monocytes and macrophages, rapidly remove lipid complexes or liposomes from systemic circulation (Fidler et al. *Lymphokines* 3:345–363, 1981, Poste et al. *Cancer Res.* 42:1412–1422, 1982). These cells are efficient scavengers of foreign particulate matter in the systemic circulation or tissues and large numbers of these cells are usually present in the lung to clear the lung of foreign objects.

The invention lipids are usually prepared without a colipid when used to deliver compounds into cells in a host animal in vivo, while a colipid is usually present when the lipids are used to transfect cells in tissue culture in vitro. Results obtained using GS 3793, structure shown below, without colipid indicated that the lipid-oligonucleotide complexes evaded the reticuloendothelial system and efficiently delivered oligonucleotide into the nucleus of cells in tissues, e.g., the lung and spleen. The finding of oligonucleotide in lung cell nuclei indicated that significant amounts of the injected lipid-oligonucleotide complexes bypassed reticuloendothelial cells to reach cells of the lung and other organs. This result indicates that 3793 is suitable for delivering compounds into the cytoplasm of cells in vivo. The invention lipids can thus be used to target or deliver drugs to particular target organs, e.g., they can be used to deliver a an enzyme such as DNase to the lung of patients with cystic fibrosis.

The invention cationic lipids efficiently deliver oligonucleotides and plasmids to cells in tissue culture. The lipid GS 3793 formulated with a colipid, e.g., DOPE, delivered about 10-fold more plasmid to cells than GS 2888. When GS 3793 was formulated without colipid, the lipid delivered about 6-fold less oligonucleotide to cells than GS 2888 in comparable transfections. All of these transfections were done in the presence of serum in the tissue culture medium.

Complexes between the invention lipids and anionic therapeutic agents are generally prepared using a lipid:therapeutic agent charge ratio in the range of about 0.1:1 to about 100:1, typically about 1:1 to about 50:1, usually about 5:1 to about 25:1. One determines optimal charge ratios by preparing complexes containing different charge ratios and then testing the different preparations for their efficiency at delivering the therapeutic agent into cells in vitro or in vivo using these charge ratio ranges.

Applications

The invention lipids are useful for delivering polyanions, polypeptides or nucleopolymers into cells. The invention lipids can be used to deliver an expression vector into a cell for manufacturing or therapeutic use. The expression vectors can be used in gene therapy protocols to deliver a therapeutically useful protein to a cell or for delivering nucleic acids encoding molecules that encode therapeutically useful proteins or proteins that can generate an immune response in a host for vaccine or other immunomodulatory purposes according to known methods (see for example, U.S. Pat. Nos. 5,399,346, 5,336,615, WO 94/21807, WO 94/12629). The vector-transformed cell can be used to produce commercially useful cell lines, such as a cell line for producing therapeutic proteins or enzymes (e.g., erythropoietin), growth factors (e.g., human growth hormone, G-CSF, GM-CSF or interleukins) or other proteins. The invention lipid-nucleic acid complexes can be used to construct cell lines for gene therapy applications in subjects such as humans or other species including murine, feline, bovine, equine, ovine or non human primate species. The invention lipids can be used in the presence of serum and will thus deliver polyanions into cells in tissue culture medium containing serum in vitro or in an animal in vivo.

The invention lipids complexed with nucleopolymers can be used in antisense inhibition of gene expression in a cell by delivering an antisense oligonucleotide into the cell (see for example, Wagner et al. *Science* (1993) 260:1510; WO 93/10820). Such oligonulcleotides will generally comprise a base sequence that is complementary or substantially complementary (having 1 mismatch per 12–20 base pairs) to a target RNA sequence that the cell expresses. However, the oligomer may regulate intracellular gene expression by binding to an intracellular nucleic acid binding protein (Clusel et al. *Nucl. Acids Res.* (1993) 21:3405) or by binding to an intracellular protein or organelle that is not known to bind to nucleic acids (WO 92/14843, U.S. Pat. No. 5,523, 389). A cell that is blocked for expression of a specific gene(s) is useful for manufacturing and therapeutic applications. Exemplary manufacturing uses include inhibiting protease synthesis in a cell to increase production (i.e., reduce target protein degradation caused by the protease) of a protein for a therapeutic or diagnostic application. Exemplary therapeutic applications include inhibiting synthesis of cell surface antigens (histocompatibility antigens, such as MHC class II genes, and the like) to reduce rejection and/or to induce immunologic tolerance of the cell either after it is implanted into a subject or when the cell is transfected in vivo.

The invention lipids can be dehydrated in the presence of sugars such as sucrose or trehalose (see e.g., U.S. Pat. No. 4,880,635) or otherwise formulated with anionic, zwitterionic and lipophilic therapeutic agents including anticancer agents such as doxorubicin, a lipophilic compound, to obtain complexes comprising the invention lipids and a therapeutic agent(s). The invention lipids can be formulated with known antiviral agents such as HPMPC, (9-(3-hydroxy-2-phosphonylmethoxy)propyl)cytosine) PMEA, (9-(2-phosphonylmethoxy)ethyl)adenine) PMEG, (9-(2-phosphonylmethoxy)ethyl)guanine) PMPA, (9-(2-phosphonomethoxy)propyl)adenine), AZT, 3TC and their derivatives (see eg., WO 91/16320, EP 481 214, EP 398 231, EP 454 427, U.S. Pat. Nos. 5,360,817, 5,302,585, 5,208,221, 5,142,051, 4,808,817, 4,724,233, 4,659,825, U.S. patent application Ser. No. 08/606,624, PCT Application Nos. US96/02882, US93/07360) to obtain lipid complexes with the antiviral agent. The invention lipids can be formulated with polyene antibiotics such as amphotericin B. Such formulations are useful for delivering the therapeutic agents into the cytoplasm of cells in vitro or in vivo. Complexes consisting of an invention cationic lipid and an anti-influenza agent (see e.g., WO 91/16320, U.S. Pat. Nos. 5,360,817, PCT Application No. US96/02882) can be used to deliver the antiviral agent to the lung, the primary site of infection. These complexes can be prepared by any of the techniques now known or subsequently developed for preparing lipid complexes containing therapeutic agents.

EXAMPLES

The following examples further illustrate but do not limit the invention.

Representative compounds that were synthesized are shown below.

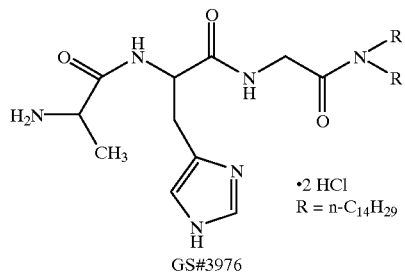

•2 HCl
R = n-C$_{14}$H$_{29}$

GS#3976

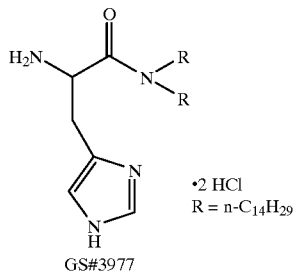

•2 HCl
R = n-C$_{14}$H$_{29}$

GS#3977

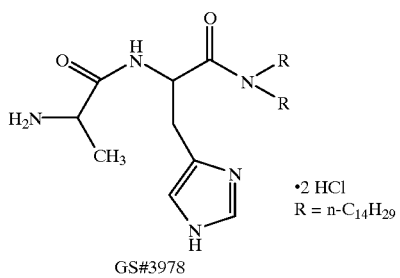

•2 HCl
R = n-C$_{14}$H$_{29}$

GS#3978

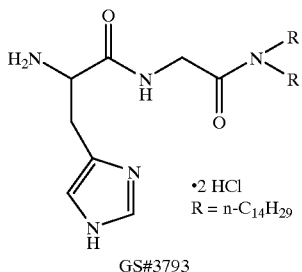

•2 HCl
R = n-C$_{14}$H$_{29}$

GS#3793

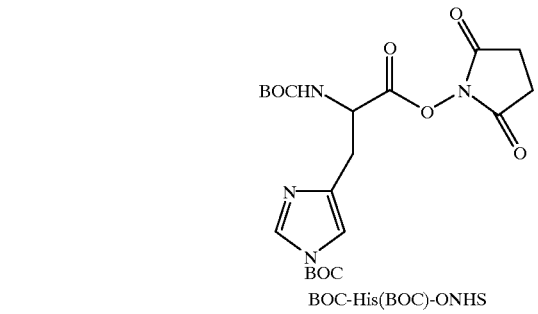

BOC-His(BOC)-ONHS

+ H$_2$NCH$_2$C(O)N(R)$_2$
816-80

908-167

HCl / dioxane

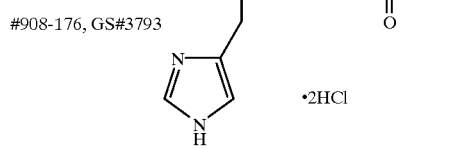

908-176, GS#3793

•2HCl

Synthesis of GS#3793 (908-176)

Compound 908-167: A methylene chloride solution (10 mL) of BOC-His(BOC)-ONHS (0.2 g, 0.44 mmole), #816-80 (0.2 g, 0.4 mmole) and TEA (67 mg, 0.66 mmole) was stirred at room temperature overnight. The reaction mixture was washed with a saturated NaHCO₃ aqueous solution, dried and purified by flash column chromatography, affording 225 mg, 63%, of 908-167. ¹H NMR (CDCl₃): δ 8.00 (d, 1H, J=0.9 Hz), 7.36 (b, 1H), 7.16 (s, 1H), 6.08 (d, 1H, J=7.3 Hz), 4.51 (b, 1H), 3.98 (d, 2H, J=3.7 Hz), 3.30 (dd, 2H, J=7.5 J=3.6 Hz), 3.10–3.18 (m, 3H), 3.00 (dd, 1H, J=4.93, J=5.79 Hz), 1.63 (s, 9H), 1.10–1.65 (2s+m, 66H), 0.88 (t, 6H, J=6.4 Hz).

Compound 908-176 (GS 3793): Compound 908-167 (210 mg) was treated with 2 N HCl in 1,4-dioxane (3 mL) at room temperature for 3 hr, concentrated to dryness yielding #908-176 as a white solid. ¹H NMR (DMSO-d₆): δ 14.3 (b, 1H), 9.01 (s, 1H), 8.83 (t, 1H, J=4.5 Hz), 8.38 (b, 3H), 7.48 (s, 1H), 4.25 (m, 1H), 4.12 (dd, 1H, J=17.2 Hz, J=5.4 Hz), 3.95 (dd, 1H, J=16.6 Hz, J=4.5 Hz), 3.10–3.50 (m, 6H+H₂O), 1.00–1.60 (m, 48 H), 0.88 (t, 6H, J=6.4 Hz).

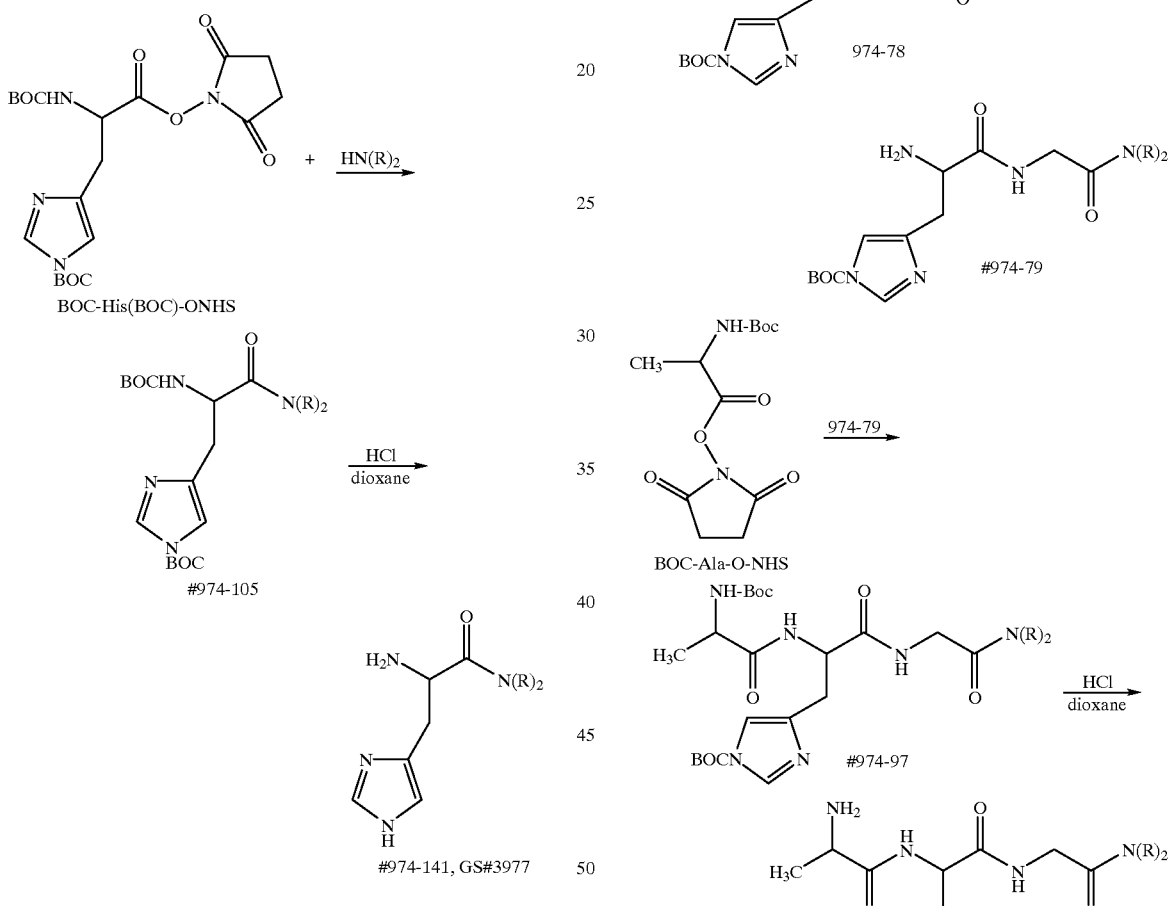

Synthesis of GS#3977 (974-141)

Compound 974-105: A methylene chloride solution (5 mL) of BOC-His(BOC)-ONHS (108 mg, 0.24 mmole), dimyristylamine (89 mg, 0.22 mmole, example 2) and TEA (24 mg, 0.24 mmole) was stirred at room temperature for 5 hrs. The reaction mixture was dilution with CH₂Cl₂ (10 mL), washed with saturated NaHCO₃ aqueous solution, dried, and purified by flash column chromatography giving 95 mg, 58.6% of product. ¹H NMR (CDCl₃): δ 7.98 (s, 1H), 7.14 (s, 1H), 5.36 (d, 1H, J=8.8 Hz), 4.78–4.90 (m, 1H), 2.70–3.55 (m, 6H), 1.60 & 1.39 (2s), 0.88 (t, 6 H, J=6.1 Hz).

974-141 (GS#3977): 974-105 (34 mg) was treated with 2N HCl in 1,4-dioxane at room temperature for 5 hrs and concentrated to dryness. ¹H NMR (DMSO-d₆): δ 9.05 (s, 1H), 8.38 (b, 1H), 7.41 (s, 1H), 4.55 (b, 1H), 0.88 (t, 6H).

Synthesis of GS#3976 (974-140)

Compound 974-79: A CH₂Cl₂ solution (5 mL) of FMOC-His (Boc)-Opf (140 mg, 0.22 mmole), 816-80 (100 mg, 0.21 mmole) and TEA (22 mg, 0.22 mmole) was stirred at room temperature for 2 hr, worked up and purified by flash column chromatography affording 164 mg, 82.8% of product, 974-78. The FMOC protected compound was dissolved in CH₂Cl₂ (25 mL) and treated with DBU (1,8-diazabicyclo [5.4.0.]undec-7-ene) (65 mg, 0.43 mmole) for 10 min., then washed with saturated NaCl aqueous solution, dried, and purified by column chromatography giving 109 mg, 88% of 974-79. $^1$H NMR (CDCl$_3$): δ 8.10 (t, 1H), 7.99 (s, 1H), 7.19 (s, 1H), 3.92–4.15 (dd, 2H), 3.65–3.86 (m, 4H), 3.30 (t, 2H), 3.02–3.20 (m, 3 H), 2.70–2.82 (m, 1H), 1.58 (s), 0.85 (t, 6H, J=6.4 Hz).

974-97: A CH$_2$Cl$_2$ solution (5 mL) of Boc-Ala-ONHS (20 mg, 70 μmole), 974-79 (44 mg, 63.5 μmole) and TEA (7 mg, 70 μmole) was stirred for 5 hr at room temperature. After normal work-up and purification, the reaction gave 32.8 mg, 60%, of 974-97. $^1$H NMR (CDCl$_3$): δ 7.98 (s, 1H), 7.78 (d, 1H, J=7.1 Hz), 7.32 (t, 1H), 7.17 (s, 1H), 5.20–5.29 (b, 1H), 4.73 (q, 1H), 4.20–4.30 (m, 1H), 3.95 (d, 2H, J=3.8 Hz), 3.30 (t, 2H), 2.90–3.20 (m, 4H), 1.60 & 1.43 (2s), 0.87 (t, 6H, J=6.4 Hz).

974-140 (#GS3976): 33.4 mg of 974-97 was treated with 2N HCl in 1,4-dioxane at room temperature for 4 hrs, concentrated to dryness. $^1$H NMR (DMSO-d$_6$): δ 8.90 (s, 1H), 8.82 (d, 1H), 8.30 (t, 1H), 7.44 (s, 1H).

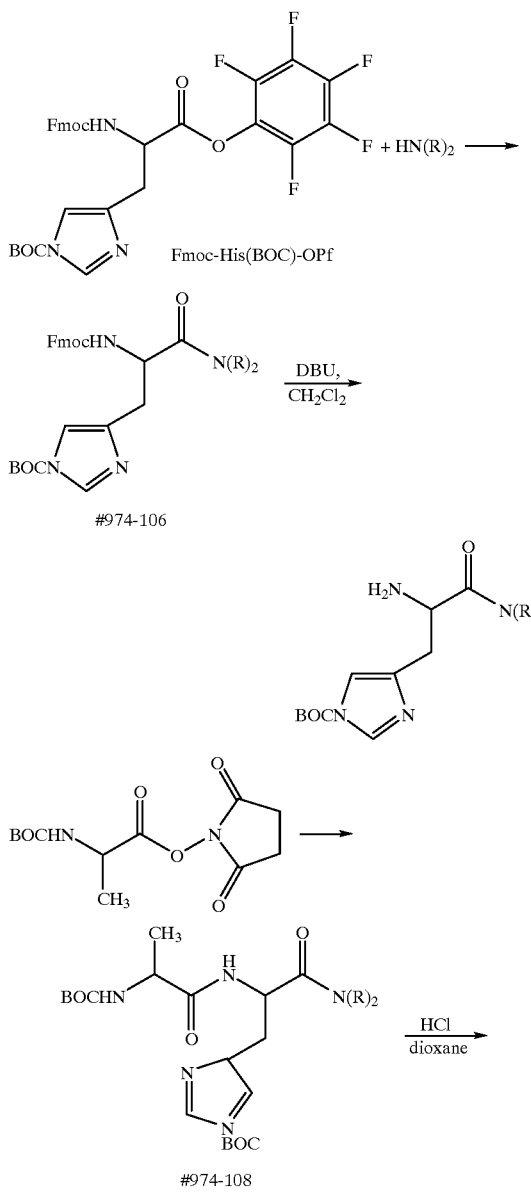

974-106

974-108

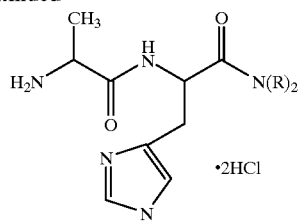

974-142, GS#3978

Synthesis of GS#3978 (974-142)

Compound 974-106: A CH$_2$Cl$_2$ solution (5 mL) of FMOC-His(Boc)-Opf (138 mg, 0.215 mmole), dimyristylamine (80 mg, 0.195 mmole) and TEA (21.8 mg, 0.215 mmole) was stirred at room temperature for 4 hrs. After normal work-up and purification, the reaction yield 77.6 mg of 974-106. $^1$H NMR (CDCl$_3$): δ 8.02 (s, 1H), 7.78 (d, 2H), 7.55–7.64 (m, 2H), 7.40 (t, 2H), 7.30 (t, 2H), 7.18 (s, 1H), 5.79 (d, 1H, J=8.0 Hz), 4.80–5.05 (m, 1H), 4.05–4.45 (m, 3H), 2.80–3.65 (m, 6H), 1.60 (s), 0.88 (t, 6H).

974-108: A CH$_2$Cl$_2$ solution (4 mL) of 974–106 (77 mg) and DBU (57 mg, 0.375 mmole) was stirred for 20 min. The reaction mixture was diluted with CH$_2$Cl$_2$ (10 mL), washed with saturated NaHCO$_3$ aqueous solution, dried. The residue was redissolved in CH$_2$Cl$_2$ (4 mL) and reacted with Boc-Ala-ONHS (30-mg, 0.105 mmole), TEA (10.8 mg, 0.106 mmole) for 4 hrs. After purification, 8.8 mg of 974-108 was obtained. $^1$H NMR (CDCl$_3$): δ 7.96 (s, 1H), 7.12 (s, 1H), 6.89 (d, 1H, J=8.5 Hz), 5.19–5.24 (m, 1H), 5.14 (q, 1H), 4.14–4.21 (m, 1H), 2.80–3.55 (m, 6H). 1.61 & 1.44 (2s), 0.88 (t, 6H, J=6.4 Hz).

GS# 3978 (974-142): 8.8 mg of #974-108 was treated with 2 N HCl in 1,4-dioxane at room temperature for 4 hrs, concentrated to dryness to yield 974-142.

Example 2

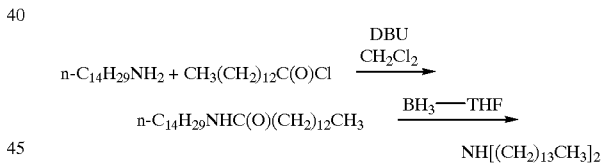

Synthesis of Dimyristylamine

N-myristyl myristamide Myristoyl chloride (2.5 g; 10 mmole) was added to a room temperature methylene chloride solution of n-tetradecylamine (2.1 g; 10 mmole, TCI chemicals) and DBU (2.3 g; 15 mmole). The resulting mixture was stirred at room temperature for 4 hours, diluted with CH$_2$Cl$_2$, washed with brine solution, dried, and purified by column chromatography on silica gel, to give 3.40 g, 80.9% of product. $^1$H NMR (CDCl$_3$): δ 5.38 (6s, 1H), 3.24 (q, 2H), 2.16 (t, 2H, J=7.8 Hz), 1.58–1.66 m, 2H), 1.40–1.57 (m, 2H), 1.20–1.40 (m, 42H), 0.89 (t, 6H).

Dimyristylamine ((n-C$_{14}$H$_{29}$)$_2$NH). N-myristyl myristamide (0.90 g; 2.1 mmole) was treated with borane THF (5 mL of 1 M solution, 5.0 mmole) and reacted at reflux for 3 hrs. The reaction mixture was carefully neutralized with 3N HCl aqueous solution and stirred at 50° C. for 20 min., the back neutralized with 2N NaOH aqueous solution. The mixture was concentrated, then partitioned between CH$_2$Cl$_2$ and saturated NaHCO$_3$ aqueous solution, dried and concentrated, affording 0.93 g of product. NMR (CDCl$_3$): δ

2.59 (t, 2H, J=7.2 Hz), 1.40–1.55 (m, 2H), 1.15–1.40 (m, 22H), 0.88 (t, 3H, J=6.8 Hz).

Example 3

Synthesis of GS #3906 (KYL#974-82):

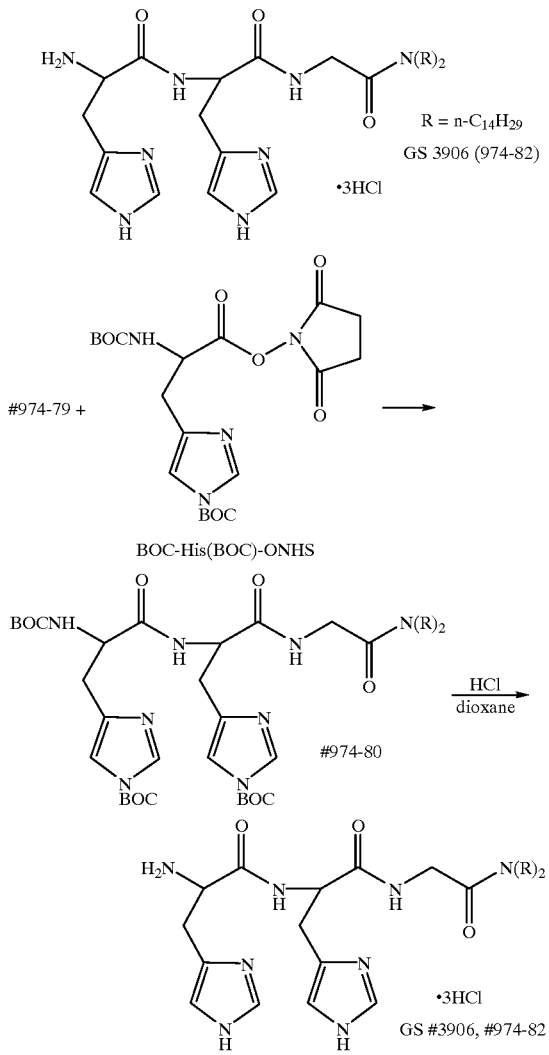

974-80: A methylene chloride solution (5 ml) of BOC-His (BOC)-ONHS (36 mg; 79 μmole), #974-79 (50 mg; 72 μmole) and TEA (8 mg; 79 μmole) was stirred at room temperature for 2 hrs. The reaction mixture was diluted with CH$_2$Cl$_2$ and washed with saturated NaHCO$_3$ aqueous solution; the organic solution was isolated, dried, and purified by flash column chromatography on silica gel, yielding 30.0 mg, 40.3% of product #974-80. $^1$H NMR (CDCl$_3$): δ 7.90–8.05 (2S+b, 4H), 7.16+7.19 (2S, 2H), 5.90 (d, 1H), 4.74 (q, 1H), 4.45 (m, 1H), 4.0 (q, 2H), 3.25 (t, 2H), 2.86–3.19 (m, 7H).

GS #3906 (#974- 82): A mixture of #974-80 (12 mg), and 2N HCl (3 mL) was stirred at room temperature for 3 hrs. The reaction mixture was concentrated to dryness affording the lipid GS#3906, 974-82.

Example 5

Preparation of lipid-nucleic acid complexes and cell transfection. Lipids were prepared for complexing with nucleic acids by drying a cationic lipid-colipid mixture in CHCl$_3$ under argon. The molar ratio of cationic lipid to colipid was adjusted by adding appropriate amounts of each lipid in CHCl$_3$ together prior to drying. Usually 10 mL of water was added to a 100 mL round bottom flask containing a dried film of lipid and colipid. The lipids consisted of a mixture of an invention cationic lipid and the colipid DOPE (dioleylphosphatidyl-ethanolamine). Sterile-filtered water or a low ionic strength aqueous buffer such as physiological saline, TE (10 mM tris, 1 mM EDTA, pH 7–8) or Ringer's solution was then added to the dried lipids to obtain a lipid suspension at 1 mg lipid/mL followed by a 10 minute bath sonication (Ultra Sonik 100, NEY) at room temperature to suspend the lipids in the flask. The suspended lipids (10 mL) were then sonicated 5 times for 15 seconds per sonication at 0–4° C. with about 30–60 seconds between pulses. Sonication was usually conducted in a 15 mL polypropylene culture tube. A probe sonicator (Sonifier 250, Branson Ultrasonics) was used at maximum power for the ice bath sonication and for each 15 second pulse. The lipid suspension was optionally filtered or centrifuged (2000 rpm, 10 minutes at 0–4° C.) to remove large particulate matter and the resulting lipid suspensions were kept at 4° C. until used. Alternatively, the lipid suspension was subjected to 5 cycles of freezing on dry ice and thawing in a 37° water bath.

Lipid nucleic acid complexes were prepared by mixing (a) 10% v/v (usually 100 μL) oligonucleotide in Optimem™ (Bethesda Research Labs, Inc.) at room temperature with (b) 10% v/v lipid suspension in Optimem™ at room temperature and allowing the mixture to stand for about 15 minutes, followed by adding (c) 80% v/v Optimem™ without serum or 80% v/v tissue culture medium (Modified Essential Medium (MEM), Dulbecco's Modified Eagle's Medium (DMEM), etc) containing 0–80% fetal bovine serum (Hyclone, Inc.). The lipid and nucleic acid solutions could also be prepared using DMEM without serum, a low ionic strength (less than about 200 mM total ion concentration) aqueous medium lacking phosphate (TE, etc) or water in place of Optimem™. Typically, 100 μL each of Optimem™ containing oligonucleotide (100–500 pmole) and Optimem™ containing added lipid was mixed with 800 μL of serum free Optimem™ or with 800 μL of tissue culture medium containing 10–80% FBS. Generally, 5 or 10 μL (5 or 10 μg) of lipid was added to 95 or 90 μL of Optimem™ to give a final 1 mL transfection preparation containing 5 or 10 μg of lipid and 250 pmole of oligonucleotide. The lipid-nucleic acid mixture was held at room temperature for about 15 min hours before adding medium to give the final transfection preparation volume (usually 1 mL) and warming to 37° C. and immediately applying onto the cells. The transfection mixture was left on the cells for 2 to 24 hours (at 37° C.), with a 6 hour time period commonly used.

Cells were typically transfected using 1 mL of transfection mixture per well in a 6-well plate. Cells at about 50–100% confluency were used. The efficiency of transfection was relatively uniform over this confluency range for the invention cationic lipids. Typical transfections with the invention lipids used cells at about 60–100% confluency. Other cationic lipids (Lipofectin™, Transfectam™ or Lipofectamine™) were used according to manufacturers instructions and cells were thus at recommended confluency for transfection with these lipids. Cells at a lower confluency (at least about 10% confluent) could usually be transfected with oligonucleotides using the invention cationic lipids, but more cell toxicity was observed relative to cells at 50–100% confluency. The increased toxicity is believed to be due, at least in part, to the high level of oligonucleotide that was delivered into the cells.

Nucleic acids typically used were 15-mer phosphorothioate oligonucleotides that were labeled with fluorescein at the 5' or 3' terminus using a linker of structure $NH_2(CH_2)_6$—O—P(O)(OH)—O—5' linked to the oligonucleotide at the 5' or 3' hydroxyl group. The oligonucleotide designated ODN1 was labeled at the 5' terminus and had a base sequence complementary to a region of the HSV strain 17 DNA polymerase gene at coordinates 421 to 436 (McGeoch *J Gen Virol* (1988) 69:1531). There was no known sequence that was complementary to ODN1 or ODN2 in the tested cells, except where ODN2 without the fluorescent label (ODN2A) is used, e.g., to inhibit T antigen synthesis in an antisense assay. The oligonucleotide designated ODN2 is labeled at the 3' terminus and consists of the same bases and the same base sequence as the oligonucleotide designated TAg-15 (Wagner *Science* (1993) 260:1510–1513, at page 1511, Table 1). The oligonucleotides were used at a concentration of 250 or 500 nM (i.e., 250 to 500 pmole) for typical 1 mL transfections.

Cells for transfection experiments were generally seeded onto 25 mm diameter glass cover slips in 6-well plates 12–24 hours prior to transfection and were grown under conditions recommended for each cell line. The cells were generally grown on cover slips to facilitate analysis by fluorescence microscopy. The cells were washed twice with tissue culture medium containing serum or with serum-free Optimem™, followed by adding 1 mL of the lipid-nucleic acid mixture at room temperature. The cells were incubated with the lipid-nucleic acid mixture at 37° C. for 2 to 24 hours, followed by washing the cells twice in medium containing serum. The cell washes were done by removing most of the medium from the wells, but leaving a thin layer, and adding about 1 mL of fresh medium for each wash. Removing all medium from the cells between each wash resulted in increased cell toxicity relative to washes with a thin layer of medium present at all times. Transfection efficiency and lipid toxicity was examined by fluorescence microscopy essentially as described (Wagner et al. *Science* (1993) 260:1510) shortly after the lipid-nucleic acid complex was removed, i.e., usually within about 5–60 minutes.

Transfected cell lines and their usual culture media were CV-1 (African green monkey kidney, ATCC No. CCL 70, 90% DMEM with 10% FBS), HeLa (human cervical carcinoma, ATCC No. CCL 2), WR-21 (wap-ras transgenic mouse salivary gland cell, 90% DMEM with 10% FBS), BxPC3 (primary human pancreatic adenocarcinoma, 90% RPMI with 10% FBS, A549 (human lung carcinoma, 90% DMEM with 10% FBS), MCF-7 (human pleural effusion breast adenocarcinoma, 90% Eagles MEM with 10% FBS, 1 mM sodium pyruvate and 10 μg/mL bovine insulin), HT29 (p53$^-$/Rb$^-$ human colon carcinoma, 90% DMEM with 10% FBS), RKO (p53$^+$/Rb$^+$ human colon carcinoma, 90% DMEM with 10% FBS) and NHDF (normal human dermal fibroblasts, 90% DMEM with 10% FBS). Culture media typically contained 1× penicillin and streptomycin.

Example 6

CV-1 cells were transfected for 4 hours in medium containing 10% FBS (fetal bovine serum) using 1 mL of lipid complexed with 250 pmole ODN1 for 15 minutes prior to addition to the cells on cover slips in 6-well plates. The cells were observed by fluorescence microscopy after the lipid-ODN1 complex was removed. After the lipid-ODN1 complex was removed, the cells were incubated for 5 hours in DMEM containing 10% FBS and then the proportion of cells that were transfected as shown by nuclear staining by the fluorescent labeled oligonucleotide ODN1 was determined. The results showed that the tested lipids efficiently transfected the CV-1 cell line in the presence of serum with little or no toxicity to the cells.

| lipid* | lipid** concentration | % cells** transfected | toxicity*** |
|---|---|---|---|
| 3976 | 2.5 | 5 | – |
|  | 5.0 | 10 | – |
|  | 10.0 | 15 | – |
|  | 15.0 | 50 | + |
|  | 20.0 | 50 | + |
| 3977 | 2.5 | <5 | – |
|  | 5.0 | 10 | – |
|  | 10.0 | 25 | – |
|  | 15.0 | 50 | + |
|  | 20.0 | 50 | + |
| 3978 | 2.5 | <5 | – |
|  | 5.0 | 15 | – |
|  | 10.0 | 25 | – |
|  | 15.0 | 50 | + |
|  | 20.0 | 50 | + |

*the lipids were used as a 1:1 molar lipid:colipid mixture with DOPE as the colipid
**μg lipid per mL
***(+) low toxicity with no dead cells apparent and occasional change in cell morphology; (++) significant toxicity with ≧ 40% of cells dead or dying; (–) no significant toxicity observed Example 7

CV-1 cells were transfected for 4 hours in medium containing 10% FBS (fetal bovine serum) using 1 mL of lipid complexed with 250 pmole ODN1 for 15 minutes prior to addition to the cells on cover slips in 6-well plates. The lipids were used without a colipid. Lipid GS 3906 was formulated in a similar manner in aqueous solution, but the lipid formed aggregates that did not contain oligonucleotide. The cells were observed by fluorescence microscopy after the lipid-ODN1 complex was removed. After the lipid-ODN1 complex was removed, the cells were incubated for 5 hours in DMEM containing 10% FBS and then the proportion of cells that were transfected as shown by nuclear staining by the fluorescent labeled oligonucleotide ODN1 was determined. The results showed that the tested lipids efficiently transfected the CV-1 cell line in the presence of serum with little toxicity to the cells.

| lipid | lipid* concentration | % cells transfected | toxicity** |
|---|---|---|---|
| 3976 | 15.0 | 70 | + |
| 3977 | 15.0 | 70 | + |
| 3978 | 15.0 | 70 | + |
| 3793 | 15.0 | 70 | + |

*μg lipid per mL
**(+) low toxicity with no dead cells apparent and occasional change in cell morphology; (++) significant toxicity with ≧ 40% of cells dead or dying; (–) no significant toxicity observed Example 8

Lipid preparations #1 (GS-2888:DOPE 2:1), #2 (GS-3793:DOPE 1:1) and #3 (GS-3793 no colipid) were used to transfect cells with a fluorescently labeled 15-mer oligonucleotide containing phsphorothioate linkages. The fluorescent dye fluorescein was linked to the oligonucleotide through the 5' terminal hydroxyl group using a commercial fluorescein phosphtoramidite (Clontech, Cat. No. 5235-1).

The cells were transfected for 6 hours at 37° C in medium containing 10% FBS using unsized or sized lipid preparations. All transfections used 1 mL of a solution containing 2.5 µg of lipid per mL and the amount of oligonucleotide indicated in the Table below. The stained cells were on glass cover slips in wells of 6-well tissue culture plates. The lipids were dried under vacuum, resuspended in deionized water by 6 freeze-thaw cycles, and sized preparations were filtered through 50 nm, 100 nm or 200 nm Lipofast™ filters (Avestin, Inc.) according to manufacturers instructions to obtain lipid suspensions consisting of particles less than about 50 nm, 100 nm or 200 nm diameter respectively. Unsized lipid preparations were obtained by vortexing the lipid for 5 minutes after 10 freeze-thaw cycles. After transfection, the cells were washed once with 2 mL of medium without phenol red and the glass cover slip was removed from the tissue culture plate and observed by fluorescence microscopy. Results of the transfections are described below.

| cell line | lipid | oligonucleotide concentration* | oligonucleotide transfected** |
|---|---|---|---|
| A549 | 1 | | |
| | unsized | 30 | ++ |
| | | 90 | +++ |
| | | 250 | ++ |
| A549 | 2 | | |
| | unsized | 30 | +++ |
| | | 90 | ++ |
| | | 250 | + |
| A549 | 3 | | |
| | unsized | 30 | ++ |
| | | 90 | + |
| | | 250 | − |
| CV-1 | 1 | | |
| | unsized | 30 | ++ |
| | | 90 | ++ |
| | | 250 | +++ |
| CV-1 | 2 | | |
| | unsized | 30 | +++ |
| | | 90 | +++ |
| | | 250 | ++ |
| CV-1 | 3 | | |
| | unsized | 30 | ++ |
| | | 90 | ++ |
| | | 250 | + |
| RKO | 1 | | |
| | unsized | 90 | ++ |
| | unsized*** | 90 | +++ |
| RKO | 2 | | |
| | unsized | 90 | ++ |
| | unsized*** | 90 | +++ |
| RKO | 3 | | |
| | unsized | 90 | ++ |
| | unsized*** | 90 | +++ |
| BxPC3 | 1 | | |
| | unsized*** | 30 | + |
| BxPC3 | 2 | | |
| | unsized | 30 | +/− |
| | unsized*** | 30 | + |
| | 50 | 30 | +/− |
| | 50 | 90 | +/− |
| | 100 | 90 | +/− |
| | 200 | 30 | +/− |
| | 200 | 90 | +/− |
| BxPC3 | 3 | | |
| | unsized | 30 | + |
| | unsized*** | 30 | + |

*Oligonucleotide concentration (nM) in lipid preparation.
**(−)No transfection detected as reflected by no observed fluorescence from transfected cells; (+/−) low amount of ODN transfected into cells as reflected by low fluorescence intensity of transfected cells; (+) moderate transfection; (++) good transfection; (+++) excellent transfection with intense cell fluorescence.
***Transfection used 5 µg of lipid instead of 2.5 µg.

Example 9

Several lipid formulations were tested for their ability to deliver fluorescein labeled 15-mer oligonucleotide having phosphorothioate linkages to cells in mice. Lipids complexed with labeled oligonucleotides were delivered into female Swiss Webster mice by tail vein injection of 0.3 mL of a sterile PBS solution (pH 7.0) containing the complexes. Lipid suspensions were prepared by adding 4 mL of water to 20 mg of dried lipid film in a flask (100 mL round bottom flask) followed by vortexing the flask for 5–10 minutes and then subjecting the solution to 6–7 freeze-thaw cycles (dry ice freezing and thawing in air at room temperature). Lipid-oligonucleotide complexes were prepared by mixing an equal volume of lipid suspension (150 µL containing 5, 2, 1 or 0.4 mg lipid per mL) from the freeze-thaw treatments with oligonucleotide in 150 µL PBS (0.1 mg/mL). The lipid and oligonucleotide for each injection was mixed by drawing the solution into a micropipette 2–3 times. The lipid and oligonucleotide were allowed to form a complex for 5 minutes and then the mice were injected. Several lipid oligonucleotide ratios were used which were expressed as the lipid:oligonucleotide charge ratio (+:−). This charge ratio was the ratio of cationic amphiphile to the anionic phosphorothioate charge. For GS 2888, a charge of +1 was assumed for the lipid molecule at physiological pH, for GS 3793, a charge of 0 was assumed and for the oligonucleotide, a charge of −14 was assumed. All injections delivered 0.5 mg oligonucleotide per kg to the mice. Twenty four hours after injection, the mice were euthanized, and perfused to fix the tissues as follows.

The mice were euthanized by cervical dislocation and the thorax was opened carefully to limit bleeding. A 30 mL syringe (23 ga needle) filled with PBS was inserted intro the left ventricle and the right ventricle was opened for drainage. PBS was slowly perfused into the heart. After most of the blood was flushed out, a second syringe filled with 4% paraformaldehyde was inserted into the same puncture in the left ventricle and the mice were perfused with about 20 mL of the paraformaldehyde solution. Tissues were removed and placed in cold CryoKwik™ (Damon), mounted in a cutting chuck with a thin layer of OCT compound (Tissue Tek II™, Miles), and cooled in a cryostat. 10 µm sections were cut and transferred to glass slides. The sections were fixed with 3.7% formaldehyde in PBS for 10 min., followed by a 5 min. wash in 50 mM glycine in PBS. Cell nuclei were stained with the blue fluorescent dye 4',6-diamidino-2-phenylindole dihydrochloride (DAPI). Coverslips were mounted and viewed by fluorescence microscopy using a Nikon Diaphot microscope, equipped with a 60× lens, mercury light source and fluorescein and DAPI filters. Nuclear localization of the fluorescein-conjugated oligonucleotidle was confirmed by co-localization with the DAPI-stained nuclei. The results are shown in the table below. The control transfection used no lipid and oligonucleotide alone in PBS and delivered 0.5 mg/kg oligonucleotide. The lipid formulations in PBS resulted in the formation of aggregates within several minutes at charge ratios of 25:1 and 5:1—such aggregates were not observed at lower lipid:oligonucleotide charge ratios under the same conditions. The mice were injected with the lipid-oligonucleotide complexes 5 minutes after the two components were mixed together. The fluorescence intensity observed in the cells is expressed in the table below as no fluorescence observed (−), very low intensity (+/−), low intensity (+), moderate intensity (++), or high intensity (+++).

| lipid | charge ratio (+/−) | liver | lung | spleen | kidney |
|---|---|---|---|---|---|
| GS 2888: | 25:1 | + | − | + | + |
| DOPE (2:1) | 5:1 | ++ | − | +++ | +/− |
| | 1:1 | + | − | + | + |
| | 0.2:1 | + | − | + | + |
| GS 3793: | 25:1 | + | − | + | + |
| DOPE (1:1) | 5:1 | ++ | − | +++ | +/− |
| | 1:1 | + | − | + | + |
| | 0.2:1 | + | − | + | + |
| GS 3793: | 25:1 | + | +++ | ++ | +/− |
| no colipid | 5:1 | + | ++ | ++ | +/− |
| | 1:1 | ++ | − | ++ | + |
| | 0.2:1 | ++ | − | + | + |
| no lipid | | + | − | − | ++ |

Transfections using 3793 without colipid resulted in efficient oligonucleotide delivery into cell nuclei. Transfections using 2888 or 3793 with DOPE as the fusogenic colipid resulted in delivery of the bulk of oligonucleotide into endosomes in the cells. This result indicated that most of the oligonucleotide that entered cells was not free in the cell cytoplasm, but was trapped in endosomes instead. By contrast, oligonucleotide delivered using 3793 without colipid indicated that the bulk of the oligonucleotide in the tissues was delivered to the cell cytoplasm because most or all of the observed fluorescence was observed in cell nuclei. Previous work has shown that cells rapidly transport oligonucleotides such as phosphorothioate linked oligonucleotide analogs which are initially present in cellular cytoplasm into the nucleus (Fisher et al. *Nucl. Acids Res.* 21:3857–3865, 1993, Wagner et al. *Science* 260:1510–1513, 1993). Previous work has described oligonucleotide transfection using 2888 (Lewis et al. *Proc. Natl. Acad. Sci.* (U.S.A.) 93:3176–3181, 1996, WO 96/01841, WO 96/01840).

Example 10

Lipid-oligonucleotide complexes were prepared as described in example 9 using GS 3793 without colipid and fluorescently labeled oligonucleotide at charge ratio of 25:1. The complexes were prepared using PBS or 5% dextrose in water. The complexes prepared using 5% dextrose did not form aggregates and the PBS complexes aggregated as in example 9. One mouse (Swiss Webster) was injected by tail vein injection with 0.5 mg/kg of oligonucleotide (25 mg/kg of lipid) using either complex formulated in PBS or in 5% dextrose and 24 hours later, the same mice were given a second injection of the same dose of oligonucleotide (and lipid). The mouse injected with the complex prepared in dextrose died within 10 minutes after the injection. The mouse injected with the complex prepared in PBS showed signs of rapid breathing and lethargy within an hour after the injection—this animal was euthanized 1 hour after injection and the animal was perfused as described in example 9. Essentially the same results were observed as described in example 9 for the GS 3793 preparation at a 25:charge ratio lacking colipid, i.e., most oligonucleotide was observed in the lung and lesser amounts were observed in the spleen, kidney and liver. The same lipid-oligonucleotide complex prepared in 5% dextrose was injected into two nude mice (balb/c) and both animals died immediately after the first injection. These results suggested that in vivo doses of the GS 3793 lipid, at least to rodents, are preferably less than about 25 mg/kg of lipid, when delivery is by intravenous injection.

Example 11

A lipid-plasmid (luciferase expression plasmid) complex was prepared using several different lipid:plasmid charge ratios were used to transfect COS cells. The cells were transfected in the presence of 10% FBS. Complexes prepared using GS 3793 and DOPE (1:1) delivered about 10-fold more plasmid DNA to the cells than complexes prepared using GS 2888 and DOPE (2:1) while complexes of GS 3793 without colipid (DOPE) delivered about 6-fold less plasmid than GS 2888 prepared using DOPE. The amount of plasmid delivered to the cells was determined by measuring luciferase activity in the transfected cells 24 hours after transfection. All transfections used the same number of cells and the same amount of plasmid DNA and lipid per transfection.

Applicants hereby incorporate by reference each of the publications cited above in their entirety. Applicants hereby incorporate by reference each of the publications cited above with specificity.

What is claimed is:

1. A compound having the structure $\underline{A}$

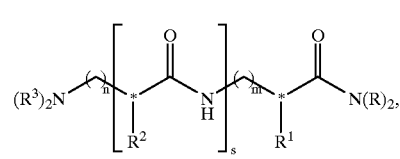

wherein
each R is independently hydrogen or a lipophilic moiety, provided that both R are not hydrogen;
$R^1$ and $R^2$ are independently hydrogen, $-(CH_2)_z-N(R^4)_2$, $-(CH_2)_zNR^4-C(NH)-N(R^5)_2$, or $W^1$, provided that at least one of $R^1$ and $R^2$ is $W^1$;
each $R^3$ is independently hydrogen, alkyl ($C_{1-10}$), $-CH_2-(CF_2)_p-CF_3$, aryl, a protecting group, or both $R^3$ together are a protecting group, or one $R^3$ is hydrogen and the other $R^3$ is $-C(O)CH_2NH_2$ or $-C(O)CHCH_3NH_2$, provided that both $R^3$ are not aryl;
each $R^4$ is independently hydrogen, alkyl ($C_{1-6}$), a protecting group, $-CH_2-(CF_2)_p-CF_3$, or both $R^4$ together are a protecting group;
each $R^5$ is independently hydrogen, alkyl ($C_{1-6}$), a protecting group, or both $R^5$ together are a protecting group;
each $W^1$ is independently a cationic group, at least one of which has a pKa of about 6.0–7.5;
m is an integer having the value 0, 1, 2, 3 or 4;
n is an integer having the value 0, 1, 2, 3 or 4;

p is an integer having the value 0, 1, 2, 3, 4, 5, 6, 7, 8, 9, or 10;

s is an integer having the value 0, 1 or 2;

z is an integer having the value 1, 2, 3, or 4;

positions designated * are carbon atoms in the R, S or RS configuration; or the salts, tautomers, solvates, resolved, partially resolved or unresolved enantiomers, purified, partially purified or unpurified positional isomers or diastereomers thereof.

2. The compound of claim 1 wherein $W^1$ is

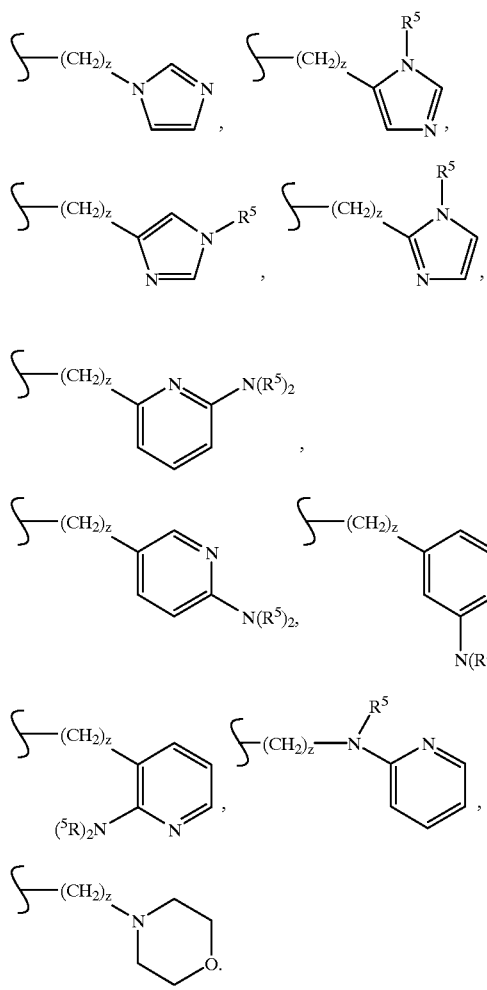

3. The compound of claim 2 wherein each $W^1$ independently is B, C, or D

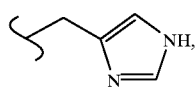

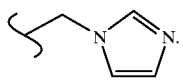

4. The compound of claim 1 wherein each R is independently a group containing about 10–50 linked carbon atoms.

5. The compound of claim 4 wherein m and n are both 0 and s is 1.

6. The compound of claim 5 wherein each group containing about 10–50 linked carbon atoms is independently alkyl ($C_{10-22}$), a mono-, di- or tri-unsaturated alkenyl ($C_{10-22}$) group, or one is a cholesteryl moiety and the other is hydrogen.

7. The compound of claim 6 wherein each group containing about 10–50 linked carbon atoms is independently alkyl ($C_{10-16}$).

8. The compound of claim 7 wherein each $W^1$ independently is

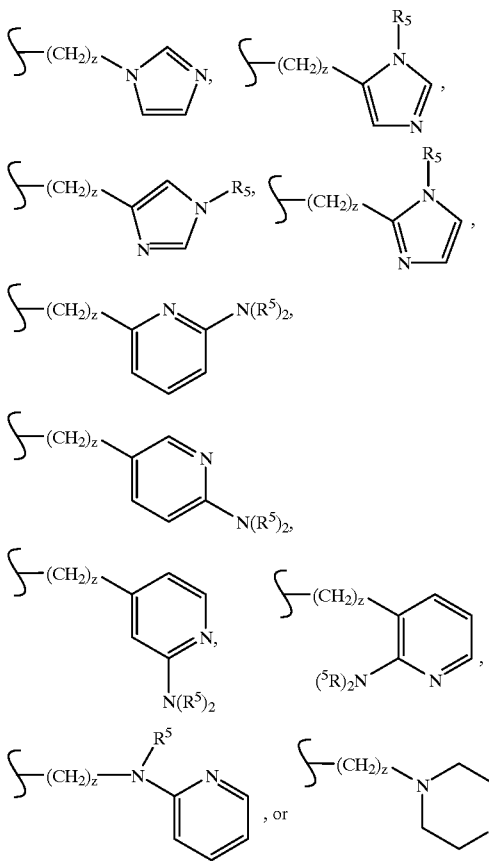

9. The compound of claim 8 wherein each $W^1$ independently is B, C, or D

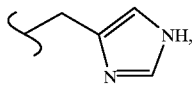

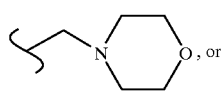

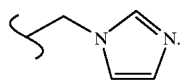

10. A compound having the structure A1

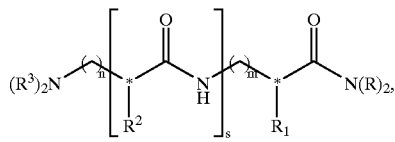

wherein each R is independently hydrogen or a lipophilic moiety, provided that both R are not hydrogen;

the lipophilic moiety is a $C_{10-22}$ alkane, a $C_{10-22}$ alkene or a cholesterol moiety of structure E;

E is

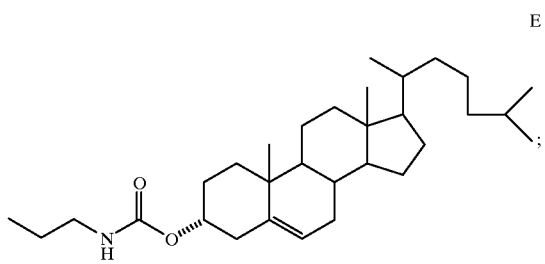

$R^1$ and $R^2$ are independently hydrogen, $-(CH_2)_z-N(R^4)_2$, $-(CH_2)_zNR^4-C(NH)-N(R^5)_2$, or $W^1$, provided that at least one of $R^1$ and $R^2$ is $W^1$;

each $R^3$ is independently hydrogen, alkyl $(C_{1-10})$, $-CH_2-(CF_2)_p-CF_3$, aryl, a protecting group, or both $R^3$ together are a protecting group, or one $R^3$ is hydrogen and the other $R^3$ is $-C(O)CH_2NH_2$ or $-C(O)CHCH_3NH_2$, provided that both $R^3$ are not aryl;

each $R^4$ is independently hydrogen, alkyl $(C_{1-6})$, a protecting group, $-CH_2-(CF_2)_p-CF_3$, or both $R^4$ together are a protecting group;

each $R^5$ is independently hydrogen, alkyl $(C_{1-6})$, a protecting group, or both $R^5$ together are a protecting group;

each $W^1$ is independently

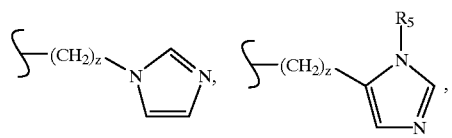

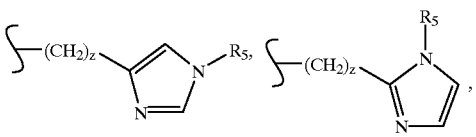

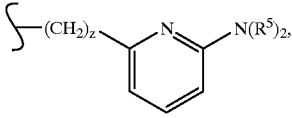

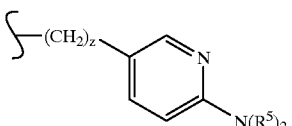

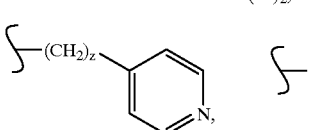

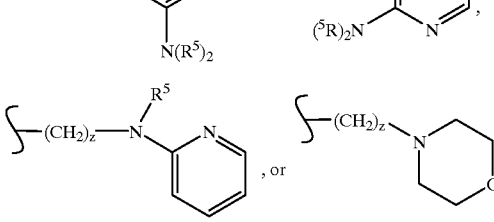

m is an integer having the value 0, 1, 2, 3 or 4;

n is an integer having the value 0, 1, 2, 3 or 4;

p is an integer having the value 0, 1, 2, 3, 4, 5, 6, 7, 8, 9, or 10;

s is an integer having the value 0, 1 or 2;

z is an integer having the value 1, 2, 3, or 4;

positions designated * are carbon atoms in the R, S or RS configuration; or the salts, tautomers, solvates, resolved, partially resolved or unresolved enantiomers, purified, partially purified or unpurified positional isomers or diastereomers thereof.

11. The compound of claim 10 wherein each $W^1$ independently is B, C, or D

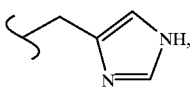

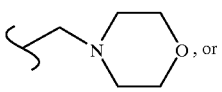

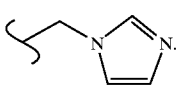

12. The compound of claim 10 wherein m and n are both 0 and s is 1.

13. A compound having the structure

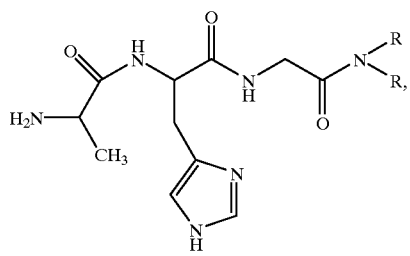

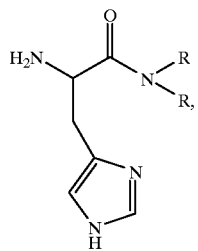

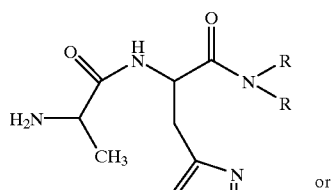

or

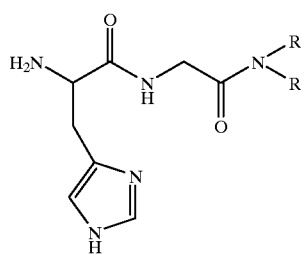

wherein R is n-$C_{14}H_{29}$.

14. The compound of claim 10 wherein each R is independently a group containing about 10–50 linked carbon atoms.

15. The compound of claim 14 wherein m and n are both 0 and s is 1.

16. The compound of claim 15 wherein each group containing about 10–50 linked carbon atoms is independently alkyl ($C_{10\text{-}22}$), a mono-, di- or tri-unsaturated alkenyl ($C_{10\text{-}22}$) group, or one R is a cholesteryl moiety and the other R is hydrogen.

17. The compound of claim 16 wherein each group containing about 10–50 linked carbon atoms is independently alkyl ($C_{10\text{-}16}$).

18. The compound of claim 17 wherein each $W^1$ independently is B, C, or D

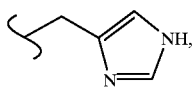

B

-continued

C

D

19. A compound having the structure E

E wherein
q and r are each independently 0, 1, 2 or 3;
each R is independently hydrogen or a lipophilic moiety, provided that both R are not hydrogen;
$R^{11}$ is a moiety with a pKa of about 6.0–10; and
$R^{12}$ is a $W^1$ moiety with a pKa of about 6.0–7.5.

20. The compound of claim 19 wherein $W^1$ is

wherein
each $R^5$ is independently hydrogen, alkyl ($C_{1\text{-}6}$), a protecting group, or both $R^5$ together are a protecting group; and z is 1, 2, 3, or 4.

21. A compound having the structure E1

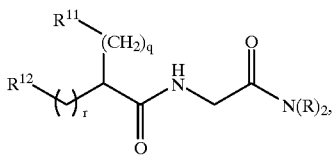

wherein q and r are each independently 0, 1, 2 or 3;

each R is independently hydrogen or a lipophilic moiety, provided that both R are not hydrogen;

$R^{11}$ is $-N(R^4)_2$ or $-N(R^{14})(R^4)$ when q is 0 and $R^{11}$ is $-NH-CH_2-CN$, $-NH-CH_2-NO_2$, $-NH-CH_2-SO_2R^{15}$, $-NH-CH_2-C(O)(CH_2)_mCH_3$, $-NH-CH_2(CF_2)_lCF_3$, or $-NH-CH_2O(CH_2)_mCH_3$, when q is 1, 2, or 3;

$R^{12}$ is $W^1$;

$R^{14}$ is hydrogen or alkyl $(C_{1-6})$;

$R^{15}$ is hydrogen or alkyl $(C_{1-6})$;

$W^1$ is

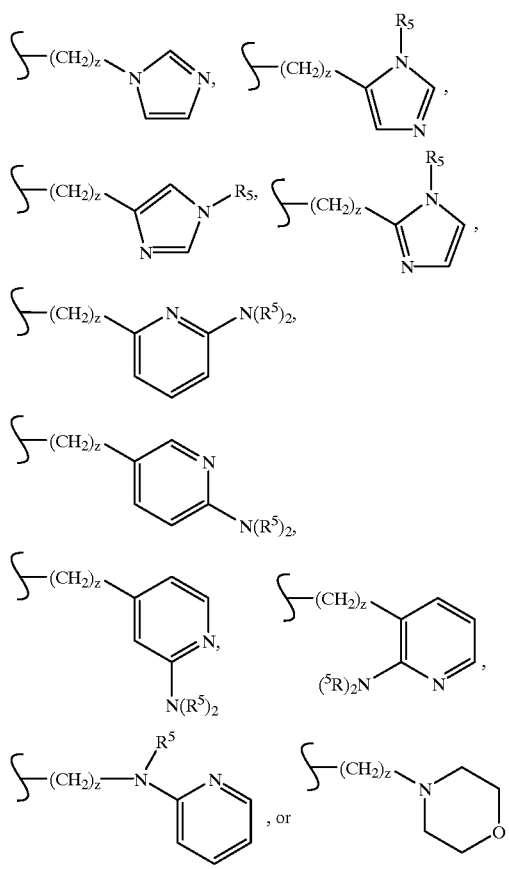

each $R^5$ is independently hydrogen, alkyl $(C_{1-6})$, a protecting group, or both $R^5$ together are a protecting group; and z is 1, 2, 3, or 4.

22. The compound of claim 21 wherein $W^1$ is B, C or D

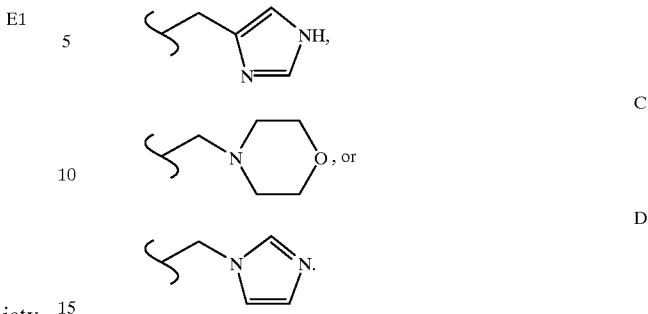

23. The cationic lipid of claim 22 wherein each lipophilic moiety is independently alkyl $(C_{10-22})$, a mono-, di-, or tri-unsaturated$(C_{10-22})$ alkenyl group, or one R is a cholesteryl moiety and the other R is hydrogen.

24. The cationic lipid of claim 23 wherein $R^{11}$ is $-NH_2$.

25. The cationic lipid of claim 23 wherein q is 0 and r is 1 or q is 1 and r is 0.

26. The cationic lipid of claim 23 wherein both R are the same and are alkyl $(C_{12-16})$.

27. A composition comprising the lipid of claim 10 and a colipid.

28. The composition of claim 27 wherein the colipid is DOPE.

29. A composition comprising the lipid of claim 10 and 9-(3-hydroxy-2-phosphonylmethoxypropyl)cytosine, 9-(2-phosphonylmethoxyethyl)adenine, 9-(2-phosphonylmethoxyethyl)guanine, 9-(2-phosphonylmethoxypropyl)adenine, 9-(2-phosphonylmethoxypropyl)2,6-diaminopurine or a polyanionic compound selected from the group consisting of a nucleic acid, an oligonucleotide, a peptide and a protein.

30. The composition of claim 29 wherein the nucleic acid is a circular or linear plasmid or is a ribonucleic acid.

31. The composition of claim 29 wherein the composition comprises 9-(3-hydroxy-2-phosphonylmethoxypropyl)cytosine, 9-(2-phosphonylmethoxyethyl)adenine, 9-(2-phosphonylmethoxyethyl)guanine or 9-(2-phosphonylmethoxypropyl)adenine.

32. A cationic lipid of claim 10 having a moiety with a pKa of about 6.0 to 7.5 wherein the pKa is determined by the process of:

(a) preparing a water solution containing a suspension of the HCl salt of the cationic lipid at a concentration of about 2-fold above the cationic lipid's CMC to obtain a cationic lipid suspension;

(b) measuring the pH of the cationic lipid suspension;

(c) adding 0.1 equivalent of a NaOH solution in water and mixing the NaOH solution into the cationic lipid suspension;

(d) measuring the pH of the suspension of step (c) to obtain a pH value;

(e) repeating steps (c) and (d) until one has added 1.0 equivalents of the NaOH solution and obtained the pH value at completion of each repetition of step (d);

(f) plotting each pH value obtained from each repetition of step (d) versus the number of equivalents of added NaOH; and (g) determining the pKa of the cationic lipid using an inflection point of the pH versus equivalents of added NaOH curve.

33. A cationic lipid of claim 21 having a moiety with a pKa of about 6.0 to 7.5 wherein the pKa is determined by the process of:

(a) preparing a water solution containing a suspension of the HCl salt of the cationic lipid at a concentration of about 2-fold above the cationic lipid's CMC to obtain a cationic lipid suspension;

(b) measuring the pH of the cationic lipid suspension;

(c) adding 0.1 equivalent of a NaOH solution in water and mixing the NaOH solution into the cationic lipid suspension;

(d) measuring the pH of the suspension of step (c) to obtain a pH value;

(e) repeating steps (c) and (d) until one has added 1.0 equivalents of the NaOH solution and obtained the pH value at completion of each repetition of step (d);

(f) plotting each pH value obtained from each repetition of step (d) versus the number of equivalents of added NaOH; and (g) determining the pKa of the cationic lipid using an inflection point of the pH versus equivalents of added NaOH curve.

34. The compound of claim 1 wherein the lipophilic moiety is a $C_{10-22}$ alkane, a $C_{10-22}$ alkene, cholesterol, a diacylglycerol or a triacylglycerol; and the cationic group is independently

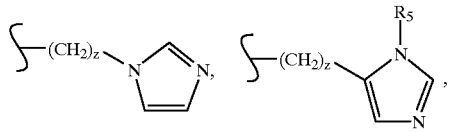

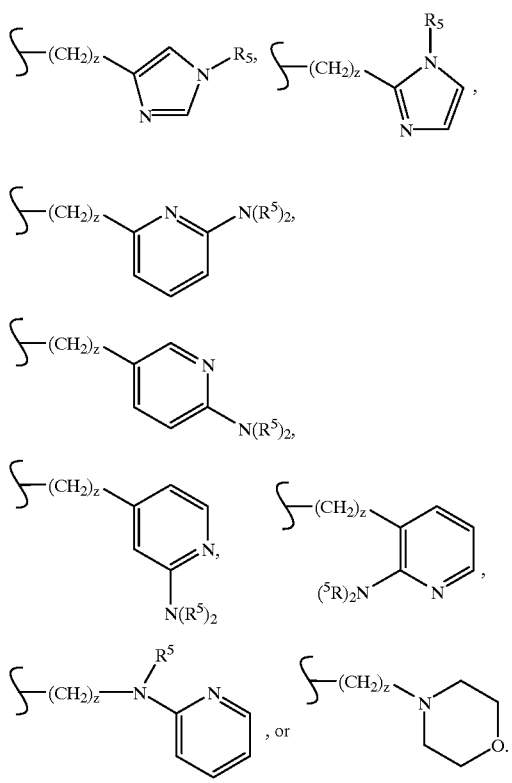

* * * * *

UNITED STATES PATENT AND TRADEMARK OFFICE
CERTIFICATE OF CORRECTION

PATENT NO.    : 6,093,816
DATED         : July 25, 2000
INVENTOR(S)   : Lin et al.

It is certified that error appears in the above-identified patent and that said Letters Patent is hereby corrected as shown below:

Column 4,
Line 11, please delete "R" and insert therefor -- r --.

Columns 9 and 10,
Table 2, please delete 1$^{st}$ occurrence of "4.1.1.4" and insert therefor -- 4.1.1.1 -- and please delete "7.7.1.4" and insert therefor -- 7.7.1.1 --.

Columns 11 and 12,
Table 2, please delete 1$^{st}$ occurrence of "5.3.3.4" and insert therefor -- 5.3.3.1 --, please delete "5.8.3.4" and insert therefor -- "5.8.3.1 -- and please delete "2.2.S.4" and insert therefor -- 2.2.5.4 --.

Columns 13 and 14,
Table 2, please delete "5.3.7.4" and insert therefor -- 5.3.7.1 --.

Column 17,
Line 5, please delete "tungssten" and insert therefor -- tungsten --.
Line 6, please delete "carbeniyl" and insert therefor -- carbenyl --.

Column 28,
Line 7, please delete "nosine" and insert therefor -- inosine --.
Line 61, please delete "cytokinies" and insert therefor -- cytokines --.

Column 40,
Lines 25 and 57, please delete "$\geqq$" and insert therefor -- $\geq$ --.
Line 64, please delete "phsphorothioate" and insert therefor -- phosphorothioate --.
Line 67, please delete "phosphtoramidite" and insert therefor -- phosphoramidite --.

Column 42,
Line 49, please delete "intro" and insert therefor -- into --.

Column 43,
Line 1, please delete "oligonucleotidle" and insert therefor -- oligonucleotide --.

UNITED STATES PATENT AND TRADEMARK OFFICE
CERTIFICATE OF CORRECTION

PATENT NO.    : 6,093,816
DATED         : July 25, 2000
INVENTOR(S)   : Lin et al.

It is certified that error appears in the above-identified patent and that said Letters Patent is hereby corrected as shown below:

Column 51,
Line 21, please delete "$(CF_2)_1$" and insert therefor -- $(CF_2)_m$ --.

Signed and Sealed this

Tenth Day of December, 2002

JAMES E. ROGAN
*Director of the United States Patent and Trademark Office*